United States Patent [19]
Duncia

[11] Patent Number: 5,332,820
[45] Date of Patent: Jul. 26, 1994

[54] DIBENZOBICYCLO(2.2.2) OCTANE ANGIOTENSIN II ANTAGONISTS

[75] Inventor: John J. V. Duncia, Newark, Del.

[73] Assignee: E. I. Du Pont de Nemours and Company, Wilmington, Del.

[21] Appl. No.: 702,281

[22] Filed: May 20, 1991

[51] Int. Cl.$^5$ .............. C07D 403/02; C07D 471/04; A61K 31/41; A61K 31/415
[52] U.S. Cl. .................... 546/118; 548/251; 548/252; 548/253
[58] Field of Search ............ 548/253, 251, 252; 514/381, 303; 546/118

[56] References Cited

U.S. PATENT DOCUMENTS

| | | | |
|---|---|---|---|
| 3,772,315 | 11/1973 | Regel et al. | 260/296 R |
| 4,207,324 | 6/1980 | Matsumura et al. | 424/273 R |
| 4,226,878 | 10/1980 | Iizuka et al. | 424/273 R |
| 4,226,948 | 10/1980 | Popoff et al. | 548/215 |
| 4,340,598 | 7/1982 | Furukawa et al. | 424/273 R |
| 4,355,040 | 10/1982 | Furukawa et al. | 424/273 R |
| 4,379,927 | 4/1983 | Vorbrüggen et al. | 544/139 |
| 4,448,781 | 5/1984 | Cross et al. | 424/269 |

FOREIGN PATENT DOCUMENTS

| | | |
|---|---|---|
| 0103647 | 3/1984 | European Pat. Off. |
| 0125033 | 11/1984 | European Pat. Off. |
| 0146228 | 6/1985 | European Pat. Off. |
| 0245637 | 11/1987 | European Pat. Off. |
| 0253310 | 1/1988 | European Pat. Off. |
| 0324377 | 7/1989 | European Pat. Off. |

OTHER PUBLICATIONS

Torii et al., Metabolism and Disposition of 4--Chloro-1-(4-methoxy-3-methylbenzyl)-2--phenylimidazole-5-acetic Acid (CV-2973), a New Hypotensive Agent with Diuretic Activity, in Rats and Dogs, J. Takeda Res. Lab., vol. 41, No. 3/4, pp. 181–191(1982).
Pals et al., Role of the Pressor Action of Angiotensin II in Experimental Hypertension, Circulation Research, vol. XXIX, Dec. 1971, pp. 673-681.
Streeten et al., 8. Angiotensin-receptor blocking drugs, Handbook of Hypertension, vol. 5, Clinical Pharmacology of Antihypertensive Drugs, pp. 246-271 (1984).
Keeton et al., The Pharmacologic Alteration of Renin Release, Pharmacological Reviews, vol. 31, No. 2, pp. 81-227 (1981).
Myron H. Weinberger MD, Angiotensin-Converting Enzyme Inhibitors, Medical Clinics of North America, vol. 71, No. 5, pp. 979-991, Sep. 1987.
Dunn, Clinical Effects of Prostaglandins in Renal Disease, Reprinted from Hospital Practice, Mar. 1984, vol. 19, No. 3, pp. 99–113.
Satoh et al., Influence of the Renin-Angiotensin System on the Effect of Prostaglandin Synthesis Inhibitors in the Renal Vasculature, Supplement I to Circulation Research, vols. 36 and 37, pp. I-89 through I-96, Jun. 1975.
Blasingham et al., Differential renal effects of cyclooxygenase inhibition in sodium-replete and sodium-deprived dog, 1980 the American Physiological Society, pp. F360-F365.
Wong et al., Mechanism of Captopril-Induced Renal Vasodilatation in Anesthetized Dogs after Nonhypotensive Hemorrhage, The Journal of Pharmacology and Experimental Therapeutics, pp. 104-109, accepted for publication Jun. 30, 1980.

Primary Examiner—David B. Springer

[57] ABSTRACT

Novel substituted dibenzobicyclo[2.2.2]octanes of formula I, which are useful as angiotensin II antagonists, are disclosed:

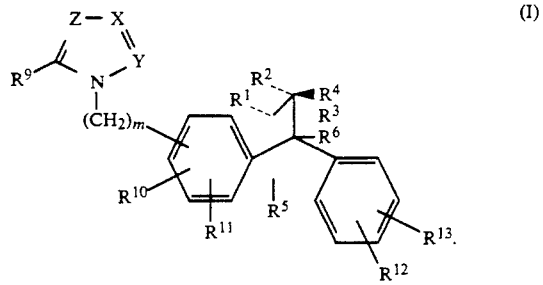

10 Claims, No Drawings

DIBENZOBICYCLO(2.2.2) OCTANE ANGIOTENSIN II ANTAGONISTS

BACKGROUND OF THE INVENTION

This invention relates to novel substituted dibenzobicyclo[2.2.2]octanes, and processes for their preparation. The invention also relates to pharmaceutical compositions containing the novel dibenzobicyclo[2.2.2]octanes and pharmaceutical methods using them, alone and in conjunction with other drugs, especially diuretics and non-steroidal anti-inflammatory drugs (NSAID's).

The compounds of this invention inhibit the action of the hormone angiotensin II (AII) and are useful therefore in alleviating angiotensin induced hypertension. The enzyme renin acts on a blood plasma $\alpha_2$-globulin, angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a non-steroidal anti-inflammatory drug (NSAID) can prevent renal failure which sometimes results from administration of a NSAID.

European Published Application 0 253 310, published Jan. 20, 1988, discloses that certain substituted imidazoles block the AII receptor and are useful therefore in alleviating angiotensin induced hypertension as well as in treating congestive heart failure.

Pals, et al., *Circulation Research*, 29, 673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [Sar[1], Ala[8]] AII initially called "P-113" and subsequently "Saralasin", was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals, et al., *Circulation Research*, 29, 673 (1971); Streeten and Anderson, *Handbook of Hypertension*, Vol. 5, *Clinical Pharmacology of Antihypertensive Drugs*, A. E. Doyle (Editor), Elsevier Science Publishers B. V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

Some known non-peptide antihypertensive agents ace by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's. Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized. Diuretic treatment converts the non-renin dependent state in regulating blood pressure to a renin-dependent state. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril maleate and the diuretic hydrochlorothiazide is commercially available under the trademark Vaseretic ® from Merck & Co. Publications which relate to the use of diuretics with CEI's to treat hypertension, in either a diuretic-first, stepwise approach or in physical combination, include T. K. Keeton and W. B. Campbell, *Pharmacol. Rev.*, 31:81 (1981) and M. H. Weinberger, *Medical Clinics N, America*, 71:979 (1987). Diuretics have also been administered in combination with saralasin to enhance the antihypertensive effect.

Non-steroidal anti-inflammatory drugs (NSAID's ) have been reported to induce renal failure in patients with renal underperfusion and high plasma level of AII. (M. J. Dunn, *Hospital Practice*, 19:99 (1984)). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh, et al., *Circ. Res.*, 36/37 (Suppl. I):I-89, 1975; Biasingham, et al., *Am, J. Physiol.*, 239:F360, 1980). The CEI captopril has been demonstrated to reverse the renal vasoconstrictor effect of indomethacin in dogs with non-hypotensive hemorrhage. (Wong, et al., *J. Pharmacol. Exp. Ther.*, 219:104, 1980).

SUMMARY OF THE INVENTION

According to the present invention there are provided novel compounds of formula I which have angiotensin II-antagonizing properties and are useful as antihypertensives:

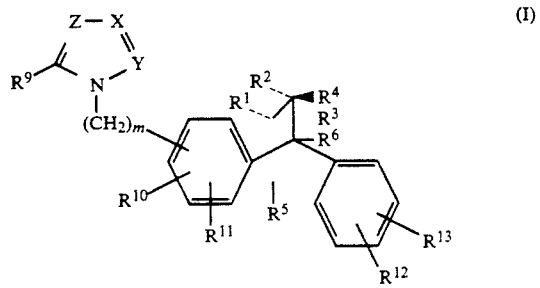

(I)

wherein $R^1$, $R^2$, $R^3$, and $R^4$ are independently —COOH, —CONHOR$^{14}$; —CONHNHSO$_2$CF$_3$; —NHSO$_2$CF$_3$; —CH$_2$NHSO$_2$CF$_3$;

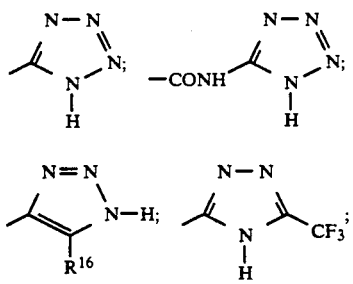

alkyl of 1 to 5 carbon atoms; perfluoroalkyl of 1 to 5 carbon atoms; CN, —CO$_2$R$^{15}$ phenyl; or where $R^1$ and $R^2$ or $R^3$ and $R^4$ are taken together to form an aliphatic ring of 3 to 6 carbon atoms; provided that at least one of $R^1$, $R^2$, $R^3$, and $R^4$ is always an acidic group defined by —COOH, —CONHOR$^{14}$; —CONHNHSO$_2$CF$_3$; —NHSO$_2$CF$_3$; —CH$_2$NHSO$_2$CF$_3$;

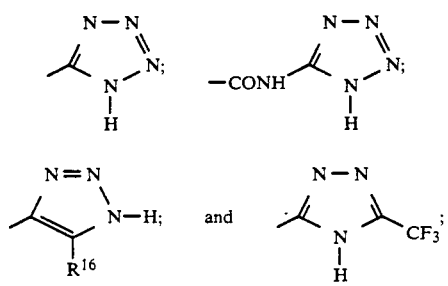

$R^5$ and $R^6$ are independently H, CH$_3$, Cl, Br, I, F, —OCH$_3$, —OCOCH$_3$;

$R^7$ is H, F, Cl, Br, I, NO$_2$, perfluoroalkyl of 1 to 5 carbon atoms; CN; COR$^{17}$; straight or branched alkyl of 1 to 6 carbon atoms; phenyl; phenylthio; alkenyl of 2 to 10 carbon atoms; alkynyl of 2 to 10 carbon atoms; phenylalkenyl where the alkenyl portion is 2 to 6 carbon atoms; phenylalkynyl where the alkynyl portion is 2 to 6 carbon atoms; heteroaryl selected from 2- and 3-thienyl, 2- and 3-furyl, 2-, 3-, and 4-pyridyl, 2-, 4-, and 5-oxazolyl; substituted phenyl, phenylalkenyl, phenylalkynyl, and heteroaryl, with one or two substituents selected from halogen, alkoxy of 1 to 5 carbon atoms, alkyl of 1 to 5 carbon atoms, —NO$_2$, —CN, —CF$_3$, —COR$^{15}$, —CH$_2$OR$^{18}$ and —NHCOR$^{18}$ where $R^{18}$ is other than H; 1- or 2-naphthyl; 2-, 3-, 4-, 5-, 6-, 7-, or 8-quinolinyl; 1-, 3-, 4-, 5-, 6-, 7-, or 8-isoquinolinyl; 2-, 3-, 4-, 5-, 6-, or 7-benzofuryl, where any of the foregoing polycyclic heteroaryl groups can be substituted with one or two substituents selected from halogen, alkoxy of 1 to 5 carbon atoms, alkyl of 1 to 5 carbon atoms, —NO$_2$, —CN, —CF$_3$, —COR$^{15}$, —CH$_2$OR$^{18}$, and —NHCOR$^{18}$ where $R^{18}$ is other than H;

$R^8$ is H; CN; COR$^{17}$; —(CH$_2$)$_{n-1}$CH(OR$^{18}$)R$^{19}$; —(CH$_2$)$_n$O(CO)R$^{18}$ where $R^{18}$ is other than H; —(CH$_2$)$_n$COR$^{17}$;

$R^9$ is alkyl of 1 to 6 carbon atoms; alkenyl or alkynyl of 2 to 6 carbon atoms; cycloalkyl of 3 to 8 carbon atoms; cycloalkylalkyl of 4 to 8 carbon atoms; alkylthio where the alkyl portion is of 2 to 5 carbon atoms;

$R^{10}$, $R^{11}$, $R^{12}$, $R^{13}$ are independently H, Cl, Br, I, F, NO$_2$, CN, OH, alkyl of 1 to 4 carbon atoms; acyloxy of 1 to 4 carbon atoms; alkoxy of 1 to 4 carbon atoms, —CO$_2$H, —CO$_2$R15; —NHSO$_2$CF$_3$; —CONHOR$^{14}$; aryl;

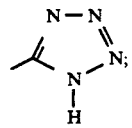

$R^{14}$ is H, methyl or benzyl;
$R^{15}$ is H; alkyl of 1 to 5 carbon atoms; branched alkyl of 1 to 5 carbon atoms; phenyl;
$R^{16}$ is CN, NO$_2$, or CO$_2$R$^{15}$;
$R^{17}$ is H, alkyl of 1 to 6 carbon atoms; —OR$^{15}$; —NR$^{18}$R$^{19}$;
$R^{18}$ and $R^{19}$ are independently H, alkyl of 1 to 5 carbon atoms; phenyl;
$R^{20}$ and $R^{21}$ are independently —H; Cl; Br; I; —SR$^{15}$; —R$^{17}$; —CN; —OR$^{15}$; phenyl; substituted phenyl where the substituents are alkoxy of 1 to 5 carbon atoms, alkyl of 1 to 5 carbon atoms, fluorine;
Z is N; CH;
X is C—R$^7$; C—R$^8$; N;
Y is C—R$^8$; C—R$^7$; N;
X and Y are carbon atoms when they are part of the following ring system:

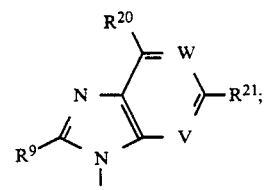

V is CH; N;
W is CH; N;
m is 1,2;
n is 1-5;

provided that X and Y are not both CR$^7$ simultaneously and that X and Y are not both CR$^8$ simultaneously.

Preferred for their antihypertensive activity are novel compounds having the formula:

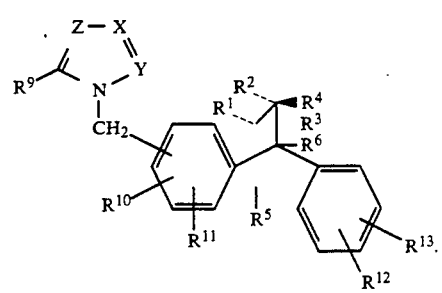

II wherein
$R^1$, $R^2$, $R^3$, and $R^4$ are independently —COOH, —CONHOR$^{14}$;

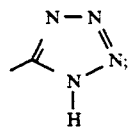

—CONHNHSO$_2$CF$_3$; alkyl of 1 to 5 carbon atoms; perfluoroalkyl of 1 to 5 carbon atoms; CN, —CO$_2$R$^{15}$, or where R$^1$ and R$^2$ or R$^3$ and R$^4$ are taken together to form an aliphatic ring of 3 to 6 carbon atoms; provided that at least one of R$^1$, R$^2$, R$^3$ and R$^4$ is always an acidic group defined by —COOH, —CONHOR$^{14}$; —CONHNHSO$_2$CF$_3$;

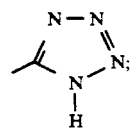

R$^5$ and R$^6$ are independently H; —CH$_3$; —OCH$_3$;
R$^7$ is H, F, Cl, Br, I, NO$^2$, perfluoroalkyl of 1 to 5 carbon atoms; —COR$^{17}$; straight or branched alkyl of 1 to 6 carbon atoms; phenyl; phenylthio; alkenyl of 2 to 10 carbon atoms; alkynyl of 2 to 10 carbon atoms; phenylalkenyl where the alkenyl portion is 2 to 6 carbon atoms; phenylalkynyl where the alkynyl portion is 2 to 6 carbon atoms; heteroaryl selected from 2- and 3-thienyl, 2- and 3-furyl, 2-, 3-, and 4-pyridyl, 2-, 4-, and 5-oxazolyl; substituted phenyl, phenylalkenyl, phenylalkynyl, and heteroaryl, with one or two substituents selected from halogen, alkoxy of 1 to 5 carbon atoms, alkyl of 1 to 5 carbon atoms, —NO$_2$, —CN, —CF$_3$, —COR$^{15}$, —CH$_2$OR$^{18}$, and —NHCOR$^{18}$ where R$^{18}$ is other than H; 1-or 2-naphthyl; 2-, 3-, 4-, 5-, 6-, 7-, or 8-quinolinyl; 1-, 3-, 4-, 5-, 6-, 7-, or 8-isoquinolinyl; 2-, 3-, 4-, 5-, 6-, or 7-benzofuryl, where any of the foregoing polycyclic heteroaryl groups can be substituted with one or two substituents selected from halogen, alkoxy of 1 to 5 carbon atoms, and alkyl of 1 to 5 carbon atoms;
R$^8$ is H, —COR$^{17}$; —(CH$_2$)$_n$—CH(OR$^{18}$)R$^{19}$; —(CH$_2$)$_n$O(CO)R$^{18}$ where R$^{18}$ is other than H; —(CH$_2$)$_n$COR$^{17}$;
R$^9$ is alkyl of 2 to 6 carbon atoms; alkenyl or alkynyl of 2 to 6 carbon atoms; alkylthio where the alkyl portion is of 2 to 5 carbon atoms;
R$^{10}$, R$^{11}$, R$^{12}$, R$^{13}$ are independently H, Cl, Br, F, alkyl of 1 to 4 carbon atoms; alkoxy of 1 to 4 carbon atoms;
R$^{14}$ is H, methyl or benzyl;
R$^{15}$ is H; alkyl of 1 to 5 carbon atoms; branched alkyl of 1 to 5 carbon atoms; phenyl;
R$^{16}$ is CN, NO$_2$, or CO$_2$R$^{15}$;
R$^{17}$ is H, alkyl of 1 to 6 carbon atoms; —OR$^{15}$; —NR$^{18}$R$^{19}$;
R$^{18}$ and R$^{19}$ are independently H, alkyl of 1 to 5 carbon atoms; phenyl;
R$^{20}$ and R$^{21}$ are independently —H; Cl; Br; I; —SR$_{15}$; —R$_{17}$; —CN; —OR$^{15}$; phenyl; substituted phenyl where the substituents are alkoxy of 1 to 5 carbon atoms, alkyl of 1 to 5 carbon atoms, fluorine;
Z is N; CH;
X is C—R$^7$; C—R$^8$; N;
Y is C—R$^8$; C—R$^7$; N;

X and Y are carbon atoms when they are part of the following ring system:

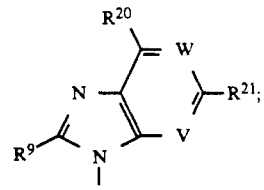

V is CH; N;
W is CH; N;
n=1–5
provided that X and Y are not both CR$^7$ simultaneously and that X and Y are not both CR$^8$ simultaneously.
More preferred are compounds of the preferred scope where:
R$^1$, R$^2$, R$^3$ and R$^4$ are independently —COOH, —CONHOR$^{14}$;

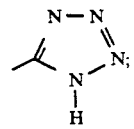

CONHMHSO$_2$CF$_3$; alkyl of 1 to 5 carbon atoms; perfluoroalkyl of 1 to 5 carbon atoms; CN; —CO$_2$R$^{15}$, or where R$^1$ and R$^2$ or R$^3$ and R$^4$ are taken together to form an aliphatic ring of 3 to 6 carbon atoms; and where at least one of R$^1$, R$^2$, R$^3$ and R$^4$ is always an acidic group defined by —COOH, —CONHOR$^{14}$; —CONHNHSO$_2$CF$_3$;

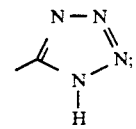

R$^5$ and R$^6$ are H;
R$^7$ is H, Cl, Br, I, NO2, perfluoroalkyl of 1 to 5 carbon atoms; —COR$^{17}$; alkyl of 1 to 5 carbon atoms; phenyl; phenylthio; alkenyl of 2 to 5 carbon atoms; alkynyl of 2 to 5 carbon atoms; phenylalkenyl where the alkenyl portion is 2 to 5 carbon atoms; phenylalkynyl where the alkynyl portion is 2 to 5 carbon atoms;
R$^8$ is H, COR$^{17}$; —(CH$_2$)$_{n-1}$CH$_2$ (OR$^{18}$);
R$^9$ is alkyl of 2 to 6 carbon atoms; alkenyl or alkynyl of 2 to 6 carbon atoms; alkylthio where the alkyl portion is of 2 to 5 carbon atoms;
R$^{10}$, R$^{11}$, R$^{12}$, R$^{13}$ are H;
R$^{14}$ is H, methyl or benzyl;
R$^{15}$ is H; alkyl of 1 to 5 carbon atoms; phenyl;
R$^{17}$ is H, alkyl of 1 to 6 carbon atoms; —OR$^{15}$; —NR$^{18}$R$^{19}$;
R$^{18}$ and R$^{19}$ are independently H, alkyl of 1 to 5 carbon atoms; phenyl;
R$^{20}$ and R$^{21}$ are independently-H; Cl; Br; I; —SR$^{15}$; —R$^{17}$; —CN; —OR$^{15}$; phenyl; substituted phenyl where the substituents are alkoxy of 1 to 5 carbon atoms, alkyl of 1 to 5 carbon atoms, fluorine;
Z is N; CH;
X is X is C—R$^7$; C—R$^8$; N;

Y is C—R⁸; C—R⁷; N;
X and Y are carbon atoms when they are part of the following ring system:

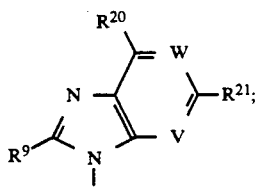

V is CH; N;
W is CH; N;
n is 1-5;
provided that X and Y are not both CR⁷ simultaneously and that X and Y are not both CR⁸ simultaneously.

Specifically preferred for their superior activity and/or safety are:

endo-(±)-cis-2-[(2-n-butyl-4-chloro-5-formylimidazol-1-yl)methyl]-9,10-dihydro-9,10-enthanoanthracene-11,12-dicarboxylic acid exo-(±)-cis-2-[(2-n-butyl-4-chloro-5-formylimidazol-1-yl)methyl]-9,10-dihydro-9,10-enthanoanthracene-11,12-dicarboxylic acid (±)-1 1R, 12R-trans-2-[(2-n-butyl-4-chloro-5-formylimidazol-1-yl)methyl]-9,10-dihydro-9,10-ethanoanthracene-11,12-dicarboxylic acid (±)-11S,12S-trans-2-[(2-n-butyl-4-chloro-5-formylimidazol-1-yl) methyl]-9,10-dihydro-9,10-ethanoanthracene-11,12-dicarboxylic acid (±)-11R,12R-trans-2-[(2-n-butyl-4-chloro-5-formylimidazol-1-yl)methyl]-9,10-dihydro-9,10-ethano-11,12-bis (1H-tetrazol-5-yl)anthracene (±)-11S,12S-trans-2-[(2-n-butyl-4-chloro-5-formylimidazol-1-yl) methyl]-9,10-dihydro-9,10-ethano-11,12-bis (1H-tetrazol-5-yl)anthracene (±)-trans-2-[(2-n-butyl-4-phenylthio-5-formylimidazol-1-yl)methyl]-9,10-dihydro-9,10-ethano-11,12-his (1H-tetrazol-5-yl)anthracene endo-(±)-cis-2-[(2-n-butyl-4-chloro-5-formylimidazol-1-yl)methyl]-9,10-dihydro-9,10-ethano-11,12-(cyclobut-1,2-yl)-11-(1H-tetrazol-5-yl)-12-(cyano)anthracene exo-(±)-cis-2-[(2-n-butyl-4-chloro-5-formylimidazol-1-yl)methyl]-9,10-dihydro-9,10-ethano-11,12-(cyclobut-1,2-yl)-11-(1H-tetrazol-5-yl)-12-(cyano)anthracene endo-(±)-cis-2-[(2-n-butyl-4-chloro-5-formylimidazol-1-yl)methyl]-9,10-dihydro-9,10-ethano-11,12-(cyclobut-1,2-yl)-11-(cyano)-12-(1H-tetrazol-5-yl) anthracene exo-(±)-cis-2-[(2-n-butyl-4-chloro-5-formylimidazol-1-yl)methyl]-9,10-dihydro-9,10-ethano-11,12-(cyclobut-1,2-yl)-11-(cyano)-12-(1H-tetrazol-5-yl)anthracene (±)-12R-2-[(2-n-butyl-4-chloro-5-formylimidazol-1-yl)methytl]-9, 10-dihydro-9,10-ethano-11,11-bistrifluoromethy10-12-cyano-12-(1H-tetrazol-5-yl)anthracene (±)-12S-2-[(2-n-butyl-4-chloro-5-formylimidazol-1-yl)methytl]-9,10-dihydro-9,10-ethano-11,11-bistrifluoromethyl10-12-cyano-12-(1H-tetrazol-5-yl)anthracene (±)-11R-2-[(2-n-butyl-4-chloro-5-formylimidazol-1-yl)methyl]-9, 10-dihydro-9,10-ethano- 12, 12-bistrifluoromethyl-11-cyano-11- (1H-tetrazol-5-yl)anthracene (±)-11S-2-[(2-n-butyl-4-chloro-5-formylimidazol-1-yl)methyl]-9,10-dihydro-9,10-ethano-12,12-bistrifluoromethyl-11-cyano-11-(1H-tetrazol-5-yl)anthracene (±)-11S-2-[(2-n-butyl-4-chloro-5-formylimidazol-1-yl)methyl]-9,10-dihydro-9,10-ethano-11-carboxy-11-(carboxymethyl)anthracene (±)-11R-2-[(2-n-butyl-4-chloro-5-formylimidazol-1-yl)methyl]-9,10-dihydro-9,10-ethano-11-carboxy-11-(carboxymethyl)anthracene (±)-12S-2-[(2-n-butyl-4-chloro-5-formylimidazol-1-yl)methyl]-9,10-dihydro-9,10-ethano-12-carboxy-12-(carboxymethyl)anthracene (±)-12R-2-[(2-n-butyl-4-chloro-5-formylimidazol-1-yl)methyl]-9,10-dihydro-9,10-ethano-12-carboxy-12-(carboxymethyl) anthracene.

Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in *Remington's Pharmaceutical Sciences*, 17th Edition, p. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a compound of formula I, and methods of using the compounds of formula I to treat hypertension and congestive heart failure. The pharmaceutical compositions can optionally contain one or more other therapeutic agents, such as a diuretic or a non-steroidal anti-inflammatory drug. Also within the scope of this invention is a method of preventing renal failure resulting from administration of a nonsteroidal anti-inflammatory drug (NSAID) which comprises administering a compound of formula I in stepwise or physical combination with the NSAID. The compounds of this invention can also be used as diagnostic agents to test the renin angiotensin system.

It should be noted in the foregoing structural formula, when a radical can be a substituent in more than one previously defined radical, that first radical can be selected independently in each previously defined radical. For example, R¹, R², R³ and R⁴ can each be CONHOR¹⁴. R¹⁴ need not be the same substituent in each of R¹, R², R³ and R⁴ but can be selected independently for each of them.

DETAILED DESCRIPTION

Synthesis

The novel compounds of formula I may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformations proposed. This will frequently necessitate judgment as to the order of synthetic steps, protecting groups required, deprotection conditions, and activation of a benzylic position to enable attachment to nitrogen on the heterocyclic nucleus. Throughout the following section, not all compounds of formula I falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

methylsulfoxide (DMSO) at 20° C. to the reflux temperature of the solvent for 1-10 hours.

As $R^7$ and $R^8$ are different, mixtures of two regioisomer alkylation products 3b and 3c are obtained in which $R^7$ and $R^8$ are interchanged. When $R^8$ is CHO the alkylation is such that the arylmethyl group becomes attached to the adjacent nitrogen preferentially. These isomers possess distinct physical and biological properties and can usually be separated and isolated by conventional separation techniques such as chromatography and/or crystallization.

Alternatively, any properly functionalized arylme-

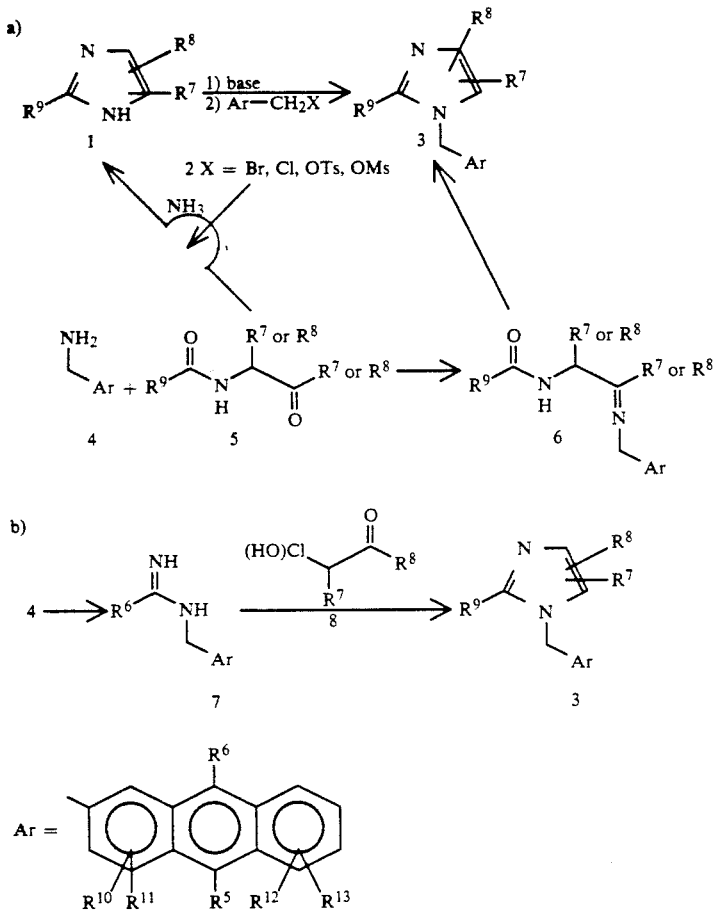

Generally, compounds of formula 3 can be prepared by direct alkylation onto imidazole 1, with an appropriately protected arylmethyl halide, tosylate or mesylate 2 in the presence of base, as shown in path a). Preferably, the metallic imidazolide salt is prepared by reacting imidazole 1 with a proton acceptor such as MH where M is lithium, sodium or potassium in a solvent such as dimethylformamide (DMF) or by reacting it with a metal alkoxide of formula MOR where R is methyl, ethyl, t-butyl or the like in an alcohol solvent such as ethanol or t-butanol, or a dipolar aprotic solvent such as DMF. The imidazole salt is dissolved in an inert aprotic solvent such as DMF, and treated with an appropriate alkylating agent 2. Alternatively, imidazole 1 can be alkylated with an arylmethyl halide (2; where X=Br, Cl) in the presence of a base such as sodium carbonate, potassium carbonate, triethylamine or pyridine. The reaction is run in an inert solvent such as DMF or dithylamine derivative 4 may be converted to imine 6 by treatment with an acylamino ketone 5 in the presence of an inert solvent such as benzene, toluene, or the like, and a catalytic amount of p-toluenesulfonic acid or molecular sieves, N. Engel, and W. Steglich, *Liebigs Ann. Chem.*, 1916 (1978), or in the presence of alumina, F. Texier-Boulet, *Synthesis*, 679 (1985). The resulting imine 6 can be cyclized to the N-arylmethyl imidazole 3 with phosphorus pentachloride (PCl$_5$) phosphorus oxychloride (POCl$_3$) or triphenylphosphine (PPh$_3$) in dichloroethane in the presence of a base such as triethylamine, N Engel and W Steglich, *Liebigs Ann Chem.*, 1916 (1978).

Acylamino ketone 5 is readily obtainable from amino acids via the Dakin-West reaction, H. D. Dakin, R. West, *J. Biol. Chem.*, 78, 95 and 745 (1928), and various modifications thereof, W. Steglich, G. Hofle, *Angew. Chem. Int. Ed. Engl.*, 8, 981 (1969); G. Hofle, W. Steglich, H. Vorbruggen, *Angew. Chem. Int. Ed. Engl.*, 17, 569 (1978); W. Steglich, G. Hofle, *Ber.*, 102, 883 (1969), or by selective reduction of acyl cyanides, A. Pfaltz, S. Anwar, *Tet. Lett.*, 2977 (1984), or from α-halo, α-tosyl or α-mesyl ketones via the appropriate substitution reactions that one skilled in the art will readily recognize.

The functionalized arylmethylamines 4 may be made from the corresponding arylmethyl halide, tosylate or mesylate 2 via displacement with a nitrogen nucleophile, a procedure familiar to one skilled in the art. This displacement may be achieved using azide ion, ammonia, or phthalimide anion, etc., in a neutral solvent such as dimethylformamide, dimethylsulfoxide etc., or under phase transfer conditions. The arylmethyl halide 2 may be made by a variety of benzylic halogenation methods familiar to one skilled in the art, for example benzylic bromination of toluene derivatives with N-bromosuccinimide in an inert solvent such as carbon tetrachloride in the presence of a radical initiator such as benzoyl peroxide at temperatures up to reflux conditions.

A wide variety of anthracene derivatives may be made from simple electrophilic substitution reactions on an aromatic ring. This includes nitration, sulfonation, phosphorylation, Friedel-Crafts alkylation, Friedel-Crafts acylation, halogenation, and other similar reactions known to one skilled in the art, G. A. Olah, *Friedel-Crafts and Related Reactions*, Vol. 1–5 Interscience, NY (1965).

Another way to synthesize functionalized arylmethyl halides is via chloromethylation of the corresponding aromatic precursor. Thus, the appropriately substituted anthracene may be chloromethylated with formaldehyde and hydrochloric acid (HCl) for example with or without an inert solvent such as chloroform, carbon tetrachloride, light petroleum ether or acetic acid. A Lewis acid such as zinc chloride ($ZnCl_2$) or a mineral acid such as phosphoric acid may also be added as a catalyst or condensing agent, R. C. Fuson, C. H. McKeever, *Org. Reactions*, 1, 63 (1942).

Alternatively, N-arylmethylimidazoles 3 can also be prepared as shown in path b) by forming an $R^6$ substituted amidine 1 from an appropriately substituted arylmethylamine 4 which is in turn reacted with an α-haloketone, α-hydroxyketone 8, α-halo-aldehyde, or α-hydroxyaldehyde, F. Kunckell, *Ber.*, 34, 637 (1901).

The starting imidazole compounds 1 are readily available by any of a number of standard methods. For example, acylaminoketone 5 can be cyclized with ammonia or equivalents thereof, D. Davidson, et al., *J. Org. Chem.*, Z, 319 (1937) to the corresponding imidazole as shown in Scheme 1. The corresponding oxazole can also be converted to imidazole 1 by action of ammonia or amines in general, H. Bredereck, et al., *Ber*, 88, 1351 (1955); J. W. Cornforth and R. H. Cornforth, *J. Chem Soc.*, 96 (1947).

Several alternative routes to imidazoles 1 are illustrated in Scheme 2. As shown in Scheme 2 equation a), reaction of the appropriate $R^9$ substituted imidate esters 9 with an appropriately substituted α-hydroxy- or α-haloketone or aldehyde 8 in ammonia leads to imidazoles of formula 1, P. Dziuron, and W. Schunack, *Archiv. Pharmaz.*, 307 and 470 (1974).

The starting imidazole compounds 1 wherein $R^7$ and $R^8$ are both hydrogen can be prepared as shown in equation b) by reaction of the appropriate R9-substituted imidate ester 9 with α-amino-acetaldehyde dimethyl acetal 10, M. R. Grimmett, *Adv. Heterocyclic Chem.*, 12, 103 (1970).

As shown in equation c), imidazole 12; wherein $R^7$ =hydrogen and $R^8=CH_2OH$ can be prepared by treatment of the imidate ester 9 with 1,3-dihydroxy-acetone 11 in ammonia by the procedure described in *Archive der Pharmazie*, 307, 470 (1974). Halogenation of imidazole 12 or any imidazole wherein $R^7$ or $R^8$ is hydrogen is preferably accomplished by reaction with one to two equivalents of N-halosuccinimide in a polar solvent such as dioxane or 2-methoxyethanol at a temperature of 40°–100° C. for 1–10 hours Reaction of the halogenated imidazole 13 with an arylmethylhalide % in the manner described in Scheme 1 affords the corresponding N-arylmethylimidazole 14; wherein $R^7$ is halogen and $R^8$ is $CH_2OH$. This procedure is described in U.S. Pat. No. 4,355,040. Alternatively, imidazole 14 can be prepared by the procedure described in U.S. Pat. No. 4,207,324.

Compounds of formula 14 can also be prepared by treatment of the starting imidazole compound 1 wherein $R^7$ and $R^8$ are both hydrogen, with the appropriate arylmethyl halide followed by functionalization of $R^7$ and $R^8$ by treatment with formaldehyde as described in E. F. Godefroi, et al., *Recueil*, 91, 1383 (1972) followed by halogenation as was described above.

As shown in equation d) the imidazoles 1 can also be prepared by reaction of $R^9$ substituted amidines 15 with an α-hydroxy- or α-haloketone or aldehyde 8 as described by F. Kunckel, *Ber.*, 34, 637 (1901).

Compounds of formula I wherein $R^8=CH_2OH$ can be prepared as shown in equation e). The imidazoles 1 were prepared as described in L. A. Reiter, *J. Org. Chem.*, 52, 2714 (1987). Hydroxymethylation of 1 as described by U. Kempe, et al. in U.S. Pat. No. 4,278,801 provides the hydroxymethylimidazoles 1a.

Scheme 2

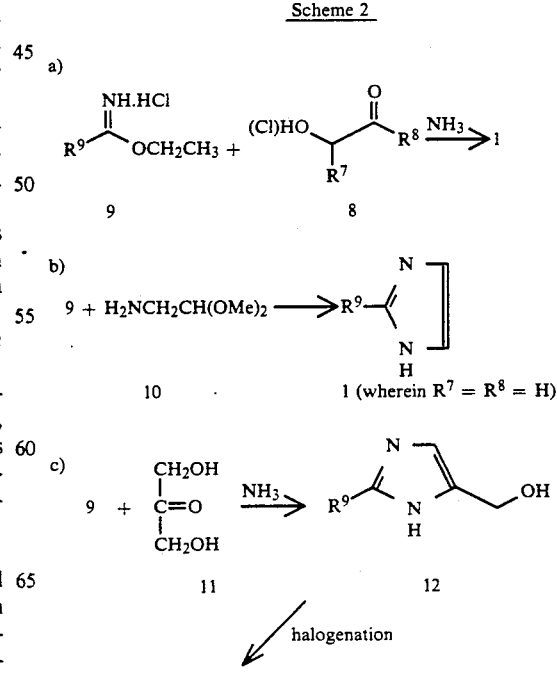

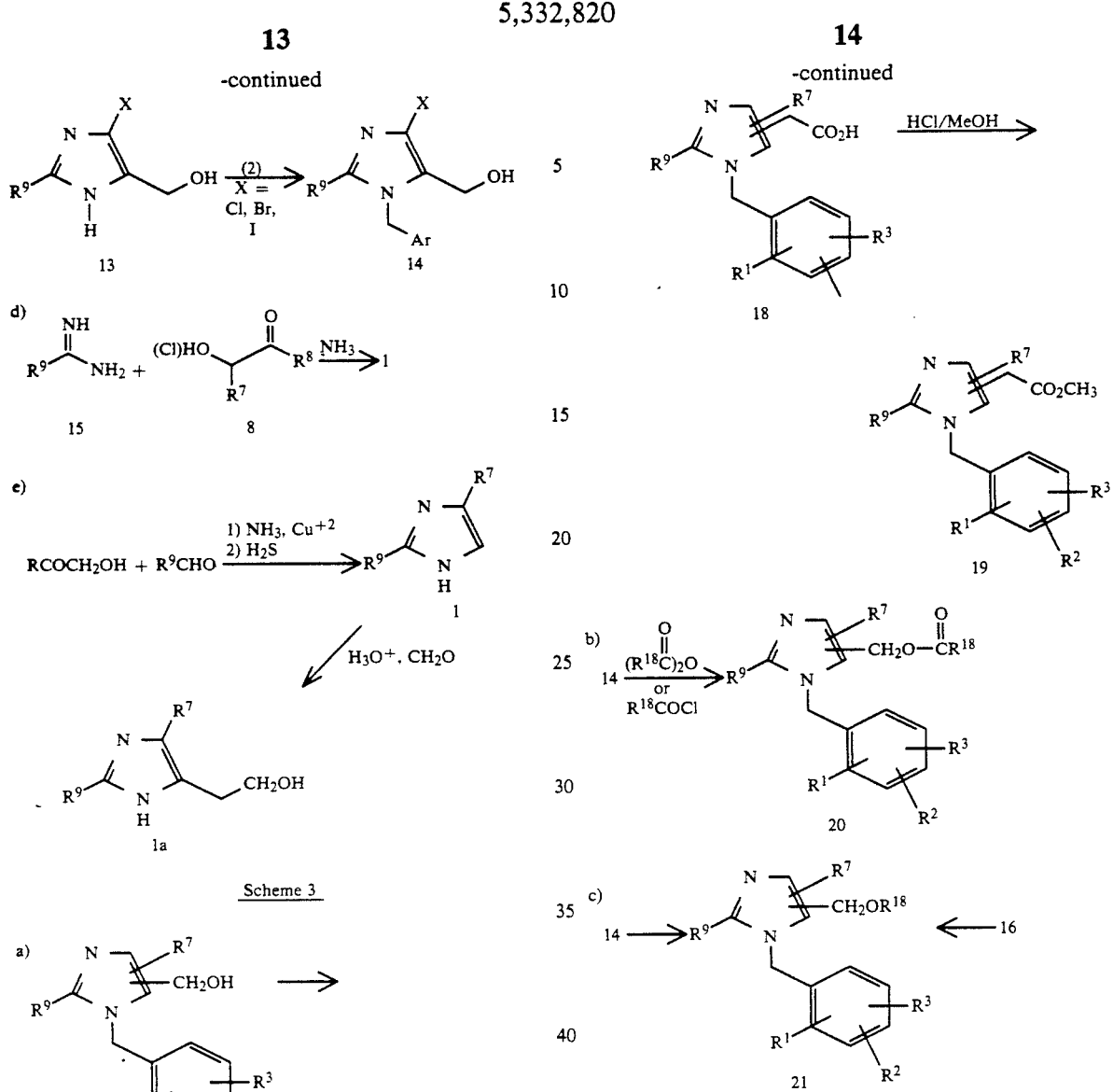

As shown in Scheme 3, path a) for arylmethylimidazoles 14 where $R^8=CH_2OH$, the hydroxymethyl groups may be easily converted to the corresponding halide, mesylate or tosylate by a variety of methods familiar to one skilled in the art. Preferably, the alcohol 14 is converted to the chloride 16 with thionyl chloride in an inert solvent at temperatures of 20° C. to the reflux temperature of the solvent.

Chloride 16 may be displaced by a variety of nucleophiles by nucleophilic displacement reaction procedures familiar to one skilled in the art. For example, excess sodium cyanide in DMSO may be used to form cyanomethyl derivatives 17 at temperatures of 20° C to 100° C.

Nitrile 17 may be hydrolyzed to an acetic acid derivative 18, by a variety of methods. Examples of desired acids and bases for this hydrolysis include mineral acids such as sulfuric acid, hydrochloric acid, and mixtures of either of the above with 30-50% acetic acid (when solubility is a problem), and alkali metal hydroxides such as sodium hydroxide or potassium hydroxide. The hydrolysis reaction proceeds under heating at temperatures ranging from 50°-160° C. for 2-48 hours. Carboxylic acid 18 may be esterified by a variety of methods without affecting other parts of the molecule. Preferably, 18 is refluxed in a hydrochloric acid/methanol solution for 2-48 hours to give ester 19.

Ester 19 may be hydrolyzed to carboxylic acid 18. Various methods, acidic or basic, may be used. For example, compound 19 is stirred with 0.5 N potassium hydroxide in methanol, or if base soluble, it is stirred in 1.0 N sodium hydroxide for 1-48 hours at 20° C. to reflux temperatures.

Hydroxymethyl derivative 14 may be acylated to give 20 by a variety of procedures. As shown in path b) acylation can be achieved with 1-3 equivalents of an acyl halide or an anhydride in a solvent such as diethyl ether, tetrahydrofuran, methylene chloride or the like in the presence of a base such as pyridine or triethylamine. Alternatively 14 may be acylated by reaction with a carboxylic acid and dicyclohexylcarbodiimide (DCC) in the presence of a catalytic amount of 4-(N,N-dimethylamino)pyridine (DMAP) via the procedure described by A. Hassner, *Tet. Lett.*, 46, 4475 (1978). Treatment of 14 with a solution of carboxylic acid anhydride in pyridine optionally with a catalytic amount of DMAP at temperatures of 20°-100° C. for 2-48 hours is the preferred method.

The ether 21 can be prepared from the alcohol 14 as shown in path c) by methods such as treatment of 14 in a solvent such as DMF or DMSO with potassium t-butoxide, sodium hydride, or the like followed by treatment with $R^{18}L$ at 25° C. for 1-20 hours, where L is a halogen, tosylate or mesylate.

Alternatively, treatment of 14 with 1-5 equivalents of thionyl chloride in chloroform for 2-6 hours at 25° C. followed by treatment of the intermediate 16 with 1-3 equivalents of $MOR^{18}$ where M is sodium or potassium, for 2-10 hours at 25° C. either in $R^{18}OH$ as solvent or in a polar solvent such as DMF or the like will also yield ether 21.

The ether 21 can also be prepared for example by heating 14 for 3-15 hours at 60°-160° C. in $R_{18}OH$ containing an inorganic acid such as a hydrochloric acid or sulfuric acid.

Compounds where $R^1$, $R^2$, $R^3$, $R^4$, $R^{10}$, $R^{11}$, $R^{12}$ or $R^{13}$ are —$CONHOR^{14}$ may be prepared as shown in Scheme 4, by the treatment of a carboxylic acid 22 with 1-4 equivalents of thionyl chloride for 1-10 hours. This reaction can be run without solvent or in a nonreactive solvent such as benzene or chloroform at temperatures of 25°-26° C. The intermediate acid chloride is then treated with 2-10 equivalents of the appropriate amine derivative, $H_2N$-$OR^{14}$, for 2-18 hours at temperatures of 25°-80° C. in a polar aprotic solvent such as tetrahydrofuran or DMSO to give the hydroxamic acid 23.

Scheme 4

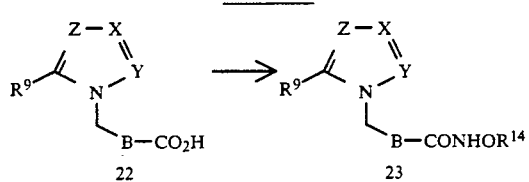

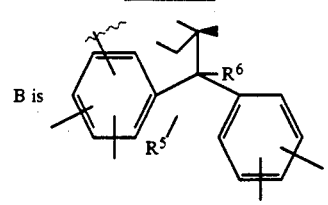

where $CONHOR^{12}$ may be attached at any of the above specified positions except

Alternatively, the carboxylic acid 10 can be converted to the hydroxamic acid 23 according to the procedure in *J. Med. Chem.*, 28, 1158 (1985) by employing dicyclohexylcarbodiimide, 1-hydroxybenzotriazole, and $H_2NOR^{14}$ or according to the procedure described in *Synthesis*, 929 (1985) employing the Vilsmeier reagent and $H_2NOR^{14}$.

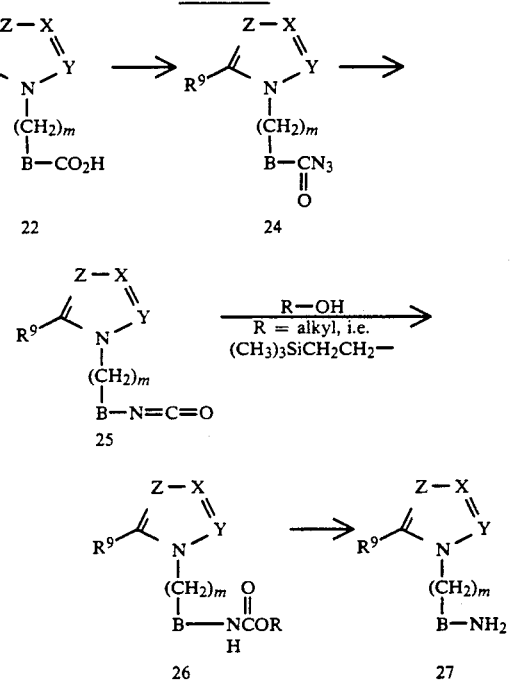

Amino intermediates 27 may be obtained from the corresponding nitro compound precursor by reduction. A variety of reduction procedures may be used such as iron/acetic acid. D. C. Owsley, J. J. Bloomfield, *Synthesis*, 118 (1977), stannous chloride, F. D. Bellamy, *Tet. Lett.*, 839 (1984) or careful hydrogenation over a metal catalyst such as palladium or platinum.

As shown in Scheme 5, amino intermediates of N-arylmethylimidazoles may also be prepared from the corresponding carboxylic acid 22 or acid chloride via Curtius rearrangement of an intermediate acyl azide 24. More modern methods include using diphenylphosphoryl azide as a source of azide, T. Shioiri, K. Ninomiya, S. Yamada, *J. Am. Chem. Soc.*, 94, 6203 (1972), and trapping the intermediate isocyanate 22 produced by the Curtius rearrangement with 2-trimethylsilylethanol and cleaving the resultant carbamate 26 with fluoride to liberate the amine 27, T. L. Capson and C. D. Poulter, Tet. Lett., 25, 3515 (1984). Classical procedures familiar to one skilled in the art may also be employed.

Amino derivatives where $R^1$, $R^2$, $R^3$, $R^4$, $R^{10}$, $R^{11}$, $R^{12}$ or $R^{13}$ are —$NH_2$ may be converted into their trifluoromethanesulfonamide derivative preferably by reacting it with triflic anhydride and a base such as triethylamine in an inert solvent such as methylene chloride at −78° C. followed by warming to room temperature.

Tetrazoles 33 where

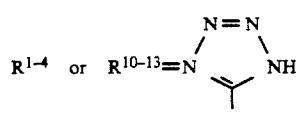

can be prepared from the nitrile precursors ($R^{1-4}$ or $R^{10-13}$=CN) by the methods described in Scheme 16. Compounds 29 may be prepared by the 1,3-dipolar cycloaddition of trialkyltin or triphenyltin azides to the appropriately substituted nitrile 28. Alkyl is defined as normal alkyl of 1–6 carbon atoms and cyclohexyl. An example of this technique is described by S. Kozima, et al., J. Organometallic Chemistry, 337 (1971). The required trialkyl or triaryltin azides are made from the requisite commercial trialkyl or triaryl tin chloride and sodium azide. The trialkyl or triaryltin group is removed via acidic or basic hydrolysis and the tetrazole can be protected with the trityl group by reaction with trityl chloride and triethylamine to give 30. Deprotection of the trityl group via hydrolysis affords 31; $R^{1-4}$ $R^{10-13}$ =tetrazole. Other protecting groups such as p-nitrobenzyl and 1-ethoxyethyl can be used instead of the trityl group to protect the tetrazole moiety. These groups as well as the trityl group can be introduced and removed by procedures described in Greene, Protective Groups in Organic Synthesis, Wiley-Interscience, (1980). A more classic procedure for converting nitriles into tetrazoles is shown in line 6 (Scheme 6). Here contact of nitrile 32 with a mixture of sodium azide and ammonium chloride in DMF at room temperature to 120° C. yields tetrazole 33 (W. G. Finnegan; R. A. Henry, R. Lofquist, J. Am, Chem. Soc., 80, 3908 (1958)).

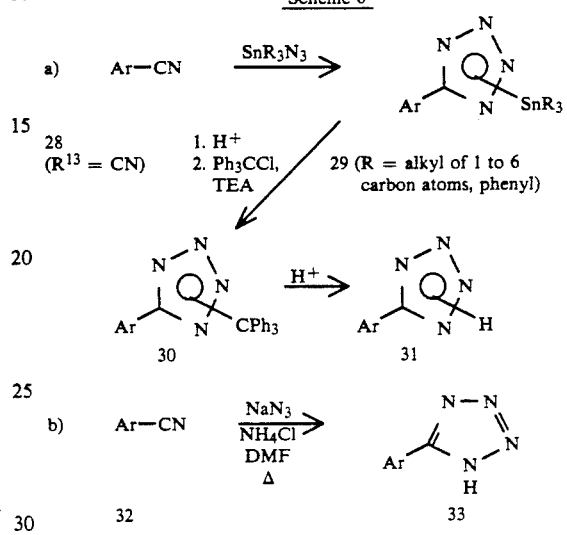

Scheme 6

Pertinent $R^9$ groups may be variously introduced by many procedures including those described in Scheme 7 which describes imidazole construction.

the $R^9$ groups so introduced may stand unchanged or may be further elaborated if appropriately functionalized, according to methods familiar to those skilled in the art such as are illustrated in Scheme 7.

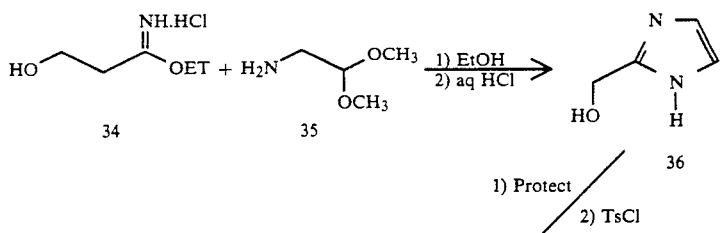

Scheme 7

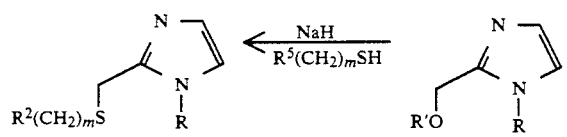

R = $CPh_3$, $SO_2Ph$, $CH_3CHOC_2H_5$
38: R' = H        39: R' = Ts

PDC

Scheme 7

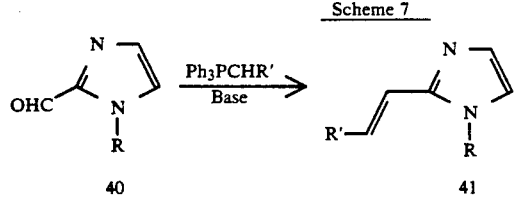

In Scheme 8, the 2-alkenylanalogues 44 can be prepared by bromination of the 2-alkyl derivatives 42 followed by elimination of hydrogen bromide. The bromination is preferably accomplished by UV-irradiation for 1-4 hours of imidazole 42 and N-bromosuccinimide, in an inert solvent, such as carbon tetrachloride at 25° C. Treatment of the intermediate bromide 43 with a base, such as DBU, triethylamine, or potassium t-butoxide, affords the trans 2-alkenyl compounds 44. Cis alkenyl derivatives 46 are prepared from the trans alkenyl compounds by treatment with osmium tetroxide and sodium periodate to afford aldehydes 45 followed by Wittig reaction.

Scheme 8

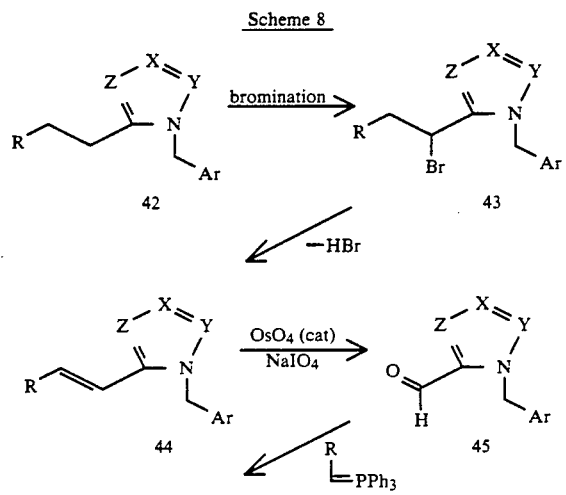

R = alkyl, cycloalkyl

Alternatively, $R^9$ groups may be introduced by metallation of a protected imidazole or protected 2-methylimidazole followed by addition of an appropriate electrophile as illustrated in Scheme 9, equations a) and b). The products (alcohols, esters, halides, aldehydes, alkyls) are suitable for further elaboration by methods familiar to those skilled in the art. Metallation of imidazoles is described in K. L. Kirk, *J. Org. Chem.*, 43, 4381 (1978); R. J. Sundberg, *J. Her. Chem.*, 14, 517 (1977); J. V. Hay, et al., *J. Org. Chem.*, 38, 4379 (1973); B. Iddon, *Heterocycles*, 23, 417 (1985).

Condensation of 2-methylimidazole and appropriate electrophiles (equation b)) with catalytic acid or base as described in A. R. Katritzky (Ed.), *Comprehensive Heterocyclic Chemistry*, Vol. 5, p. 431, Pergamon Press, NY (1984) affords products wherein $R^9$ is alkenyl which are suitable for further elaboration.

Scheme 9

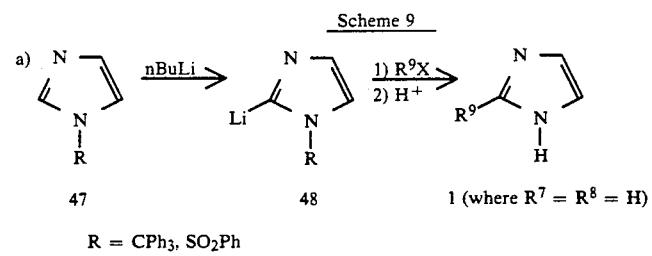

R = CPh₃, SO₂Ph

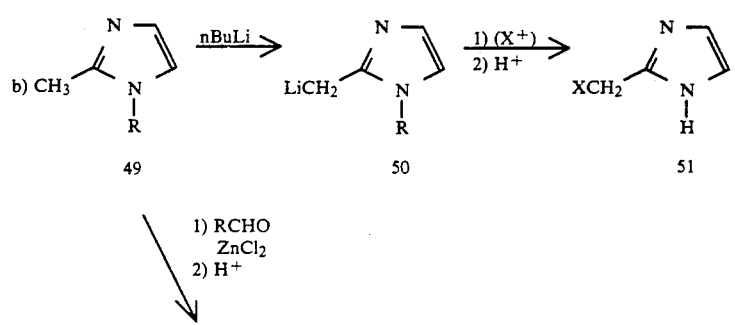

Scheme 9

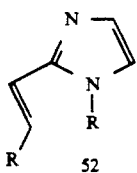

52

Various 2-substituted imidazoles can be prepared by reaction of a protected 2-trimethylsilylimidazole with a suitable electrophile by the method described by F. H. Pinkerton and S. F. Thames, *J. Het. Chem.*, 9, 67 (1972), which can be further elaborated as desired. Alternatively, $R^9$ may also be introduced by nickel catalyzed cross-coupling of Grignard reagents with 2-(methylthio)imidazoles (Scheme 10) as described by E. Wenkert and T. W. Ferreira, *J. Chem. Soc.; Chem. Commun.*, 840 (1982); E. Wenkert et al., *J. Chem. Soc., Chem. Commun.*, 637 (1979); and H. Sugimura and H. Takei, *Bull. Chem. Soc. Japan*, 58, 664 (1985). The 2-(methylthio) imidazoles can be produced by the procedure described in German Patent No. 2,618,370 and the references cited therein.

Scheme 10

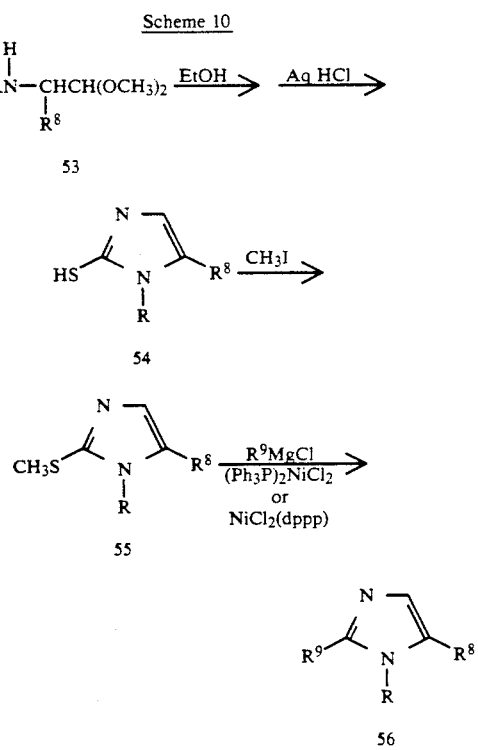

As shown in Schemes 1.1-13, elaboration of $R^8$ can be accomplished by some of the procedures described in Schemes 3 and 1, by chain extension reactions familiar to those skilled in the art, or by degradation reactions such as conversion of an ester to an acid or an alkene to an aldehyde.

Specifically, the hydroxymethyl group can be activated for the displacement reaction by reacting with thionyl chloride, $PCl_5$ or with carbon tetrachloride/triphenylphosphine to form a corresponding chloro derivative. By a similar reaction bromo and iodo derivatives can be obtained. The hydroxymethyl group can also be activated by forming the corresponding p-toluenesulfonate, methanesulfonate and trifluoromethanesulfonate derivatives.

The hydroxymethyl group on compound 14 can be readily oxidized to an aldehyde group by means of manganese dioxide or ceric ammonium nitrate. The aldehyde group will enter into typical carbon-carbon bond forming reactions with Grignard and lithium reagents as well as with compounds bearing activated methylene groups. Alternatively, the hydroxymethyl group can be oxidized directly to an acid functionality which can in turn be converted to ester and amide derivatives. The esters and amides can be prepared directly from the aldehydes by manganese dioxide oxidation in the presence of sodium cyanide and an alcohol or amine, *J. Am. Chem. Sec.*, 90, 5616 (1968) and *J. Chem. Soc*, (C), 2355 (1971).

As shown in Scheme 11, the chlorine on compound 16 can be displaced by the anion of dialkyl malonate to give the corresponding malonate derivative 57. The saponification of 57 with NaOH (or KOH) gives the corresponding diacid which can be decarboxylated to give the corresponding propionic acid derivative 58 by heating to 120° C. Alternatively, 58 can be directly obtained by refluxing 57 with a mineral acid such as HCl or sulfuric acid. The free acid 58 can be esterified by heating in a medium of the various alcohols and a catalytic amount of mineral acids such as HCl or sulfuric acid to give the corresponding esters 59. Alternatively the esters can be obtained by reacting the free acid 58 and the corresponding alcohols in the presence of coupling reagents such as 2,3-dichloro-5,6-dicyanobenzoquinone (DDQ) or 2-ethoxy-1-(2H)-quinolinecarboxylic acid, ethyl ester (EEDQ). A similar reaction with various mono-substituted and disubstituted amines produces the corresponding amides 60.

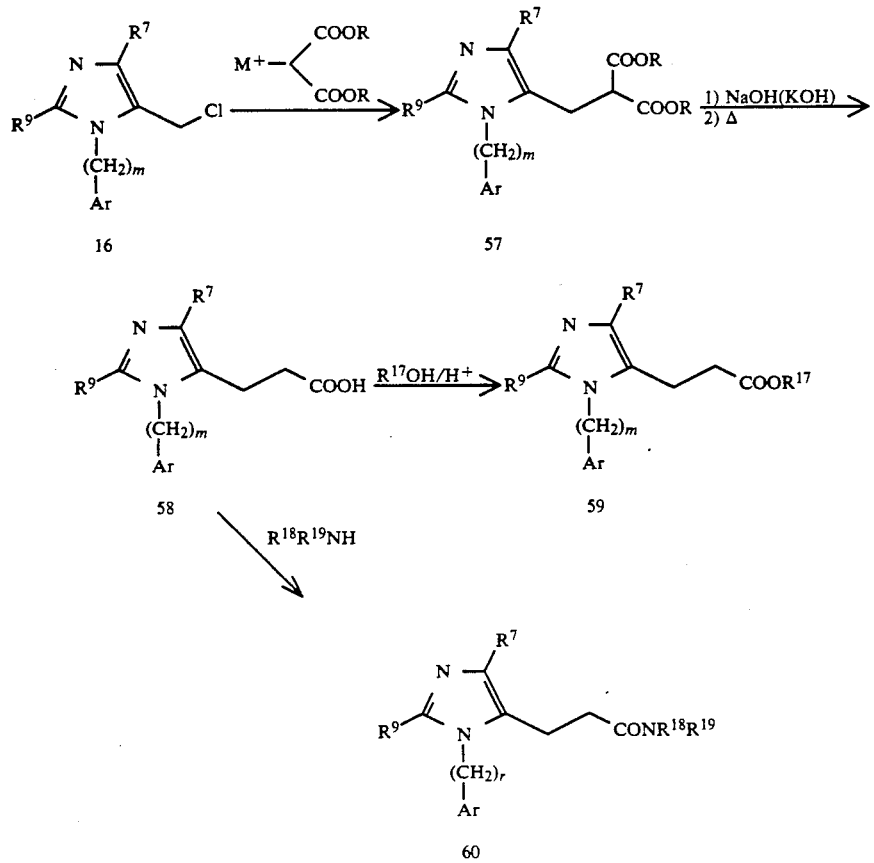

The reaction between the thiopyridyl ester 61 and a suitable Grignard reagent produces the ketones 62.

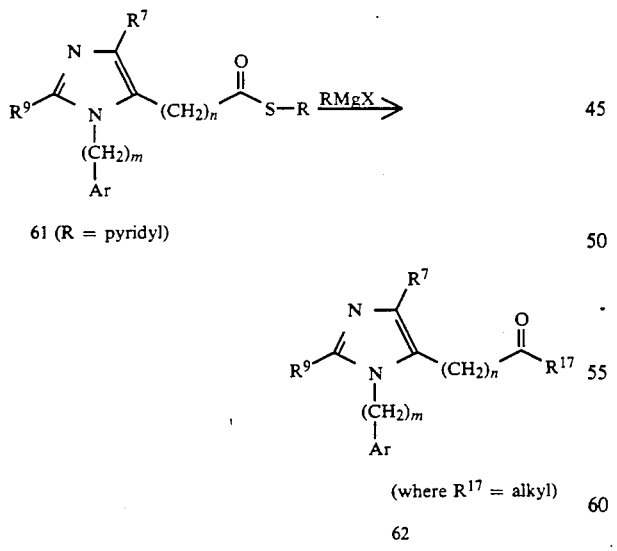

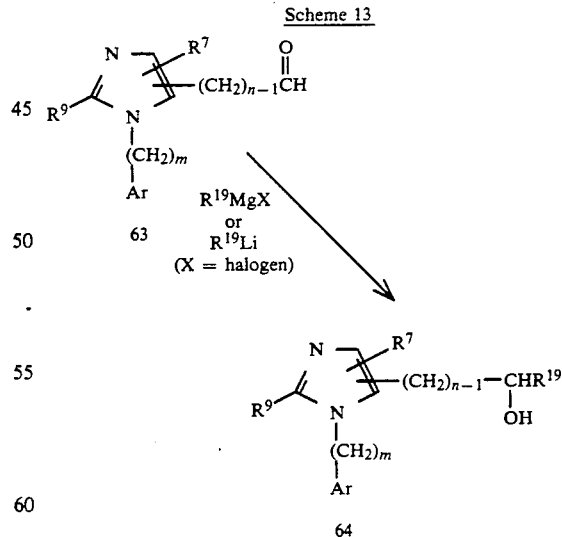

As shown in Scheme 13 when the imidazole 4- and/or 5-position contains an aldehyde 63 then reaction with organometallic reagents such as Grignard or alkyl-/aryllithium reagents will yield alcohols 64 which in turn may be transformed into a variety of other functionality familar to one skilled in the art.

As shown in Scheme 14, ester 66 may be obtained by direct oxidation of aldehyde 65 with NaCN, $MnO_2$ in methanol (E. J. Corey, et al., *J. Am. Chem. Soc.*, 90, 5616 (1968)). Oxidation of 65 with NaCN, $MnO_2$, and an amine in 2-propanol leads to the corresponding amide 67 (N. W. Gilman, *Chem. Comm.*, 733 (1971)).

Scheme 14

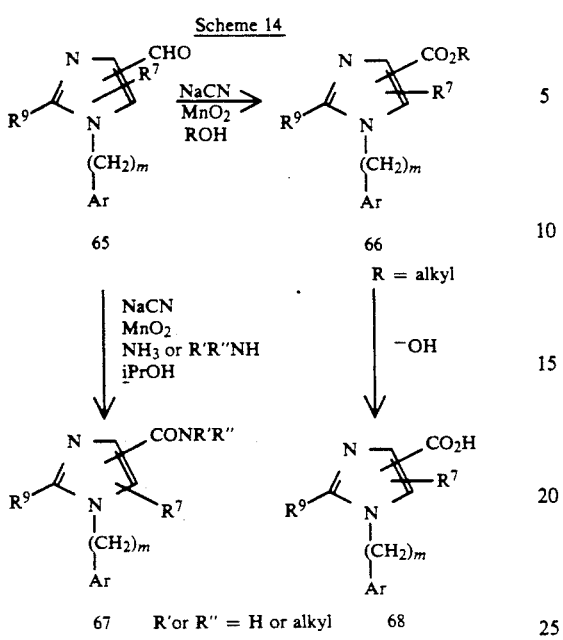

Saponification of ester 66 will lead to carboxylic acid 68.

Aldehyde 65, in turn, may be made from the corresponding alcohol 14 by a variety of methods familiar to one skilled in the art, including pyridium chlorochromate (PCC), Swern and ceric ammonium nitrate (CAN) oxidations.

Likewise, the unalkylated hydroxymethylimidazole derivative 1($R^8$=$CH_2OH$) may undergo the transformations to the aldehyde, ester, carboxylic acid and carboxamide by the reactions mentioned above for the alkylated case.

Compounds 70 (where Ar'=aryl or heteroaryl as described in the scope under the definition of $R^7$) can be prepared by the coupling of an arylmetal derivative (At'M, where M=ZnBr, Me$_3$Sn, B(OH)$_2$, etc.) with a haloimidazole 69 in the presence of a transition metal catalyst such as palladium, nickel, platinum, zirconium, etc. (Scheme 15a). Alternatively, an imidazole metal derivative 71 can be coupled to an arylhalide to prepare 70 (Scheme 15b).

The arylmethyl derivatives 72 can be prepared employing the transition metal catalysed coupling of 69 and an arylmethylmetal (Ar'CH$_2$M' where M'=ZnBr, etc.), as shown in Scheme 15c.

Compounds 73 may be prepared, as described in Scheme 15d by the coupling of an alkenyl or alkynyl metal derivative (AM) or the corresponding alkene or alkyne (AH) with 69.

Likewise, the unalkylated imidazoles (1, where $R^7$ Br or I) may undergo the coupling reactions described in Scheme 15a-d [For references to transition metal catalyzed coupling reactions, see Richard C. Heck, *Palladium Reagents in Organic Synthesis*, Academic Press, NY, Chapters 6, 7 and 8; and references cited therein].

The compounds of formula I where $R^7$ is an phenylalkenyl group or an phenylalkynyl group and the carbon-carbon double or triple bond is not adjacent to the imidazole ring (e.g., $R^7$=(CH$_2$)$_u$CH=CH(CH$_2$)$_v$Ar, where u≠0 and v=0, 1,2, . . . ) can be prepared by a variety of chain elongation methods and chain coupling reactions known to one skilled in the art including those described in Schemes 3, 7, 8, 11, 12, 13, and 15.

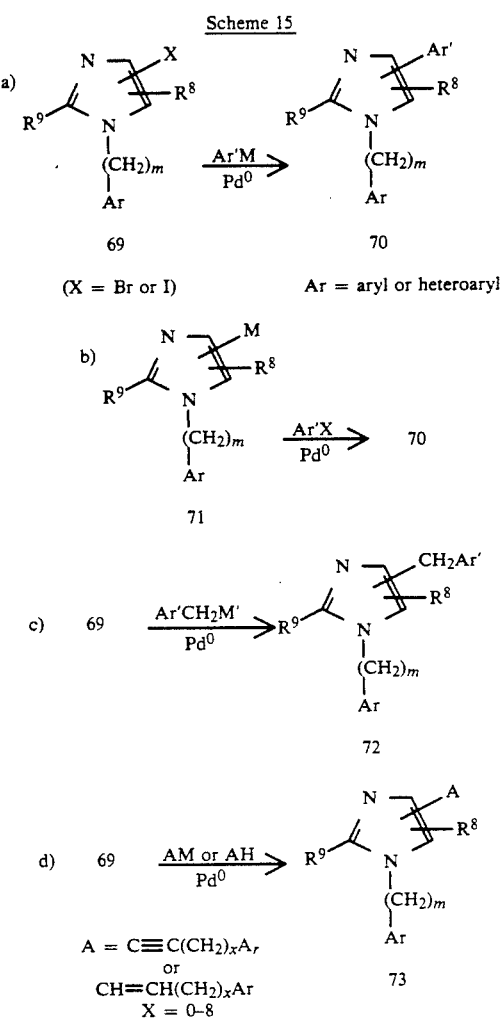

Compounds of formula I where $R^7$=arylalkenyl and $R^8$=$CH_2OH$, aldehyde, or COOH can be prepared as shown in Scheme 16.

2-Alkylimidazole-4,5-dicarboxylic acids 74, prepared by the method of R. G. Fargher and F. L. Pyman (*J. Chem. Soc.*, 115, 217 (1919)), can be converted into their corresponding diesters 75 by simply refluxing in an alcohol solvent in the presence of an acid such as HCl, or by many other methods familiar to one skilled in the art.

Diester 75 can then be converted into its metallic salt by reaction with sodium methoxide, sodium ethoxide, sodium hydride, potassium hydride or any other base in an appropriate solvent such as DMF. The resultant salt is then alkylated with the appropriately substituted arylmethyl derivative 2 to yield imidazole 76. The above alkylation sequence may be also performed by heating or refluxing the arylmethyl halide (tosylate or mesylate) 2 with imidazole 75 in a solvent such as DMF in the presence of an acid scavenger such as potassium or sodium carbonate.

Diester 76 can be reduced with lithium aluminum hydride in an inert solvent such as tetrahydrofuran (THF) to the corresponding dialcohol 77. Selective oxidation of dialcohol 77 with manganese dioxide in an inert solvent such as THF yields primarily aldehyde 79 with a minor product dialdehyde 78. Separation of 79 from 78 either by crystallization or chromatographically, followed by Wittig reaction of 79 with the appropriately substituted arylalkylidenetriphenylphosphorane in an inert solvent such as THF yields the 4-arylalkenyl-5-hydroxymethylimidazole Ea. Further oxidation of 80 with the Dess-Martin periodinane (*J. Org.. Chem.*, 48, 4155 (1983)), with manganese dioxide, with pyridinium chlorochromate, with barium manganate or with other oxidants familiar to one skilled in the art, in an inert solvent such as THF or methylene chloride yields the 4-arylalkenylimidazole-5-carboxaldehyde 81.

Oxidation of 81 with, for example, manganese dioxide/cyanide ion (E. J. Corey, et al., *J. Am. Chem, Soc.,* 90, 5616 (1968)) or with potassium permanganate (D. J. Sam, et al., *J. Am. Chem. Soc.,* 94, 4024 (1972)) yields 4-arylalkenylimidazole-5-carboxylic acid 82.

Most of the major reaction pathways leading to 1,2,3-triazoles involve azides and several reviews have been published in this area, G L'abbe', *Chem Rev.,* 69, 345 (1969); T. Srodsky, in *The Chemistry of the Azido Group,* Wiley, N.Y., p. 331 (1971). The most common and versatile approach is the thermal cycloaddition of azides to alkynes; H. Wamhoff in *Comprehensive Heterocyclic Chemistry,* S. R. Katritzky (Ed.), Pergamon Press, N.Y., Vol. 5, p. 705 (1984); K. T. Finley, *Chem. Heterocyclo Compd.,* 39, 1 (1980). A wide range of functionality on both alkyne and azide components is tolerated in the thermal cycloaddition reaction and the approach to a specific target is generally determined by the availability of requisite precursors. Thus, disubstituted 1,2,3-triazoles, such as 86 in Scheme 17, may be prepared by heating a terminal alkyne 83 with an azide such as 85. Although the 1,4-isomer is often produced regiospecifically, a mixture of 1,4- and 1,5-regioisomers may result. Alternatively, a 4(5)-substituted-1,2,3-triazole may be

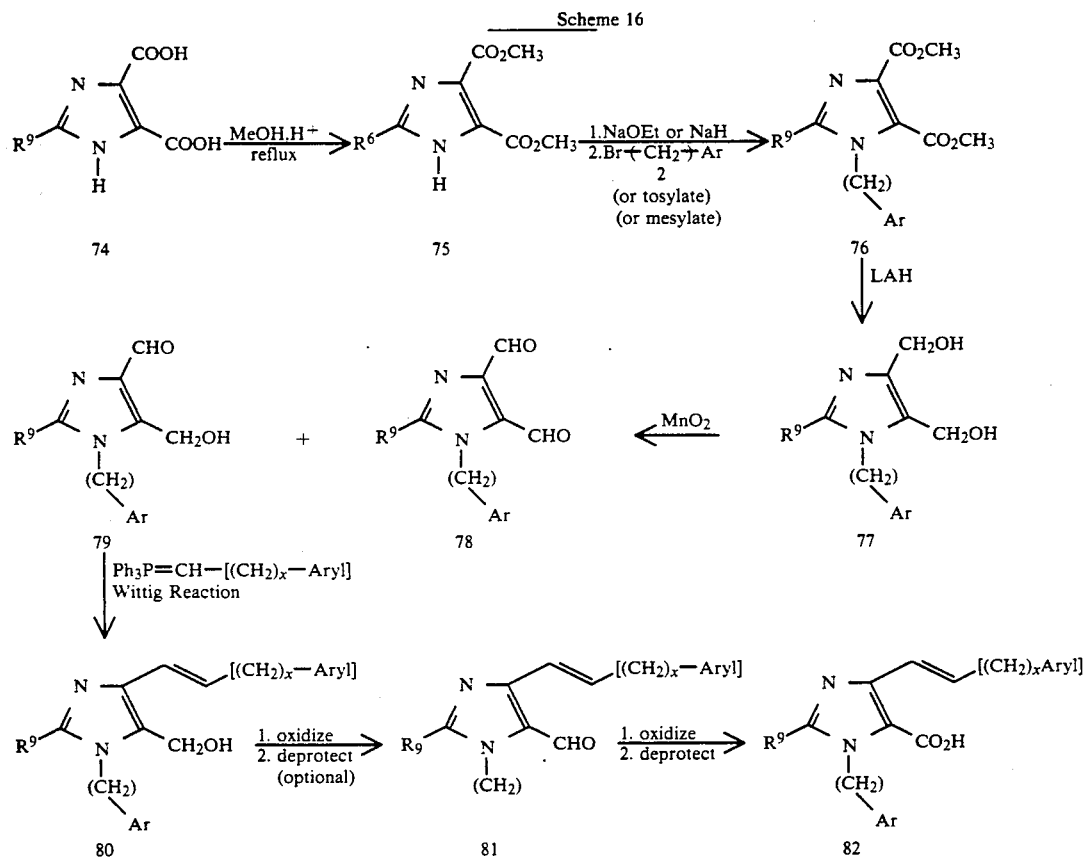

Scheme 16

With regards to pyrroles, triazoles and tetrazoles, the approaches described for each class of heterocycle generally encompass two major strategies. The first involves N-alkylation of a preformed mono- or disubstituted heterocycle with an appropriately functionalized arylmethyl halide. The second involves cycloaddition or cyclocondensation of two or three strategically prepared components to generate directly the heterocycle possessing the functionality needed to produce the final products, following relatively minor transformations. The approach used for a given example will depend on the availability of starting materials and compatibility of pendant functionality to the required reaction conditions.

N-alkylated with an appropriately functionalized benzyl halide such as 87. In this approach, any or all of the three ring nitrogens may compete in the alkylation depending upon the nature of the substituents on either component and the specific reaction condition, H. Gold, *Liebigs Ann. Chem.,* 688, 205 (1965); T. L. Gilchrist, et al., *J. Chem. Soc., Perkin. Trans.,* 1, 1 (1975). Thus, compounds such as 88 may also be produced.

Scheme 17

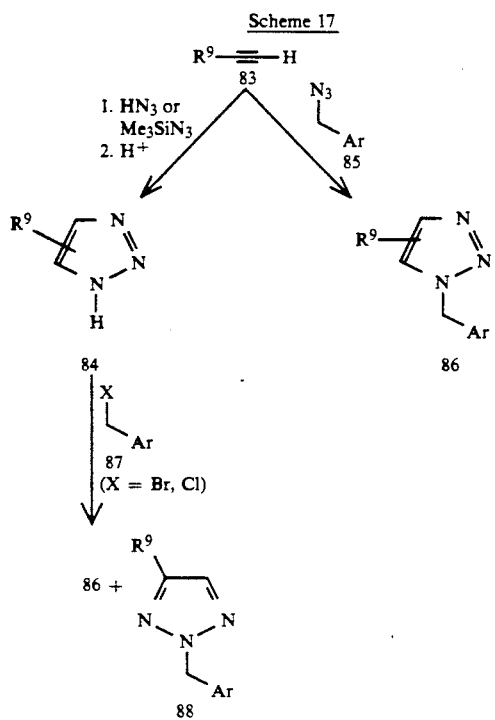

As shown by Scheme 18, the functionalized arylmethyl azides 91 may be prepared from the corresponding arylmethyl halides 90 via displacement with an azide salt such as sodium azide in a polar solvent such as dimethylformamide, dimethylsulfoxide or under phase transfer conditions at room temperature for 18-48 hours. The arylmethyl bromides 90 may be made by a variety of benzylic halogenation methods familiar to one skilled in the art; for example, benzylic bromination of arylmethyl derivatives 89 occurs in an inert solvent such as carbon tetrachloride in the presence of a radical initiator such as benzoyl peroxide at temperatures up to reflux conditions.

Scheme 18

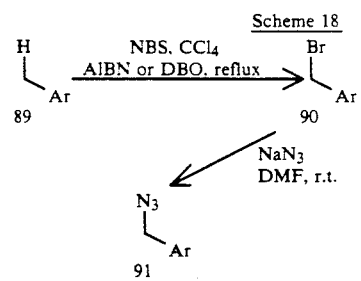

The more common and unambiguous syntheses of 1,2,4-triazoles from acyclic precursors generally involve hydrazine derivatives, due to the ease of forming C—N and C=N bonds over the relative difficulty of forming N-N bonds, J. B. Palya in *Comprehensive Heterocyclic Chemistry*, A. R. Katritzky (Ed.), Pergamon Press, NY, Vol. 5, p. 762 (1984). Synthesis of compounds with substituents on N-4 may be approached by methods illustrated in Scheme 19. Reaction of an intimate mixture of orthoesters 92, acylhydrazines 93, and amines 94 in an appropriate solvent like xylenes or any of the lower alcohols at or near the reflux temperature for 1-24 hours produces 1,2,4-triazoles P. J. Nelson and K. T. Potts, *J. Org. Chem.*, 27, 3243 (1962); Y. Kurasawa, et al., *J. Heterocyclic Chem.*, 23, 633 (1986). Alternative access to such structures may also be gained by condensing N,N'-diacylhydrazines 96a with amines 94 or cyclocondensation of appropriately substituted amidrazones such as 95a, *Comp. Het. Chem.*, Vol. 5, p. 763. (Note, that in Schemes 19, 20, 21, 22, 24, 25, 26 and 27, $R^1$ and $R^2$ do not refer to $R^1$ and $R^2$ of the scope but are designated in that manner to show that they can be different.)

The versatility of this approach is expanded upon in Scheme 20. Groups $R^1$ and $R^2$ may be carried by either the orthoester 92, 97 or acylhydrazine 93, 96 moieties depending upon their availability. Experimentally, the orthoester and acylhydrazine are first reacted to produce, presumably, 1,2,4-oxadiazoles 98 which may be isolated (if stable) but are commonly reacted in situ with amines 94 to ultimately afford 95. Alternatively, oxadiazoles 98 may be transformed to simpler triazoles 99 by treatment with ammonia. Alkylation of this species gives rise to a mixture of N-1 and N-2 substituted products 100, K. T. Potts, *Chem. Rev.*, 61, 87 (1961); K. Schofield, M. R. Grimett and B. R. T. Keene; *Heteroaromatic Nitrogen Compounds: The Azoles*, Cambridge, p. 81 (1975). N-4 alkylation of simple 1,2,4-triazoles has been observed only rarely, M. R. Atkinson and J. B. Palya, *J. Chem. Soc.*, 141 (1954). An alternative approach to such N-1 and N-2 substituted triazoles may be illustrated by reactions between 101 and benzylhydrazines 102. In 101, the dotted lines leave the presence or absence of a bond open, thus allowing possible reactants like ($R^1$COX, $R^2$COX and $NH_3$) or ($R^1$CONH$^2$ and $R^2$COX) or ($R^1$COX and $R^2$CONH$_2$) or ($R^1$CONHCOR$^2$); X stands for a suitable leaving group like Cl, OH, or $H_2O$.

Orthoesters, such as 92 and 97 (Scheme 21) are most generally available through alcoholysis of imidate ester hydrochlorides 104 which are usually prepared from the corresponding nitriles 103 by addition of alcohols (usually methanol or ethanol) in the presence of anhydrous hydrogen chloride, R. H. De Wolfe, *Carboxylic Ortho Acid Derivatives: Preparation and Synthetic Applications*, Academic Press, NY, pp. 1-54. The synthesis is usually conducted as a two-step process, the first being preparation and isolation of the imidic ester hydrochloride 104. The lower aliphatic members of this class are often prepared by addition of a slight excess of anhydrous hydrogen chloride to a chilled solution of the nitrile in a slight excess of an alcohol. A suitably inert solvent like ether, benzene, chloroform, nitrobenzene or 1,4-dioxane is then added, the resulting mixture is allowed to stand in the cold (60° C.) for several hours to a week and the product is collected by suction filtration and washed free of residual solvent and hydrogen chloride, S. M. McElvain and J. W, Nelson, *J. Amer. Chem, Soc.*, 64, 1825 (1942); S. W. McElvain and J. P. Schroeder, *J. Amer. Chem. Soc.*, 71, 40 (1949). These imidate ester hydrochlorides are converted to orthoesters by stirring with an excess of an alcohol (generally the same one used above) for up to 6 weeks or, more efficiently, by refluxing the imidate ester hydrochloride with a five to tenfold excess of the alcohol in ether for up to 2 days, Even higher yields can be obtained by stirring the imidate ester at room temperature in a mixture of the alcohol and petroleum ether, S. M. McElvain and C. L. Aldridge, *J. Am. Chem. Soc.*, 75, 3987 (1953); Ibid, 80, 3915 (1958). Orthoesters prepared by the above described method may incorporate a rather large array of functionality, including aliphatic, alkenyl, alkynyl, aromatic, halogen, ether, ester, amino, nitro, thio (in various oxidation states), amide, or urethane groups. Another approach, less commonly used, involves electrolysis of trihalomethyl compounds 105 or α-halo ethers, though this approach is limited to halides having no α-hydrogens hydrogens and is generally applicable to the synthesis of trialkyl orthobenzoates, H. Kevart and M. B. Price, *J. Amer. Chem. Soc.*, 82, 5123 (1960); R. A. McDonald and R. S. Krueger, *J. Org. Chem.*, 31, 488 (1966).

Acyl hydrazines 93, 96 may be prepared in a straightforward manner by reaction of the corresponding esters (106; X=OR) with hydrazine (or hydrazine monohydrate) in an appropriate solent like alcohol, acetonitrile, DMF or pyrroline at temperatures of 0° C. to reflux for 1 to 18 hours (Scheme 22). The related acid (X=OH), anhydride (X=OCOR), amide (X=NH2) or acid halide (X=Cl, Br) may also be used, but the more reactive acid derivatives (e.g., acid halides) are generally used for preparation of N,N'-diacylhydrazines 96a), except in those instances where the larger size $R^{1(2)}$ groups lead to relatively less reactive species.

Symmetrical N,N'-diacylhydrazines 96a are best prepared by reactions of 2 equivalents of an acylhalide (106; X=Cl, Br) with hydrazine or, alternatively, by oxidation of the corresponding monoacylhydrazine. "Mixed" N,N'-diacylhydrazines 96 are obtained through a two-step process by first preparing the monoacylhydrazine 93, 96 followed by its reaction with the appropriate acyl halide (106; X—Cl, Br)

Arylmethylhydrazines 102, 111 may be prepared by a variation of the Raschig process for hydrazine by substituting benzyl amines 110 for ammonia and aminating these with chloramine or hydroxylamine-O-sulfonic acid, W. W. Schienl, Aldrichimica Acta, 13, 33 (1980) as illustrated in Scheme 23, equation b). Alkylhydrazines have also been prepared from alkyl halides or sulfates. Although the tendency here is towards polyalkylation, monoalkylation is favored by bulky groups or by use of a large excess of hydrazine, S. N. Kast, et al., *Zh. Obshch, Khim,* 33, 867 (1963); C.A., 59, 8724e (1963).

Arylmethylamines 110may be prepared by a variety of methods, some of the more common ones being illustrated in Scheme. 23, equation a). The most direct approach, aminolysis of halides, is often accompanied by the formation of secondary, tertiary and even quaternary amines, *J. Amer. Chem. Soc.,* 54, 1499, 3441 (1932).

A more efficient approach involves reduction of the corresponding arylmethylazides 91 by catalytic reduction, hydride reagents, triphenylphosphine or stannous chloride, among others, S. N. Maiti, et al., *Tetrahedron Letters,* 1423 (1986). Reaction of arylmethylhalides 90 with potassium (or sodium) phthalimide followed by hydrolysis or hydrazinolysis of the intermediate N-arylmethylphthalimides 107 constitutes the Gabriel Synthesis of primary amines and is highly attractive from the standpoint of the wide range of functional groups tolerated and mildness of conditions for both steps, M. S. Gibson and R. W. Bradshaw, *Angew Chem. Int. Ed. Engl.,* 7, 919 (1968). Reductive amination of benzaldehydes 109 with ammonia and hydrogen using a nickel catalyst is another common approach, *Organic Reactions,* 4, 174 (1948). Reduction of arylmethylnitriles 108 by metal hydrides or catalytic hydrogenation is also commonly employed, *J. Chem. Soc.,* 426 (1942); *J. Amer. Chem. Soc.,* 82, 681, 2386 (1960); *Organic Reactions,* 6, 469 (1951). Other reagents have been employed for conversion of intermediates 90, 108 and 109 to 110, J. T. Harrison and S. Harrison, *Compedium of Organic Synthetic Methods,* John Wiley and Sons, N.Y., Vols. 1-5 (1971-1984).

Scheme 19

$$R^1C(OR)_3 + R^2CONHNH_2 + \underset{Ar}{NH_2}$$

92, 93, 94

80–140° C.

$$R^1 \underset{N}{\overset{N-N}{\diagdown}} R^2$$
$$\underset{Ar}{|}$$
95

R'CONHNHCOR² + NH₂—Ar  ⇌  $HN \overset{R^1}{\underset{Ar}{\diagdown}} NNHCOR^2$ 96a, 94, 95a Scheme 20

92 + 93    $R^1CONHNH_2$ 96 + $R^2C(OR)_3$ 97

$$R^1 \underset{O}{\overset{N-N}{\diagdown}} R^2$$

98    94

NH₃ ↙    ↘ 95

$$R^1 \underset{N}{\overset{}{\diagdown}} N \underset{H}{\overset{}{\diagdown}} R^2$$
99

$$R^1 \underset{N}{\overset{N}{\diagdown}} \underset{Ar}{\overset{R^2}{\diagdown}} N$$
90
100

$$\underset{O}{\overset{H}{R^1}} N \underset{O}{\overset{}{\diagdown}} R^2 + NHNH_2—Ar$$

101    102

Scheme 21

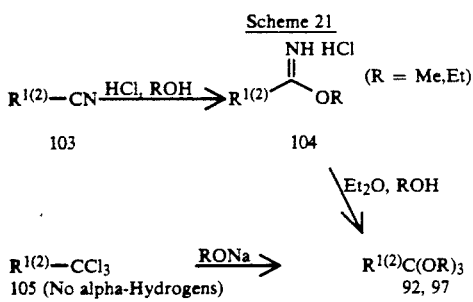

Scheme 22

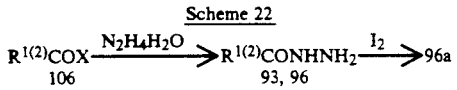

Scheme 23

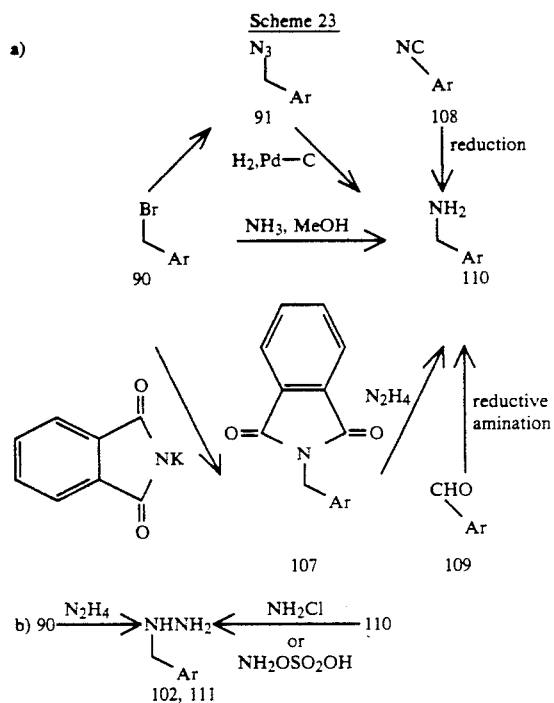

A general and versatile approach to pyrazoles involves condensation of a 1,3-difunctional compound (usually dicarbonyl) with hydrazine or its derivatives, as shown in Scheme 24 for pyrazoles of the formula 114, and reviewed by G. Corspeau and J. Elguerv, *Bull. Soc., Chim. Fr.*, 2717 (1970). Rarely have pyrazoles been prepared in which the N-N bond is the last step of the ring closure, J. Elguerv in *Comprehensive Heterocyclic Chemistry*, S. R. Katritzky (Ed. Pergamon Press, NY, Vol. 5, p. 274 (1984); J. Barluenga, *J. Chem. Soc., Perkin Trans.*, 1, 2275 (1983).

The condensation of 1,3-dicarbonyl compounds with hydrazine hydrate or arylmethyl hydrazine derivatives is generally carried out by admixture of the two components in a suitable solvent like a lower alcohol, ether, or THF at 0° C. to the reflux temperature for 1-18 hours.

Alkylation of pyrazoles 113 can be carried out either by reactions of a preformed sodium (or potassium) pyrazole salt with an appropriately substituted arylmethyl halide 87 in a polar solvent like DMF or DMSO at 0° C. to room temperature or by reaction between free pyrazoles 113 and 87 in a like solvent and an acid scavenger such as sodium bicarbonate or potassium carbonate, as described for the triazole series.

In either approach, mixtures of N-1 and N-2 substituted pyrazoles of varying ratios are generally obtained which can be separated by conventional chromatographic methods.

The synthesis of 1,3-dicarbonyl compounds has received considerable attention in the literature and most of the major approaches towards 1,3-diketones 112 of interest in this invention are illustrated by Scheme 25.

Esters (106; X=OR) can be reacted with methyl ketones 115 using bases like sodium ethoxide, sodium hydride or sodium amide in a suitable solvent like alcohol, DMF, DMSO or benzene at 0° C. to reflux for 4-18 hours with 30-70% efficiency, J. M. Sprague, L. J. Beckham and H. Adkins, *J. Amer. Chem. Soc.*, 56, 2665 (1934). Metallation of hydrazines 116 with n-BuII followed by reaction with carboxylic acid chlorides (106; X=Cl) and subsequent hydrolysis affords 112, D. Enders and P. Wenster, *Tetrahedron Lett.*, 2853 (1978). Metallation of 115 with the non-nucleophilic mesityl lithium followed by acylation also affords 112, A. K. Beck, M. S. Hoelstein and D. Seebach, *Tetrahedron Lett.*, 1187 (1977); D. Seebach, *Tetrahedron Lett.*, 4839 (1976).

As shown in Scheme 25, equation b), the addition of Grignard reagents to 5-keto carboxylic acid chlorides may be limited to monoaddition at low temperatures to provide 112, C. D. Hurd and G. D. Kelso, *J. Amer. Chem. Soc.*, 62, 1548 (1940); F. Sato, M. Trone, K. Oyuro, and M. Sato, *Tetrahedron Lett.*, 4303 (1979). Lithium dialkyl copper reagents ($R_2CuLi$) have also been used, Luong-Thi and Riviero, *J. Organomet. Chem.*, 77, C52 (1974). Analogously, addition of alkyllithium reagents ($R^2Li$) to the monoanions of 5-keto esters 118 also give rise to 1,3-diketones, S. N. Huckin and L. Weiler, *Can. J. Chem.*, 52, 1379 (1974).

Eschenmoser has demonstrated a synthesis of 5-diketones through a sulfur extrusion reaction of keto thioesters 119 with tributylphosphine, triethylamine and lithium perchlorate, S. Eshenmoser, *Helv. Chim. Acta.*, 54, 710 (1971).

The rearrangement of α,β-epoxy ketones 120 to β-diketones 112 catalyzed by Pd° has been reported, R. Noyori, *J. Amer. Chem. Soc.*, 102, 2095 (1980).

Mixed anhydrides such as 122, available from carboxylic acids 121 and trifluoroacetic anhydride, have been shown to acylate alkynes 83 to produce the enol trifloroacetate of a β-diketone 124. Transesterification by refluxing with methanol liberates the β-diketone 112, A. L. Henne and J. M. Tedder, *J. Chem. Soc.*, 3628 (1953).

Scheme 24

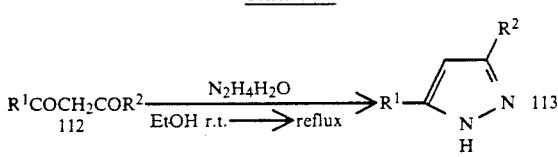

-continued
Scheme 24
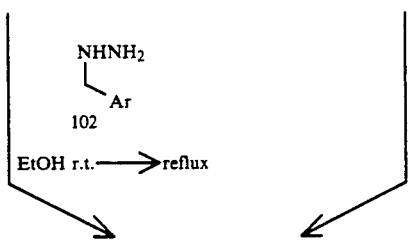
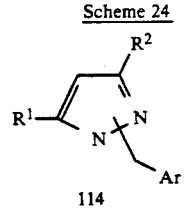
Scheme 25
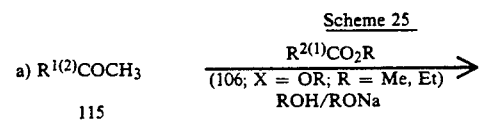
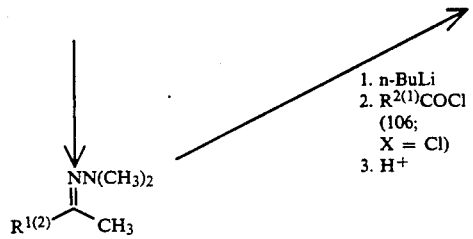
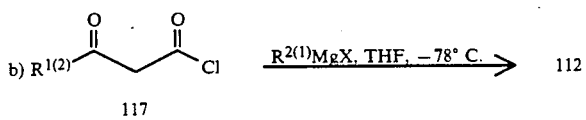
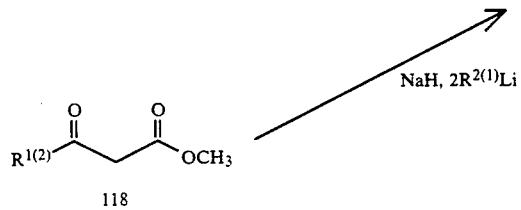
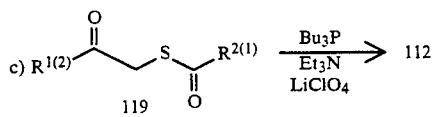
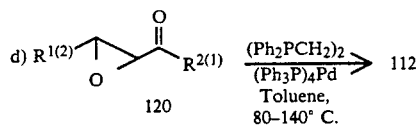
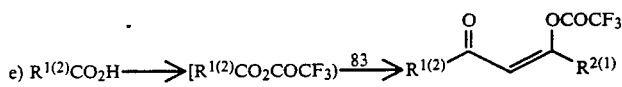
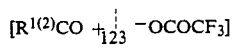
Synthetic approaches towards pyrroles have received wider attention in the literature than most any other heterocycle and numerous methods for their construction have been published. R. J. Sundberg in *Comprehensive Heterocyclic Chemistry*, A. R. Katritzky (Ed.), Pergamon Press, NY (1984), Vol. 4, p. 705; *Syn-*

*thesis*, 281 (1946). The following discussion is restricted to the most common and reliable methods towards the synthesis of pyrroles within the general scope of the invention.

The cyclizative condensation of 1,4-dicarbonyl compounds with ammonia, primary amines or related compounds, the Paal-Knorr reaction, is one of the most general and widely applicable pyrrole syntheses, R. A. Jones and G. P. Bean, *The Chemistry of Pyrroles*, Academic Press, London, p. 77–81 (1977). The generality of this approach is primarily determined by the availability of the dicarbonyl precursors, 125, as illustrated by Scheme 26. By heating such diketones with ammonia or amines in a solvent like benzene, toluene or methylene chloride with a catalyst such as sulfuric acid, acetic acid, p-toluenesulfonic acid, alumina or even titanium tetrachloride, pyrroles like 126 may be prepared. By choosing the appropriate arylmethylamine 110 one may ultimately incorporate the arylmethyl group into the fully elaborated pyrroles 127. Alternatively, one may alkylate the disubstituted pyrroles 126a with arylmethyl halides 90 under conditions previously described (Schemes 17, 20 or 24) to give the same 127.

The cyclization of diynes 128 with amines in the presence of cuprous chloride has been reported (Scheme 26a, equation a), but this approach is generally restricted to the preparation of symmetrically substituted pyrroles since the diynes are usually made by oxidative coupling of alkynes, K. E. Schulte, J. Reish, and H. Walker, *Chem. Ber.*, 98 (1965); A. J. Chalk, *Tetrahedron Lett*, 3487 (1972).

Furans 130 have been converted directly to pyrroles by treatment with amines but the harsh conditions required (400° C./Al$_2$O$_3$)precludes its generality. 2,5-Dialkoxytetrahydrofurans 132 have been more commonly employed as furan (or 1,4-dicarbonyl) equivalents and react readily with aliphatic or aromatic amines (and even weakly nucleophilic sulfonamides) to give pyrroles as shown in Scheme 26a, equation b), J. W. F. Wasley and K. Chan, *Synth. Commun.*, 3, 303 (1973). Although commercially available 2,5-dialkoxytetrahydrofurans 132 ($R^1=R^2=H$) generally restrict one to preparing 1-substituted pyrroles, more highly substituted systems may be obtained by a three-step alcoholysis of the appropriate furans 130 to the more highly substituted 2,5-dialkoxytetrahydrofurans 132 as shown by Scheme 26a, equation b), N. L. Weinberg and H. R. Weinberg, *Chem. Rev.*, 68, 449 (1968); N. Elming, *Adv. Org. Chem.*, 2, 67 (1960).

The Hantzsch synthesis utilizes the condensation of α-haloketones 133 and β-ketoesters 134 in the presence of ammonia or a primary amine to give pyrroles such as 135, as shown in Scheme 27, equation a) ; A. Hantzsch, *Chem. Bet.*, 23, 1474 (1890); D. C. von Beelen, J. Walters, and S. von der Gen, *Rec. Tray. Chim.*, 98, 437 (1979). Among the numerous modifications reported over the years, the substitution of 133 with the readily available α-hydroxyaldehydes or nitroalkenes has expanded the versatility and generality of this important method, D. M. McKinnon, *Can. J. Chem.*, 43, 2628 (1965); H. George and H. J. Roth, *Arch. Pharm.*, 307, 699 (1974); C. A. Grok and K. Camenisch, *Helv. Chem. Acta*, 36, 49 (1953).

The closely related Knorr condensation involves the reaction between amino carbonyl compounds (or their precursors) and carbonyl (or dicarbonyl) compounds, J. M. Patterson, *Synthesis*, 282 (1976). Representative methods for preparing 2,3- or 2,5-disubstituted pyrroles 138 and 141 are shown by Scheme 27, equations b) and c), S. Umio, et al., Jap. Pat. 7018653, Fujisawa Pharmaceutical Co., Ltd. (1970;) (C.A. 73, 77039, (1970)); K. Tanaka, K. Kariyone, S. Umio, *Chem. Pharm. Bull.* (Tokyo), 17, 611 (1969).

The elaboration of an appropriately functionalized pyrrole is another method for preparing pyrroles of general formula I. Methyl (or ethyl) 5-formyl-1H-pyrrole-2-carboxylate 146 is a particularly useful intermediate as regards pyrroles claimed in this invention and has been prepared by a number of methods as shown by Scheme 28, equation a), W. A. Davies, A. R. Pinder and I. G. Morris, *Tetrahedron*, 18, 405 (1962); *Org. Syn.*, Vol. 36 p. 74; *Org. Syn.* Vol. 51.

More recently, Ullrich has extended the Vilsmeyer-Haack formulation of pyrroles to include vinylogous systems such as 149 by using 3-(N,N-dimethylamino)acrolein 148 as a vinylogous N,N-dimethylformamide derivative, as shown by Scheme 28, equation b) , F. W. Ullrich and E. Breitmaier, *Synthesis*, 641 (1983); W. Heinz, et al., *Tetrahedron*, 42, 3753 (1986).

Scheme 29 illustrates generally how N-alkylation of with the appropriate arylmethyl halides (as discussed earlier, Schemes 17, 20 or 24), followed by standard manipulation of the pendant carbonyl groups using methods familiar to one skilled in the art can produce pyrroles of general formula I.

Scheme 26

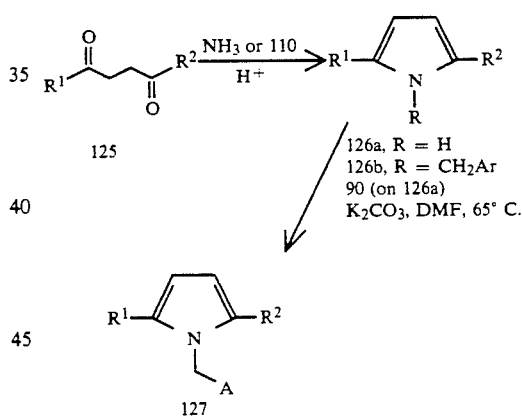

Scheme 26a

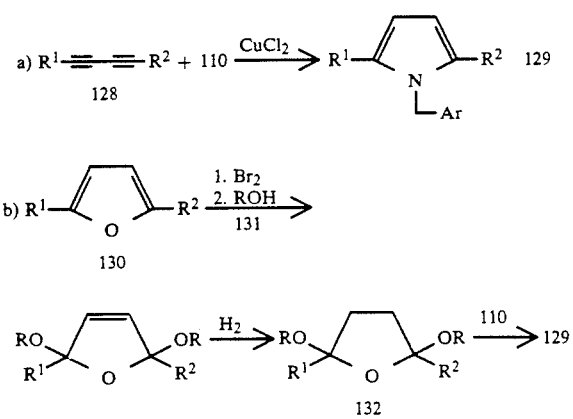

Scheme 27

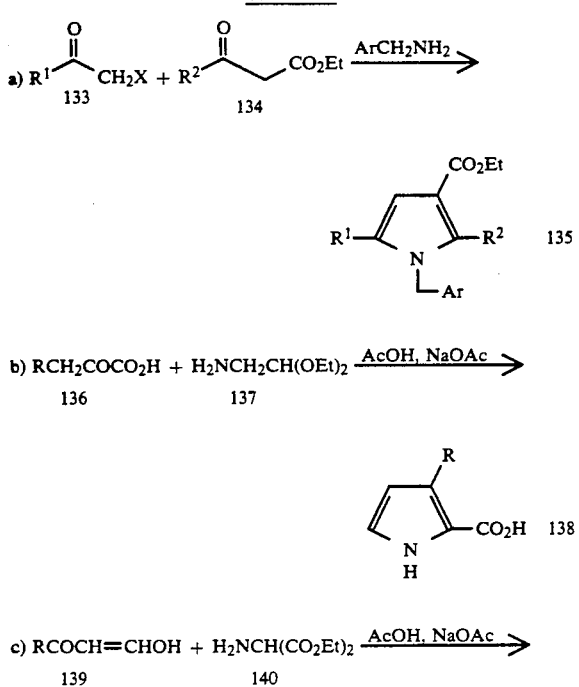

Scheme 28

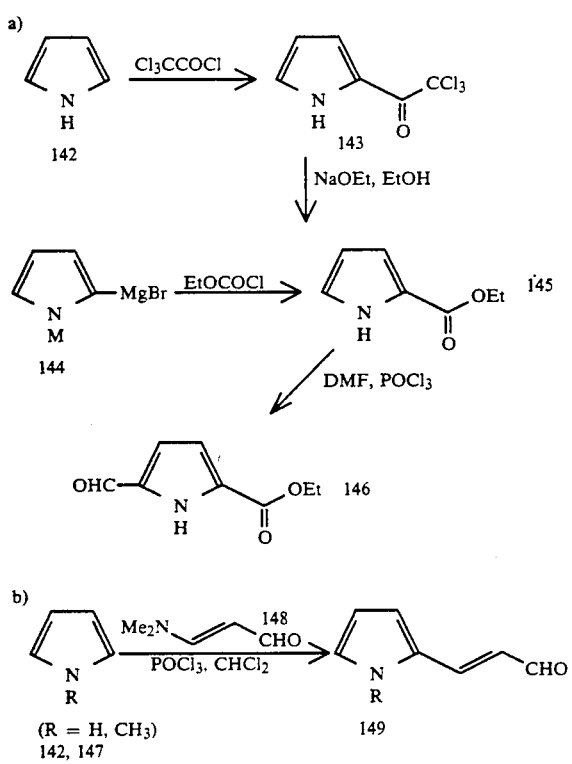

Scheme 29

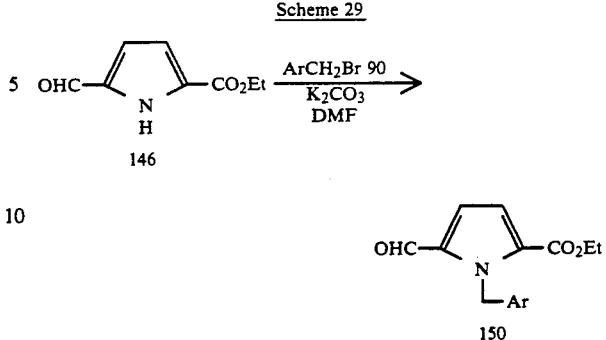

Described herein are general methods for the preparation of specific functional groups on $R^8$ claimed in this invention. As before, it is understood by those skilled in the art of organic synthesis that all functionality present must be consistent with the chemical transformations proposed.

As shown in Scheme 30, equation a), arylmethyl heterocycles 151 where $R^8$=CH$_2$OH may be converted to the corresponding halide, mesylate or tosylate by a variety of methods familiar to one skilled in the art. Preferably, the alcohol 151 is converted to the chloride 152 using thionyl chloride in an inert solvent at temperatures of 20° C. to the reflux temperature of the solvent.

Chloride 152 may be displaced by a variety of nucleophiles. For example, excess sodium cyanide in DMSO at temperatures of 200° to 100° C. may be used to form cyanomethyl derivatives 153. These nitriles 153 may be hydrolyzed to carboxylic acids 154 by treatment with strong acid or alkali. Preferably, treatment with a 1:1 (v/v) mixture of concentrated aqueous hydrochloric acid/glacial acetic acid at reflux temperatures for 2–96 hours or by treatment with 1 N sodium hydroxide in an alcohol solvent such as ethanol or ethylene glycol for 2–96 hours at temperatures from 20° C. to reflux can be used. Alternatively, the nitrile group can be hydrolyzed in two steps by first stirring in sulfuric acid to form the amide followed by acidic or basic hydrolysis to furnish the carboxylic acids 154.

These carboxylic acids 154 may be esterified to esters 15f using standard methods, for example, stirring the carboxylic acids 154 with an alcohol in a suitably inert solvent containing hydrogen chloride or similar catalysts, or by first converting the carboxylic acids 154 to the corresponding acid chloride with thionyl chloride or oxalyl chloride followed by treatment with the appropriate alcohol. Carboxylic acids 154 may also be reduced to the corresponding hydroxymethyl compounds 156 using reductants like LiAlH$_4$ or B$_2$H$_6$, thus constituting an overall homologation for the process 151+156.

Alcohol derivatives 151 or 156 may be acylated to give esters 157 by a variety of procedures. As shown in Scheme 30, equation b), acylation can be achieved with 1–3 equivalents of an acyl halide or anhydride in a suitable solvent like diethyl ether or tetrahydrofuran in the presence of a base such as pyridine or triethylamine. Alternatively, such alcohols 151, 156 may be acylated by reaction with a carboxylic acid and dicyclohexylcarbodiimide (DCC) in the presence of a catalytic amount of 4-(N,N-dimethylamino)pyridine (DMAP) via the procedure described by A. Hassner, *Tetrahedron Lett.*, 46, 4475 (1978). Treatment of 151 or 156 with a solution of carboxylic acid anhydride in pyridine optionally with a catalytic amount of DMAP at temperatures of 20°–100° C. for 2–48 hours is the preferred method.

Ethers 158 can be prepared from the alcohols 151, as shown in Scheme 30, equation c), by treatment of 151 in a solvent such as DMF or DMSO with potassium butoxide or sodium hydride followed by treatment with $R^{18}L$ at 25° C. for 1–20 hours, where L is a halogen, mesylate or tosylate group. Alternatively, treatment of chlorides 152 with 1–3 equivalents of $R^{18}OM$ where M is sodium or potassium, for 2–10 hours at 25° C. either in $R^{18}OH$ as solvent or in a polar solvent such as DMF Free-radical bromination of 147 by UV-irradiation for 1–4 hours in the presence of N-bromosuccinimide in an inert solvent such as carbon tetrachloride at 25° C. gives bromides 165. Treatment of these intermediates 165 with an appropriate base such as DBU, triethylamine, or potassium t-butoxide, affords (predominantly or exclusively) the trans-alkenylheterocycles 166. The corresponding cis-alkenyl derivatives 168 may be prepared as described above (for 162) or from the transalkenyl compounds 166 by oxidative cleavage with osmium tetroxide and sodium periodate to give aldehydes 167 followed by Wittig chemistry.

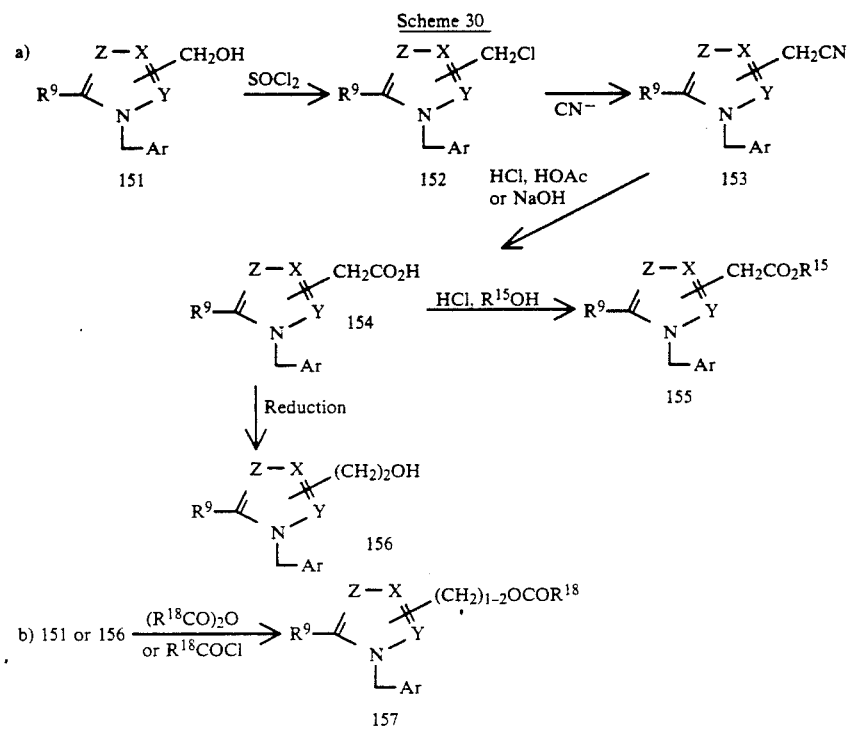

will also give ethers 158. Such ethers 158 may also be prepared, for example, by heating 158 for 3–15 hours at 60°–160° C. in $R^{18}OH$ containing an inorganic acid such as hydrochloric or sulfuric acids.

As shown by Scheme 30, equation d), amides 159 may be prepared from carboxylic acids 154 through a variety of methods familiar to one skilled in the art and as described previously.

As shown by Scheme 31, equation a), the hydroxymethyl group of 151 can be oxidized to the corresponding aldehydes 160 using a mild oxidant, such as manganese dioxide or cerric ammonium nitrate. Such aldehydes may undergo typical chain-extensions via the Wittig and Wittig-Horner-Emmons reactions to give alkenyl compounds such as 162 directly or react with Grignard and lithium reagents to give alcohols 161. These alcohols may undergo dehydration to the corresponding alkenyl compounds 162 using standard methods, for example, by first converting such alcohols to the corresponding mesylate, tosylate or halide derivatives followed by elimination using an appropriate base such as DBU, triethylamine, or potassium t-butoxide. These alkenes may be hydrogenated to the corresponding alkanes 163 to yield chain-extended analogs at $R^8$.

Alternative access to alkenyl-substituted heterocycles may be gained via the corresponding alkylheterocycles 164 as illustrated for Scheme 31, equation b).

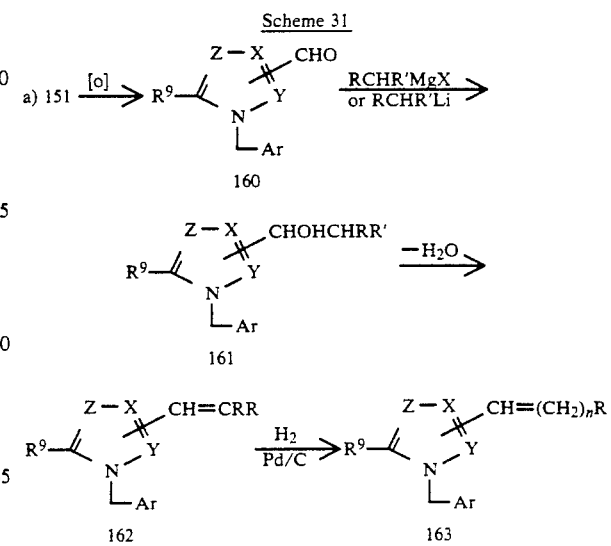

-continued
Scheme 31

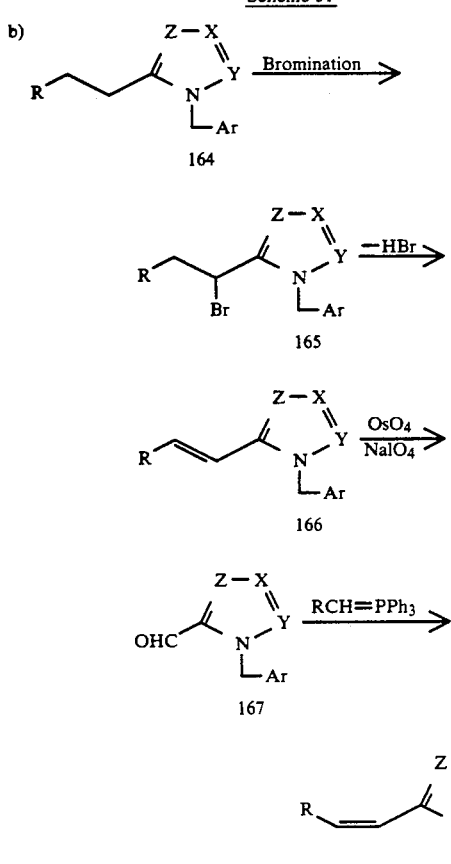

Scheme 32

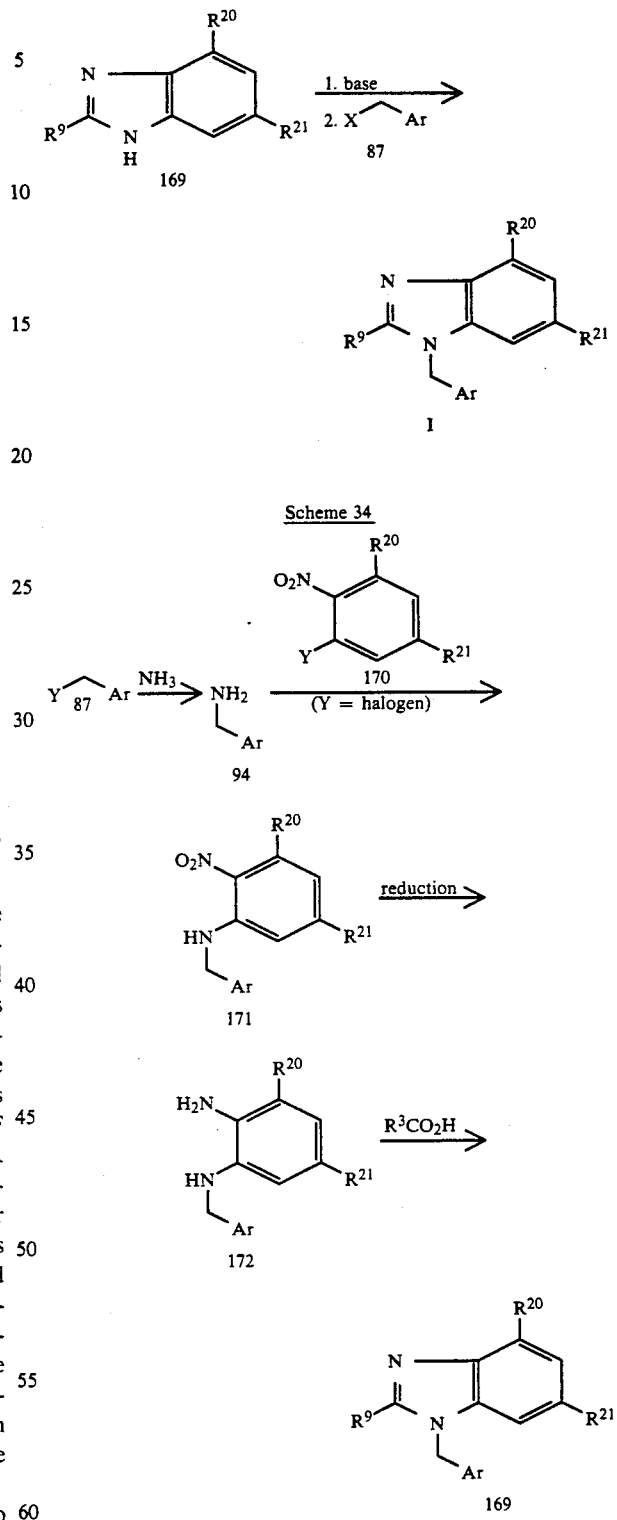

Arylmethylbenzimidazoles (V, W=CH in Structure I) can be prepared by direct alkylation onto benzimidazole 169 with an appropriately protected arylmethyl halide, tosylate or mesylate 87 in the presence of base as shown in Scheme 32. Preferably, the metallic benzimidazolide salt is prepared by reacting benzimidazole 169 with a proton acceptor such as MH where M is lithium, sodium or potassium in a solvent such as DMF or by reacting it with a metal alkoxide of formula MOR where R is methyl, ethyl, t-butyl or the like in an alcohol solvent such as ethanol or t-butanol, or a polar aprotic solvent such as DMF. The benzimidazole salt is dissolved in an inert aprotic solvent such as DMF, and treated with an appropriate alkylating agent 87. Alternatively, benzimidazole 169 can be alkylated with arylmethyl halide (87; where Y=Br or Cl) in the presence of a base such as sodium carbonate, potassium carbonate, triethylamine or pyridine. The reaction is run in an inert solvent such as DMF or DMSO at 20° C. to the refluxing temperature of the solvent for 1-10 hours When $R^{20}$ and $R^{21}$ are not equivalent, mixtures of two regioisomer alkylation products are obtained. These isomers possess distinct physical and biological properties and can be separated and isolated by conventional separation techniques such as chromatography and/or crystallization.

An alternative synthesis for benzimidazole compounds of formula I is described in Scheme 94.

The functionalized arylmethylamines 94 can be made from the corresponding arylmethyl halide, tosylate or mesylate 87 via displacement with a nitrogen nucleophile, a procedure familiar to one skilled in the art. This displacement may be achieved using azide ion, ammonia, or phthalimide anion, etc., in a neutral solvent such as DMF, DMSO, etc., or under phase transfer conditions. The arylmethyl halide 87 can be made by a variety of benzylic halogenation methods familiar to one skilled in the art, for example, benzylic bromination of methylanthracene derivatives with N-bromosuccinimide in an inert solvent such as carbon tetrachloride in the presence of a radical initiator such as benzoyl peroxide at temperatures up to reflux conditions.

Reaction of an arylmethylamine 94 with an o-halogen substituted nitrobenzene 170 affords the corresponding nitro compound 171.

o-Phenylenediamine intermediates 172 can be obtained from the corresponding nitro compounds 171 by reduction. A variety of reduction procedures may be used such as Fe/acetic acid (D. C. Owsley, J. J. Bloomfield, *Synthesis*, 118 (1977)), stannous chloride (F. D. Bellamy, *Tetrahedron Lett.*, 839 (1984)) or careful hydrogenation over a metal catalyst such as palladium.

Reaction of 172 with a carboxylic acid under a variety of conditions some of which are described in the disclosure for Scheme 35, equation b) provides the desired compound 169.

The benzimidazole compounds 169 are readily available by any of a number of standard methods. Several of these synthetic routes are illustrated in Scheme 35.

As shown in Scheme 35, equation a), a variety of benzimidazoles can be prepared by reduction of acylated o-nitroanilines 174 with various reducing agents such as Sn/HCl (H. Hubner, *Ann.*, 208, 278 (1881)) SnCl$_2$/HCl (L. I. Smith, et al., *J. Am. Chem. Soc.*, 57, 1289 (1935)), and Fe/acetic acid (M. A. Phillips, *J. Chem. Soc.*, 2393 (1928)). Another method for the conversion of an acylated o-nitroaniline into a 2-substituted benzimidazole 169 involves heating the compound with ferrous oxalate at a temperature in the range of 220°–225° C. (H. C. Waterman, et al., *J. Org. Chem.*, 14, 289 (1949)). The transformation of an acylated o-nitroaniline into a benzimidazole 169 can also be effected by electrolytic reduction (K. Brand, et al., *Ber.*, 39, 4058 (1906)) or by catalytic hydrogenation (R. Adams, et al., *J. Am. Chem. Soc.*, 70, 2667 (1948)).

Alternatively, benzimidazoles 169 can be synthesized by reacting an o-phenylenediamine and a carboxylic acid (M. A. Phillips, *J. Chem. Soc.*, 1409 (1930)), or an acid anhydride as shown in Scheme 35, equation b). One method involves refluxing an equimolar mixture of a substituted o-phenylenediamine and a carboxylic acid or an acid anhydride in dilute hydrochloric acid. Benzimidazole 169 can also be prepared by reaction of an appropriately substituted o-phenylenediamine and an ester. Reaction of an acid amide and an o-phenylenediamine as described in S. Von Niementowski, Ber., 30, 3062 (1897) also results in the formation of benzimidazoles of formula 169.

Alternatively, as shown in Scheme 35 equation c), heating the hydrochloride salt of an o-phenylenediamine with a nitrile at elevated temperatures (~200° C.) results in the formation of a 2-substituted benzimidazole 169 (E. L. Holljes and E. C. Wagner, *J. Org. Chem.*, 9, 31 (1944)).

Benzimidazole 169 can also be prepared by reaction of o-phenylenediamine with an iminoether or an iminothioester as shown in equation d) (F. E. King et al., *J. Chem. Soc.*, 1396 (1949)).

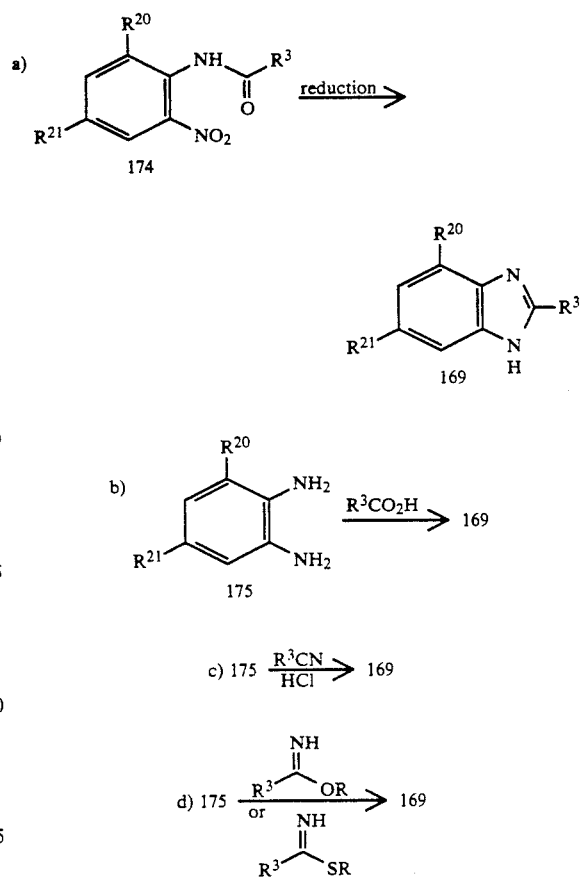

Scheme 35

Substituents $R^{20}$ and $R^{21}$ can be incorporated into the benzene ring at the beginning of the synthesis such that the desired compounds 169 can be obtained via Scheme 35, or $R^{20}$ and $R^{21}$ can be derived from suitable synthetic precursors at a later stage in the synthesis.

The hydroxymethyl group on compound 176 can be readily oxidized to an aldehyde group by means of an oxidizing agent such as manganese dioxide as shown in Scheme 36. The aldehyde 177 will undergo chain extension reactions such as the Wittig and Wittig-Horner reactions, and enter into typical carbon-carbon bonding forming reactions with Grignard and lithium reagents as well as with compounds bearing activated methylene groups, known to one skilled in the art of organic synthesis.

Scheme 36

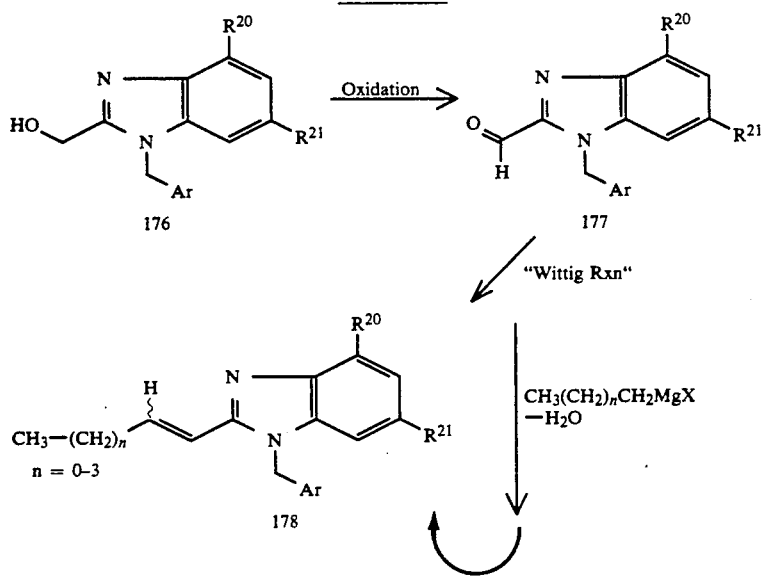

The ether 180 can be prepared from the alcohol 179 as shown in Scheme 37, equation a) by methods such as treatment of 179 in a solvent such as DMF or DMSO with potassium t-butoxide, sodium hydride, or the like followed by treatment with $R^{18}Y$ at 25° C. for 1-20 hours, where Y is a halogen, tosylate or mesylate.

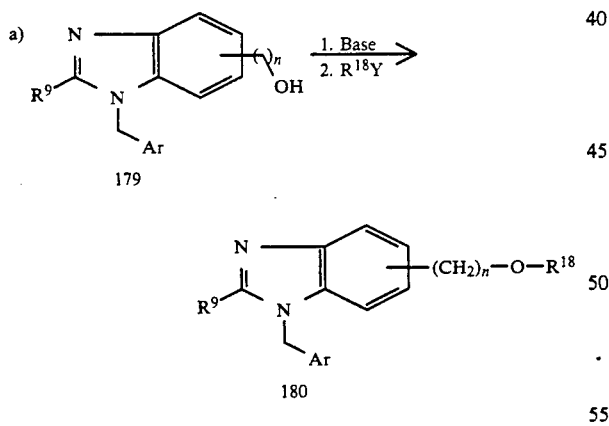

-continued
Scheme 37

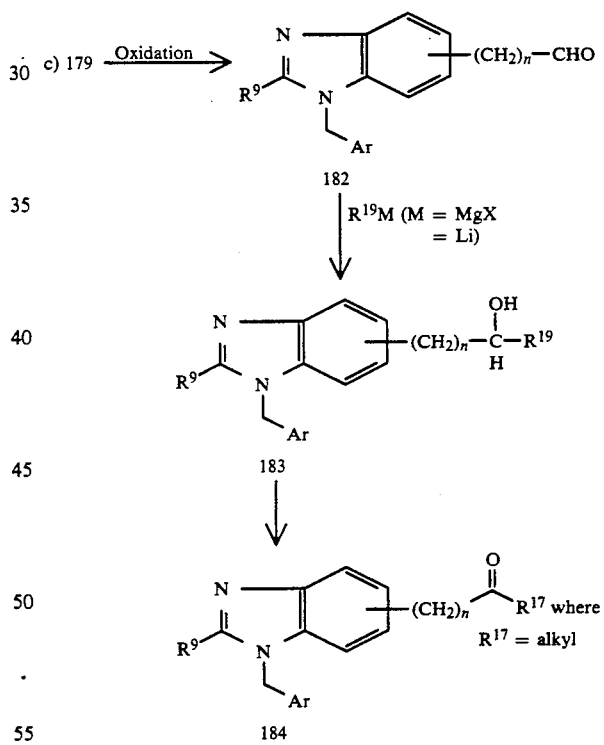

Hydroxymethyl derivative 179 may be acylated to give 181 by a variety of procedures. As shown in Scheme 37, equation b), acylation can be achieved with 1~3 equivalents of an acyl halide or an anhydride in a solvent such as diethyl ether, tetrahydrofuran, methylene chloride or the like in the presence of a base such as pyridine or triethylamine. Alternatively, 179 may be acylated by reaction with a carboxylic acid and DCC in the presence of a catalytic amount of 4-(N,N-dimethylamino)pyridine (DMAP) via the procedure described by A. Hassner, Tetrahedron Lett., 4475 (1978). Treatment of 179 with a solution of a carboxylic acid anhydride in pyridine optionally with a catalytic amount of DMAP at temperatures of 20°–100° C. for 2–48 hours is the preferred method.

The hydroxymethyl compound 179 can be oxidized to aldehyde 182 by treatment with an oxidizing agent such as manganese dioxide or pyridinium chlorochromate. Reaction of aldehyde 182 with an appropriate Grignard reagent affords alcohol 183 which can be oxidized to ketone derivative 184 by standard oxidizing procedures familiar to one skilled in the art.

Compounds where V=N and W=CH or V=CH and W=N or both V and W are N can be prepared by the same reactions described in the synthesis of the benzimidazoles with the exception that pyridines and pyrimidines should replace the corresponding benzene starting materials used for the benzimidazoles (for reviews see the following in *Comprehensive Heterocyclic Chemistry*, Vol. 5, A. R. Katritzky and C. W. Rees, eds., Pergamon Press, Oxford (1984): imidazo[4,5-b]pyridines, pp. 635–639; imidazo[4,5-c]pyridines, pp. 639–640; purines, pp. 570–576). For the synthesis of substituted pyrimidines, see D. J. Brown, *The Pyrimidines* and its Supplement No. I, from a series entitled *Heterocyclic Compounds*, A. Weissberger, ed., Wiley-Interscience, NY, 1970. For the synthesis of substituted pyridines, see the A. Weissberger, *Heterocyclic Compounds* series, *Pyridine and Its Derivatives*, parts 1, 2, 3 and 4 together with supplements 1–4, John Wiley and Sons, NY.

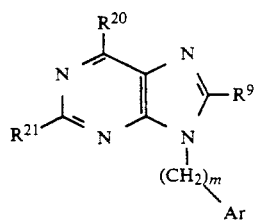

Generally, purines of formula I can be made by the alkylation onto the parent purine nucleus of an appropriately protected arylmethyl derivative in the presence of a base, followed by elaboration to the desired alkylated purine I. Preferably, the metallic murine salt is prepared by reacting the purine with a proton acceptor such as MH where M is lithium, sodium or potassium in a solvent such as DMF or by reacting it with a metal alkoxide of formula MOR where R is methyl, ethyl or t-butyl or the like in an alcohol solvent such as ethanol or t-butanol or a dipolar aprotic solvent such as DMF. The purine salt is dissolved in an inert aprotic solvent such as DMF, and then treated with an appropriate alkylating agent. Alternatively, the purine can be alkylated with the alkylating agent in the presence of a base such as sodium carbonate, potassium carbonate, triethylamine or pyridine. The reaction is run in an inert solvent such as DMF or DMSO at room temperature to the reflux point of the solvent for 1 hour to 72 hours.

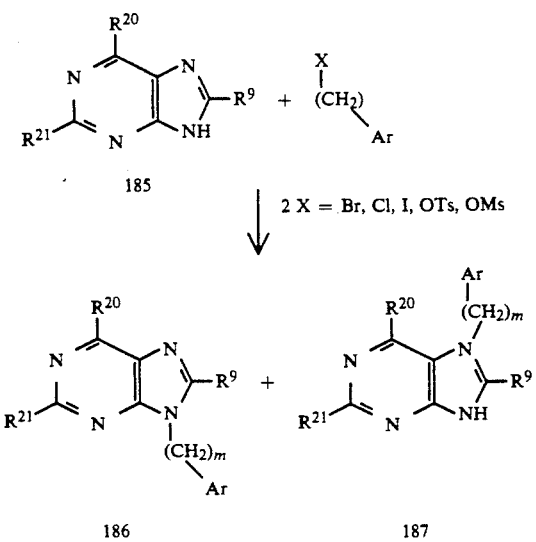

Scheme 38

Generally, compounds of formula 186 can be prepared by direct alkylation onto the purine 185, with an appropriately protected arylmethyl halide, tosylate, mesylate, etc., 2 in the presence of a base as shown in Scheme 38. Preferably, the metallic purine salt is prepared by reacting the purine 185 with a proton acceptor such as MH where M is lithium, sodium or potassium in a solvent such as DMF or by reacting it with a metal alkoxide of formula MOR where R is methyl, ethyl, t-butyl or the like in an alcohol solvent such as ethanol or t-butanol, or a dipolar aprotic solvent such as DMF. The purine salt is dissolved in an inert aprotic solvent such as DMF, and treated with an appropriate alkylating agent 2. Alternatively, purine 185 can be alkylated with an arylmethyl halide (2, where X=Br, Cl, I) in the presence of a base such as sodium carbonate, potassium carbonate, triethylamine or pyridine. The reaction is run in an inert solvent such as DMF or DMSO at room temperature to the reflux temperature of the solvent.

This alkylation procedure produces two compounds 186 and 197, depending on the substituents at $R^{20}$ and $R^{21}$. However, when $R^{21}$=Cl, only one product is isolated, that is the alkylation product 186. When two products are formed they may be separated by chromatography and/or crystallization.

The purines b 185 can be prepared by the procedure of D. S. Acker and J. E. Castle, *J. Chem. Soc.*, 23, 1958 depicted in Scheme 39. This scheme allows for the formation of any of the $R^{21}$ substituents claimed in the scope. The formation of the amidine 188 from the corresponding nitriles is well documented and is obvious to one skilled in the art (also see references in Acker and Castle cited above). Likewise, the nitrile 189 can be prepared containing the substituents claimed in the scope for $R^9$, see Acker and Castle above, and A. J. Zambito, E. E. Howe, *Org. Synth. Coll.*, Vol. V, 373 (1973).

Scheme 39

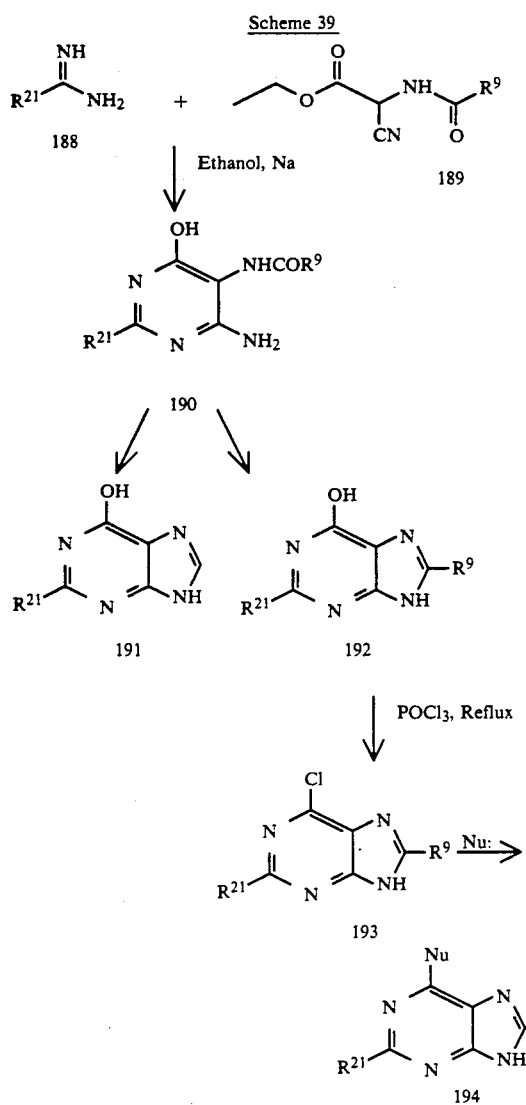

Compound 193 can be converted to compound 194 by treatment with the metallic salt of a nucleophile (Nu:) or with the simple nucleophile itself, such as an amine. This is a general reaction for purines in which halogens (Cl, Br, I) can be easily displaced by a wide variety of nucleophiles, this procedure being illustrated in the work of P. Herdewijn, etc., *Synthesis*, 961 (1989) and K. Tanji, etc., *Chem. Pharm. Bull., Tokyo*, 37(7), 1731 (1989). The resulting compound 194 can be alkylated with compound 2 as shown in Scheme 40 to produce compound 195 and 196 as a mixture of isomers, which can be separated by column chromatography.

Scheme 40

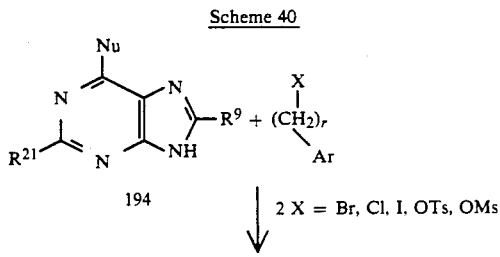

-continued
Scheme 40

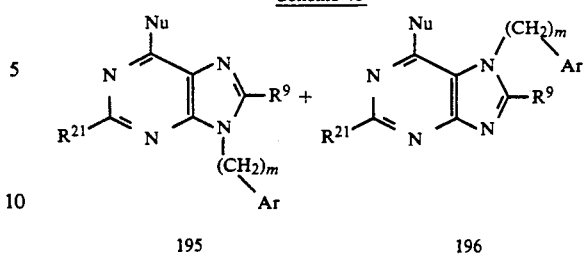

An alternative and preferred method for the preparation of compound 195 is shown in Scheme 41, in which the halopurine 197 is treated with a nucleophile to give the desired compound, using the conditions indicated above.

Scheme 41

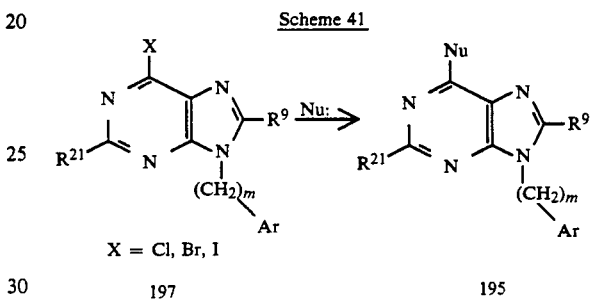

Scheme 42 shows how compounds 193 and 197 are versatile intermediates and can lead to compound 195, where $R^{20}$=Ar=phenyl, or any of the other substituents claimed for $R^{20}$. The procedure involves the coupling of the halides 193 or 197 (X=Br or I), with an ArM, where M=ZnBr, Me$_3$Sn, B(OH)$_2$, etc., in the presence of a transition metal catalyst such as palladium, nickel, platinum, zirconium, etc. (See Scheme 42). A general review of this subject is contained in a paper by K. Undreim and T. Benneche, *Heterocycles*, 30 (2), 1155 (1990), and references therein. In Scheme 43, treatment of the halo purine 193 with a base such as t-BuLi, lithium diisopropylamide (LDA), etc. followed by treatment with a metal source, for purpose of illustration B(OMe)$_3$, produces the metal purine 200. This purine 200 is treated with an aromatic halide, ArX, where X=Br, I, in the presence of a transition metal catalyst, for example, tetrakistriphenylphosphine palladium chloride (or nickel), followed by alkylation of the intermediate compound with compound 2 under previously mentioned conditions to yield the purine 202.

Scheme 42

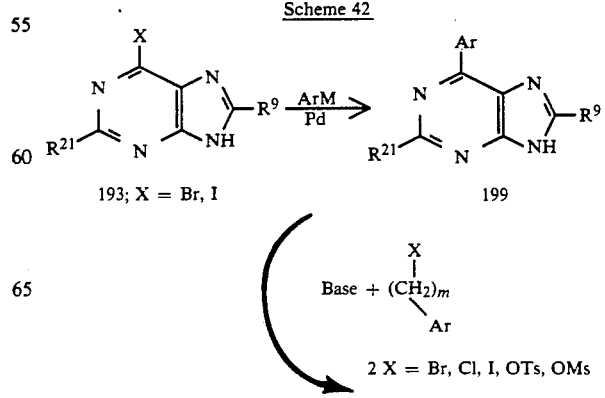

Scheme 42 (-continued)

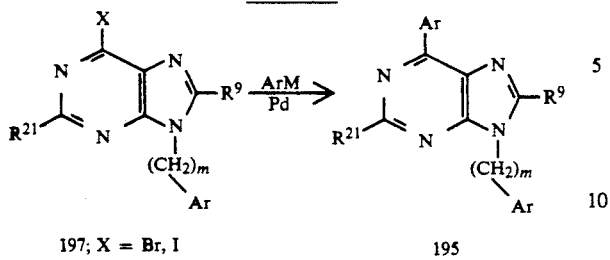

197; X = Br, I    195

An alternate procedure for the preparation of compound 202 involves the treatment of the purine 197, where X=Br, I, with a base such as t-BuLi, LDA, etc., followed by treatment with a metal source, for example, B(OMe)$_3$ or ZnCl$_2$ to yield the purine 201. This compound when treated with ArX, where X=Br, I, in the presence of a transition metal catalyst, i.e., tetrakistriphenylphosphine palladium chloride (or nickel) to yield the desired purine 202 (Scheme 6).

Scheme 43

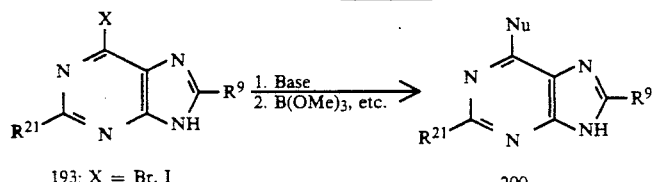

193; X = Br, I    200

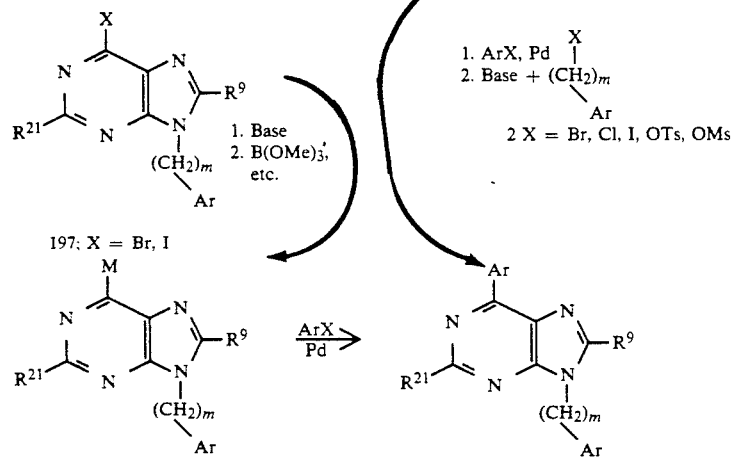

Scheme 44

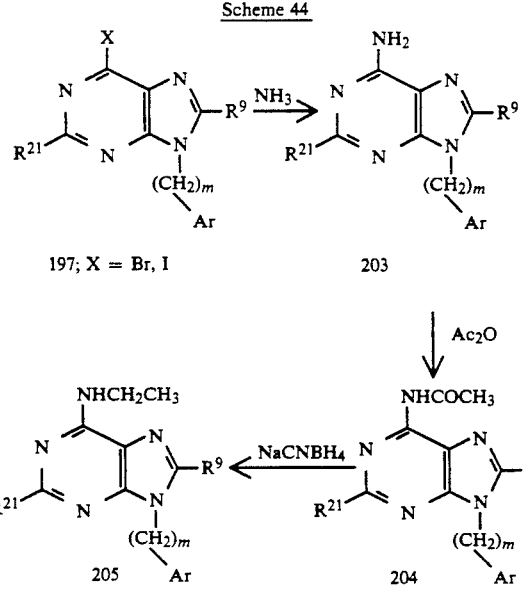

Compounds for which R$^{20}$ has a nitrogen directly attached to the purine ring can be easily prepared from compound 197. Treatment of compound 197 with ammonia produces the amine 203 (Scheme 44).

Treatment of the amine with an anhydride, for example, acetic anhydride yields the amide 204. The amide carbonyl group can be reduced with sodium cyanoborohydride to give the substituted amine 205. These transformations can be seen in Scheme 44. Likewise, other compounds claimed for other R$^{20}$ substituents can be easily prepared by one skilled in the art.

If R$^{20}$≠halogen and R$^{21}$ is halogen, then the nucleophilic displacement chemistry described in Scheme 39, 40, 41 and 44 together with the transition metal catalyzed coupling chemistry described in Schemes 42 and 43, can be applied to introduce the appropriate R$^{21}$ groups in the purines. If both R$^{20}$ and R$^{21}$ are halogens, then the transition metal catalyzed coupling chemistry described in Scheme 42 and 43, can be applied to introduce identical R$^{20}$ and R$^{21}$ groups. If both R$^{20}$ and R$^{21}$ are halogens, then under the appropriate reaction conditions, nucleophiles will displace first the halogen at the R$^{20}$ position and under more vigorous conditions, the halogen at the R$^{21}$ position. Scheme 45 describes the synthesis of halogen-containing purines at the $R^{20}$ and $R^{21}$ positions together with some nucleophilic (nucleophile=Nu:) displacement reactions at those positions. All of the reactions described in Scheme 45. can also be performed on the unalkylated purines (without the —$(CH_2)_m$—Ar group). (Fused Pyrimidines, Part II Purines, D. J. Brown, Editor, Wiley-Interscience, NY, pp. 2-23 (1971)).

Alkyl groups at $R^{20}$ and $R^{21}$ can also be introduced using the nucelophilic displacement chemistry already described in Schemes 39, 40, 41 and 44. Thus, reaction of $R^{20}$ and/or $R^{21}$=Cl 197 with the sodium salt of dimethyl malonate (R=H, for example) yields the malonate derivative 214 which undergoes facile decarboxylation to yield $R^{21}$=methyl derivative 215 (Lettre Naturwiss., 50, 224 (1963)). Likewise, R can be alkyl to yield after decarboxylation the appropriate alkylpurine derivatives (Scheme 46).

Scheme 45

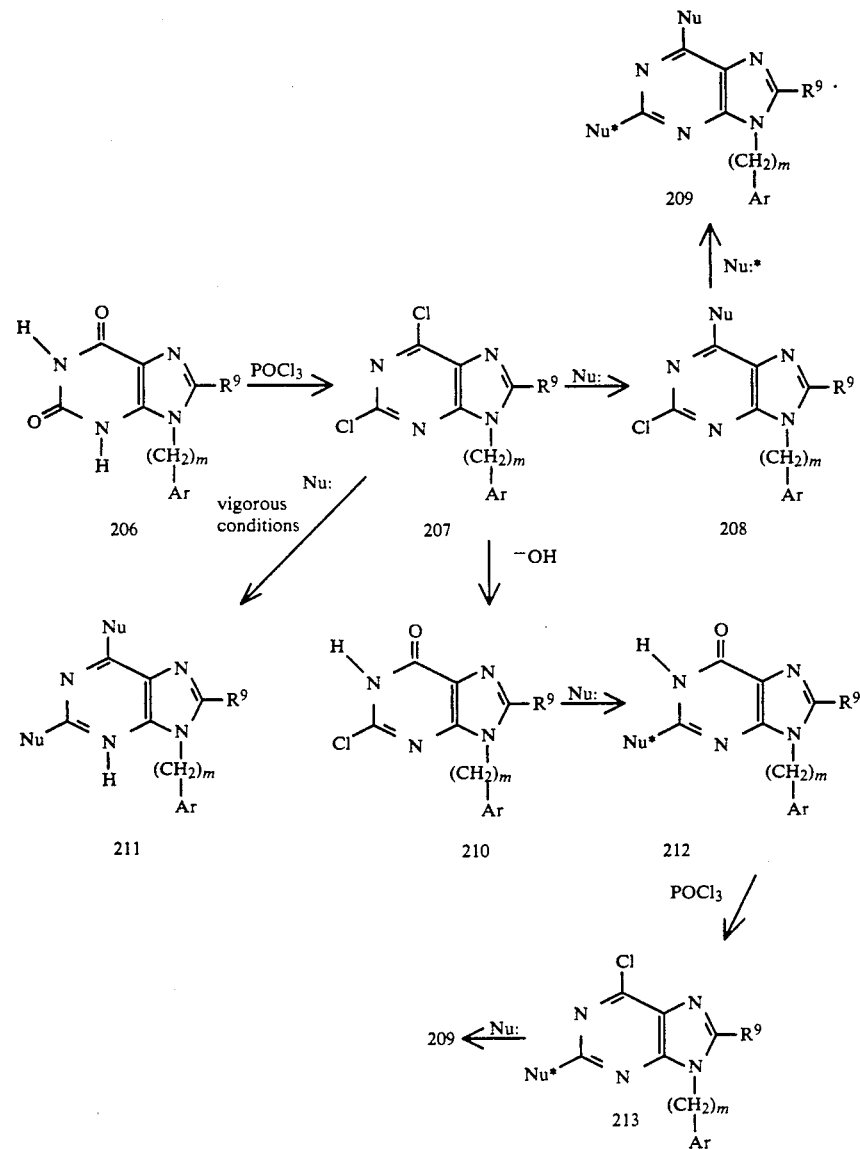

Scheme 46
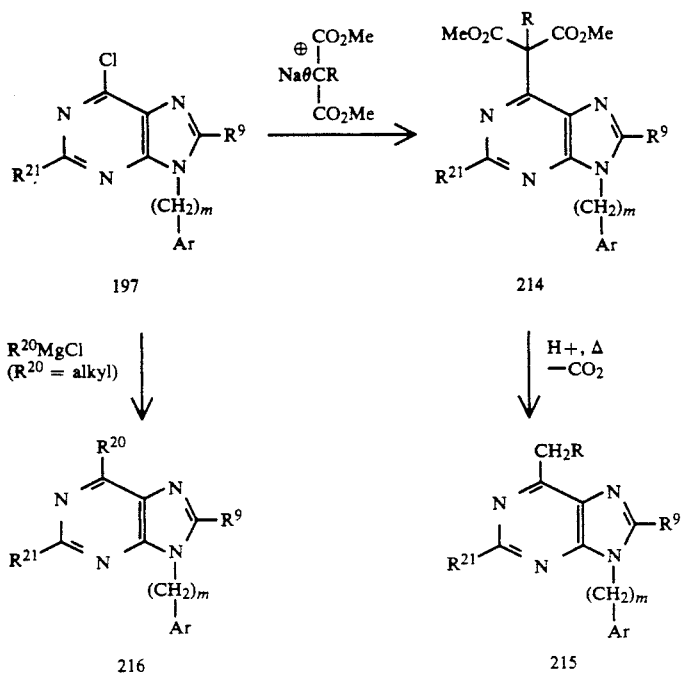
Reaction of chloride 197 ($R^{20}$ and/or $R^{21}$=Cl) with Grignard reagents yields the corresponding adduct 216 where an alkyl group has replaced the chlorine (Shioi, Jap. Pat. 177,356 (1949); (Scheme 46). All of the above reactions can also be done on the unalkylated purine (missing the $(CH_2)_m$Ar group).
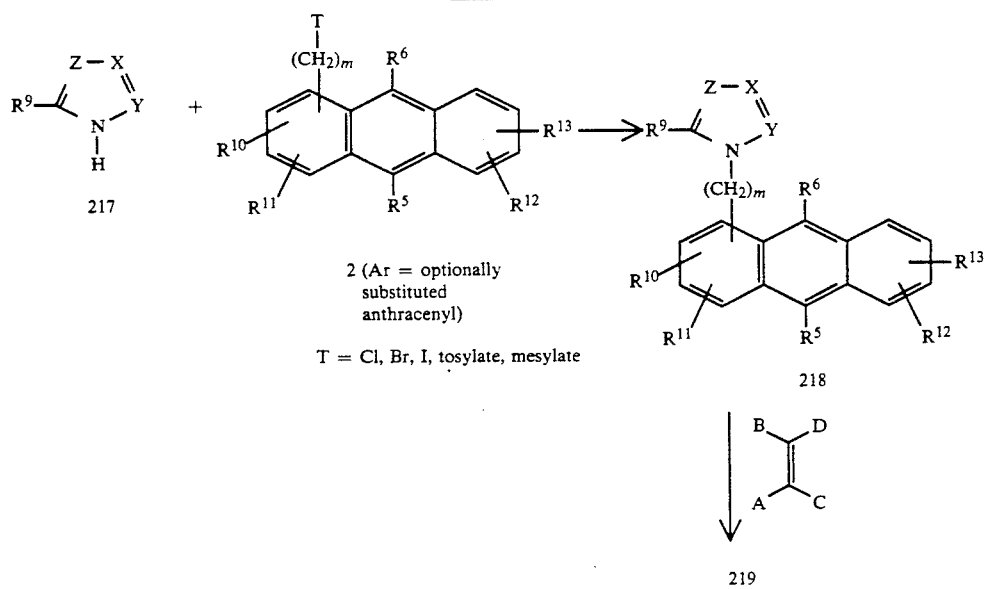

-continued

Scheme 47

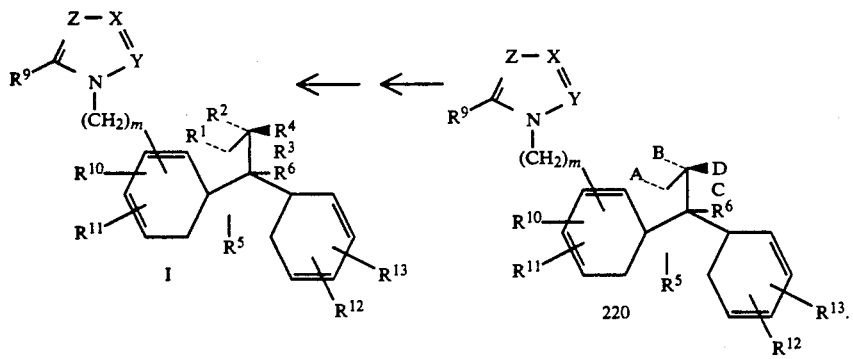

Compounds of formula I are synthesized as shown in Scheme 47. Heterocycle 217 is alkylated under appropriate reaction conditions as discussed several times already in this application with arylmethylhalide, tosylate or mesylate 2 to yield alkylated heterocycle 218. When this aryl=anthracenyl, this anthracene derivative can undergo further reactions around the heterocyclic ring system to further elaborate it or around the anthracene ring system to further elaborate it using methods familiar to one skilled in the art or mentioned already elsewhere in this application. Subsequent Diels-Alder reaction of 218 with dienophile 219 at room temperature to 200° C. with or without an inert solvent such as THF, benzene, toluene, xylenes, glyme, diglyme, DMF, DMSO, alcohols, or water, at atmospheric pressure to several kilobars of pressure will yield adduct 220. The reaction can also be catalyzed with Lewis acids such as $BF_3$, $AlCl_3$, $EtAlCl_2$, $ZnCl_2$, etc. in inert solvents such as methylene chloride, chloroform, etc. A, B, C, and D in adduct 220 can be further elaborated into $R^1$, $R^2$, $R^3$ and $R^4$ of compound I by methods familiar to one skilled in the art. At least one of A, B, C, D must be an electron-withdrawing group such as nitrile, ester, nitro, carboxylic acid, —$CONHOR^{14}$ etc. Diels-Alder reactions of anthracene and anthracene derivatives with electron poor dienophiles is well precedented in the literature and some references are described as follows: maleic anhydride: S. M. Verma, et al., *J. Org. Chem.,* 42, 3736 (1977); citraconic anhydride: Z. Kolodynska, et al., *Acta Pol. Pharm.,* 36, 265 (1979); dimethyl itaconate: M. Kodpinid, et al., *J. Am. Chem. Soc.,* 106, 4862 (1984) and M. Goldlet, et al., *Bull. Soc. Chim. Ft.,* 1158 (1974); acrylates: N. Yamamoto, et al., *Kogyo Kugaku Zasshi,* 69, 928 (1966); $(EtO_2C)_2C=C-(CO_2Et)_2$: J. L. Ripoll, *Bull. Soc. Chim. Fr.,* 11, Pt. 2, 2567 (1974); 1,2-dicyanocyclobutene: D. Bellus, *Helv. Chim. Acta,* 56, 3004 (1973); fumaronitrile: D. T. Mowry, et al., *J. Am. Chem. Soc.,* 69, 573 (1947); diethyl acetylenedicarboxylate: R. J. Giguere, et al., *Tet. Lett.,* 27, 4945 (1986); dimethyl acetylenedicarboxylate: H. P. Figeys, et al., *Tetrahedron,* 28, 3031 (1972); tetracyanoethylene: V. D. Kiselev, et al., *Zh. Org. Khim,* 26, 229 (1990); tetranitroethylene: K. Baum, et al., *J. Org. Chem.,* 50, 2736 (1985); carbomethoxymaleic anhydride: H. K. Hall, Jr., *J. Org. Chem.,* 47, 1451 (1982); 2,2-bistrifluoromethyl-1-cyanoacrylonitrile: W. J. Middleton, *J. Org. Chem.,* 30, 1402 (1965); 1,2-dimethylmaleic anhydride: V. D. Kiselev, et al., *Zh. Org. Khim.,* 22, 1034 (1986) and 21, 1215 (1985); methacrylic acid, methacroylchloride, methacrylonitrile: B. Bacle and G. Levesque, *Polymer Communications,* 28, 36 (1987); mesaconic acid: W. E. Bachmann, *J. Am. Chem.. Soc.,* 70, 1458 (1948).

Functional groups A, B, C, and D of adduct 220 can be subsequently elaborated into $R^1$, $R^2$, $R^3$ and $R^4$, respectively, of compound I. For example, if A is an ester, then saponification will yield a carboxylic acid as $R^1$. It is necessary that at least one of $R^1$, $R^2$, $R^3$ and $R^4$ should be an acidic functionality, as, for example, a carboxylic acid. If A is a nitro group, then catalytic hydrogenation over palladium or platinum in an alcoholic solvent (J. A. Secrist III, et al., *J. Org. Chem.,* 37, 335 (1972)) or homogeneous reduction or Fe/acetic acid reduction will yield an amine. Subsequent reaction with triflic anhydride (K. Kiroyuki, et al., EP 38636A2, October 28, 1981 CA 96:103561Z) will yield $R^1=CF_3SO_2NH-$ which is also acidic. If A is a nitrile, then it can be hydrolyzed by mineral acids such as HCl in the presence of acetic acid at temperatures ranging from 50°-160° C. for 2-48 hours, or by alkali metal hydroxides such as sodium hydroxide or potassium hydroxide to yield the carboxylic acid functionality. A=CN may be reduced by lithium aluminum hydride in THF (H. C. Brown, et al., *J. Am. Chem. Soc.,* 88, 1464 (1966)), or catalytically over Pd or $PtO_2$ (J. A. Secrist III, et al., *J. Org. Chem.,* 37, 335 (1972) or with diborane (H. C. Brown, et al., *J. Am. Chem. Soc.,* 82, 681 (1960)) to yield-$CH_2NH_2$. Reaction with triflic anhydride as before will yield-$CH_2NHSO_2CF_3$.

Compounds where $R^1$ is —$CONHOR^{14}$ may be prepared by the treatment of a carboxylic acid (A=COOH) with 1-4 equivalents of thionyl chloride for 1-10 hours. This reaction can be run without solvent or in a nonreactive solvent such as benzene or chloroform at temperatures of 25°-65° C. The intermediate acid chloride is then treated with 2-10 equivalents of the appropriate amine derivative, $H_2N-OR^{14}$, for 2-18 hours at temperatures of 25°-80° C. in a polar aprotic solvent such as tetrahydrofuran or dimethylsulfoxide to give the hydroxamic acid.

Alternatively, A=carboxylic acid can be converted to the hydroxamic acid according to the procedure in *J. Med. Chem.,* 28, 1158 (1985) by employing dicyclohexylcarbodiimide, 1-hydroxybenzotriazole, and $H_2NOR^{14}$ or according to the procedure described in *Synthesis* 929 (1985) employing the Viismeier reagent and $H_2NOR^{14}$.

Compounds 220 where A=CN may be converted into compound I where $R^1$=tetrazole by a variety of methods using hydrazoic acid. For example, the nitrile is heated with sodium azide and ammonium chloride in DMF at temperatures between 30° C. and reflux for 1-10 days (J. P. Hurwitz, et al., *J. Org. Chem.*, 26, 3392 (1961)). Another procedure is described in European Patent Application 0324377 (5.01.89) (Example 317, for example) where a nitrile is contacted with trialkyltin or triaryl azide Alkyl is defined as normal alkyl of 1-6 carbon atoms. An example of this technique is described also in S. Kozima, et al., *J. Organometallic Chemistry*, 337 (1971). The required trialkyl or triaryltin azides are made from the requisite commercial trialkyl or triaryl tin chloride and sodium azide. The tin azide reagent is reacted with the nitrile in an inert solvent such as THF, toluene, xylenes, etc at 25° C. to reflux for 2-100 hours. The trialkyl or aryl tin-tetrazole adduct can be isolated, sometimes by simple filtration, or destannylated by stirring with aqueous sodium hydroxide or pyridine and the tetrazole group subsequently protected with a trityl group by adding trityl chloride or bromide. The tin salts can be often be washed away from the trityltetrazole adduct. The tetrazole can then be aleprotected (detritylated) using aqueous trifluoroacetic acid or aqueous mineral acid such as HCl.

The tin-tetrazole adduct can also be destannylated using acidic hydrolysis without going through the trityl protection step. All of the above trialkyltin azide chemistry is summarized in J. V. Duncia, et al., *J. Org. Chem.*, 56, 2395 (1991).

Another method for converting A=COOH into $R^1$=CN$_4$H (tetrazole) is described in J. V. Duncia, *J. Org. Chem.*, 56, 2395 (1991). Thus, a carboxylic acid is converted into its N-(β-cyanoethyl)carboxamide via coupling of β-aminopropionitrile with DCC or by conversion first to its acid chloride by procedures familiar to one skilled in the art followed by Schotten-Baumann reaction with β-aminoproprionitrile in aqueous base (1 eq) with or without an organic cosolvent such as THF. This amide is then converted into the corresponding N-(β-cyanoethyl)tetrazole by reaction with Ph$_3$P, diethyl azodicarboxylate (DEAD), and azidotrimethylsilane in an inert solvent such as THF. Subsequent deprotection of the β-cyanoethyl group in aqueous base yields the $R^1$=CN$_4$H (tetrazole) functionality. Compounds where $R^1$=—CONHNHSO$_2$CF$_3$ can be prepared by converting A=COOCH$_3$ or any normal alkyl ester into its hydrazide (A=—CONHNH$_2$) by standard hydrazinolysis. Further reaction with triflic anhydride as described previously yields $R^1$=—CONHNHSO$_2$CF$_3$.

The syntheses of compounds wherein $R^1$ is substituted and unsubstituted 1,2,3-triazoles are described in Scheme 48. Thus, reduction of ester 221 with a reducing agent such as lithium aluminum hydride or diisobutylaluminum hydride gives alcohol 222. Oxidation with pyridinium chlorochromate converts 222 into aldehyde 223. Nitroethylene derivative 224 is prepared by condensation of aldehyde 223 with nitromethane in the presence of a catalyst, R. M. Letchef and M. P. Sammes, *J. Chem. Ed.*, 62, 262 (1985). Reaction of 224 with sodium azide produces the 1,2,3-triazole 225 (N. S. Zefirov, et al., *J. Chem. Soc. Chem. Comm.*, 1001 (1971)).

Aldehyde 227 can also be converted into substituted 1,2,3-triazoles 229 via the sulfone 228, G. Beck. D. Günther, *Chem, Ber.*, 106, 2758 (1973), followed by reaction with sodium azide to give the 1,2,3-triazole 229 where $R^{16}$=CN and CO$_2$$R^{15}$. The nitrotriazole (226; E=NO$_2$) may be synthesized from the substituted triazole 225 via nitration, R. Hüttel, et al., *Chem. Ber.*, 88, 1586 (1955), C. L. Habraken and P. Cohen-Fernandes, *J, Chem. Soc.*, 37 (1972), or from bromonitroethylene derivative 230, G. Kh. Khisamutdinov, et al., *Zh. Org. Khim.*, 11, 2445 (1975), by reaction with sodium azide.

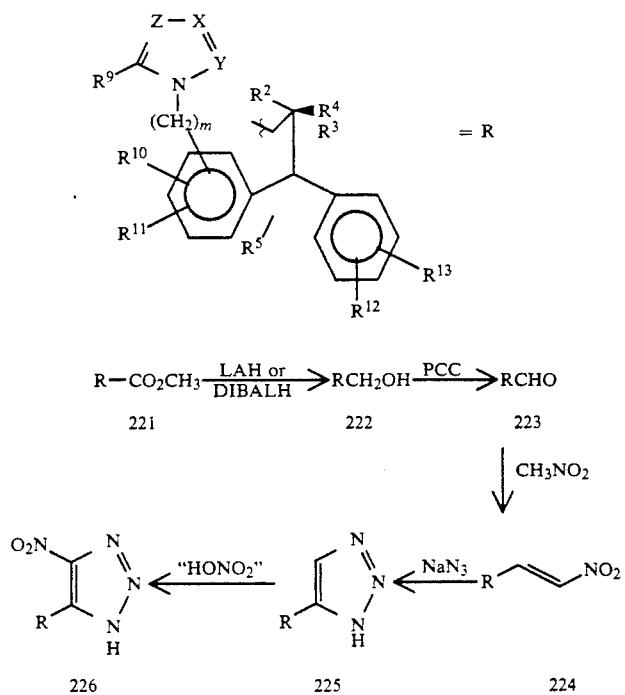

Scheme 48

Scheme 48

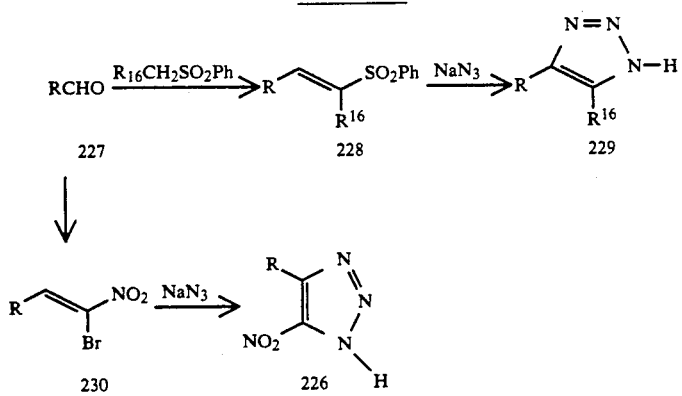

The synthesis of trifluoromethyl-1,2,4-triazoles 235 is depicted in Scheme 49. Acid chloride 232 is converted to amide 2it using standard procedures familiar to one skilled in the art. A preferred protecting group is the 2-propionitrile group. Thus, 233 can be synthesized from 232 and β-aminopropionitrile under Schotten-Baumann like conditions, using aqueous base in an organic solvent to help solubilize 232 and 233 or by the classic DCC coupling procedure. Amide 233 is converted to amidrazone 234 by reaction with $PCl_5$ or phosgene to make an iminoyl chloride which then in turn is reacted with excess hydrazine. Amidrazone 234 is cyclized to the trifluoromethyl-1,2-4-triazole 235 with trifluoroacetic anhydride. The syntheses of the above triazole as well as those of the other 1,2,3-triazoles in Scheme 48 are described in European Patent Application 0324377 (5.01.89).

The N-[tetrazol-5-yl]carboxamide $R^1$ group ($R^1$=—CONHCN$_4$H) may be easily synthesized from A=COOH. Thus the carboxylic acid COOH is converted to its acid chloride by methods familiar to one skilled in the art and then reacted with 5-aminotetrazole under Schotten-Baumann like conditions (1 equivalent of aqueous base with or without an organic cosolvent such as THF) to yield the desired $R^1$=CONHCN$_4$H group.

$R^2$, $R^3$, $R^4$ may be synthesized by the methods previously described for the synthesis of $R^1$.

The compounds of this invention and their preparation can be understood further by the following examples, which do not constitute a limitation of the invention. In these examples, unless otherwise indicated, all temperatures are in degrees centigrade and parts and percentages are by weight.

Scheme 49

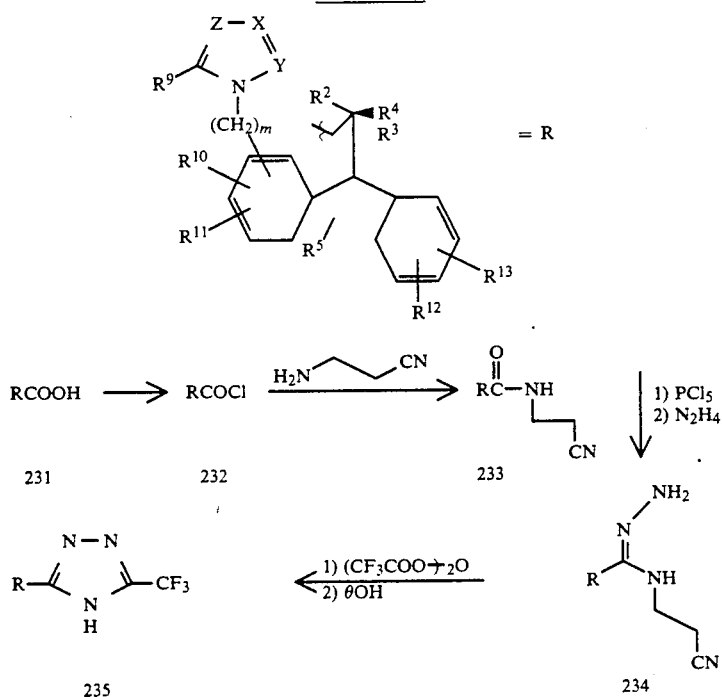

EXAMPLE 1

Part A. Preparation of 2-bromomethylanthracene

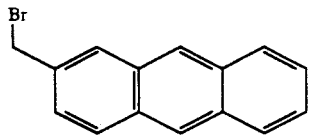

2-Methylanthracene (5.00 g, 26.25 mmol, 1 eq), N-bromosuccinimide (4.70 g, 26.25 mmol, 1 eq), benzoyl peroxide (1.0 g) and carbon tetrachloride (250 mL) were mixed and refluxed for 6 hours. The mixture was cooled to room temperature, and the succinimide precipitate filtered. The filtrate was evaporated to dryness and the residue taken up in ethyl acetate (250 mL) and washed with 1 N NaOH (3×200 mL). The organic layer was dried (MgSO$_4$) and the solvent removed in vacuo to yield 7.77 g of a light brown solid which was used without purification in the next step. NMR (DMSO-d$_6$): δ 4.90 (s, 2H, CH$_2$Br).

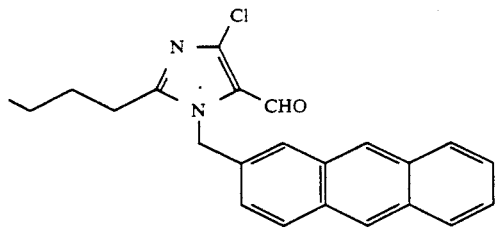

Part B. Preparation of 2-n-Butyl-4-chloro-1-[(anthracen-2-yl) methyl]imidazole-5-carboxaldehyde Sodium hydride (50% dispersion in oil, 1.37 g, 28.6 mmol, 1.1 eq) was added to a DMF solution (50 mL) containing 2-n-butyl-4-chloroimidazole-5-carboxaldehyde (prepared as in European Patent Application Number 89100144.8, published 7.19.89) (4.85 g, 26.0 mmol, 1.0 eq). The contents were heated with stirring at 60° C. until everything was dissolved. The reaction was then cooled to 0° C. and a DMF solution (75 mL) of 2-bromomethylanthracene (entire contents from the previous step: 7.77 g of impure material, theoretically 26.0 mmol, 1.0 eq) was added and the entire contents stirred at room temperature overnight. The solvent was removed in vacuo and the residue flash chromatographed in 9:1 toluene/ethyl acetate to 75:25 toluene/ethyl acetate to yield 3.73 g of an amber glass. This material could not be crystallized and was used without further purification for the next step. NMR (CDCl$_3$): δ 9.80 (s, 1H); 8.40 (s, 1H); 8.33 (s, 1H); 7.98 (m, 3H); 7.48 (m, 3H); 7.23 (m, 1H); 5.72 (s, 2H); 2.79 (t, 2H, J=7Hz); 1.69 (t of t, 2H, J=7,7Hz); 1.33 (t of q, 2H, J=7,7Hz); 0.84 (t, 3H, J=7Hz).

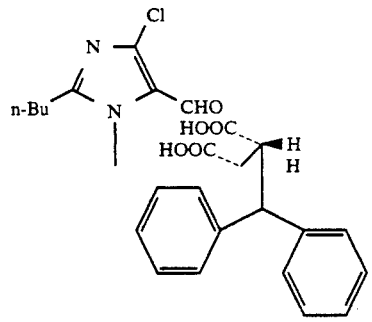

and

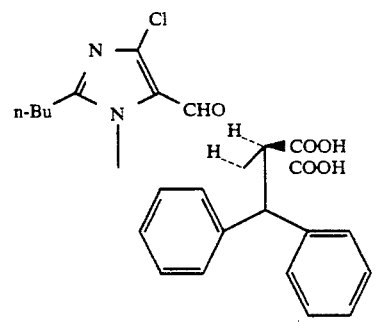

Part C. Preparation of (±)-cis-2-[(2-n-butyl-4-chloro-5-formylimidazol-1-yl)methyl]-9,10-dihydro-9,10-ethanoanthracene-11,12-dicarboxylic acid, a mixture of endo and oxo isomers 2-n-Butyl-4-chloro-1-[(anthracen-2-yl)methyl]imidazole-5-carboxaldehyde (0.5 g, 1.3 mmol, 1 eq), maleic anhydride (0.13 g, 1.3 mmol, 1 eq) and toluene (2 mL) were mixed and refluxed 24 hours. TLC shows two products. The reaction mixture was diluted with THF (5 mL) followed by 1.000 N NaOH (2.6 mL, 2.6 mmol, 2 eq). The mixture was stirred at room temperature for 5 hours after which the THF was removed in vacuo, the aqueous layer diluted with water (50 mL) and then extracted with ethyl ether (3×50 mL). The aqueous layer was then acidified to pH=3 with conc. HCl and a gummy precipitate formed. This precipitate was dissolved with ethyl acetate (50 mL) and the layers were separated. The aqueous layer was further extracted with ethyl acetate (2×50 mL), the ethyl acetate layers were collected, dried (MgSO$_4$) and the solvent removed in vacuo to yield 420 mg of an off-white solid. Recrystallization from hexane/ethyl acetate yielded a white solid (223 mg): mp 144.5°–146.0° C. NMR (DMSO-d$_6$): δ 66 (s, 1H), 7.40–6.69 (m, 7H); 5.52 (s, 2H); 4.57 (s, 2H); 2.98 (s, 2H); 2.55 (t, 2H, J=7Hz); 1.48 (t of t, 2H, J=7,7Hz); 1.20 (t of q, 2H, J=7,THz); 0.71 (t, 3H, J=7Hz). HPLC detects a 3:1 ratio of isomers.

EXAMPLE 2

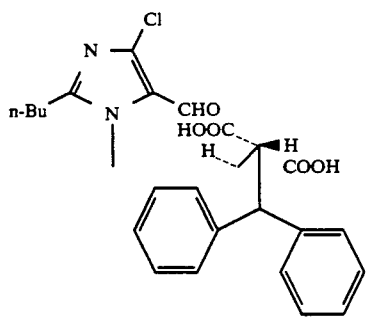

and

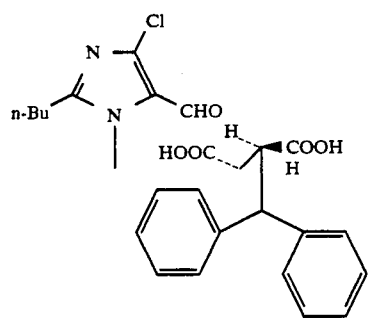

Preparation of
(±)-trans-2-[(2-n-butyl-4-chloro-5-formylimidazol-1-yl)methyl]-9,10-dihydro-9,10-ethanoanthracene-11,12-dicarboxylic acids, both diastereomers.

2-n-Butyl-4-chloro-1-[(anthracen-2-yl)methyl]imidazole-5-carboxaldehyde (1.00 g, 2.65 mmol, eq), dimethylfumarate (0.38 g, 2.65 mmol, 1 eq) and toluene (10 mL) were mixed and refluxed for 24 hours. Another 1 eq of dimethylfumarate was added and the reaction was refluxed for an additional 24 hours. The reaction was cooled to room temperature, diluted with THF (10 mL) and 1.000 N NaOH was added (5.3 mL, 5.3 mmol, 2 eq). After 24 hours of stirring at room temperature, another 2 eq of 1.000 N NaOH was added and the mixture was allowed to stir at room temperature for hours. The reaction was still incomplete, so that 2 more eq of 1.000 N NaOH was added and the reaction was allowed to stir for another 72 hours. The organic solvents were removed in vacuo and the basic aqueous layer was washed with ethyl ether (3×25 mL). The basic aqueous layer was acidified with concentrated HCl and the resultant solids dissolved in ethyl acetate (50 mL). The phases were separated and the aqueous layer was extracted with ethyl acetate (2×50 mL). The ethyl acetate layers were combined, dried (MgSO4), and the solvent removed in vacuo to yield an amber glass (740 mg).

The two diastereomers were separated by HPLC (column: Dynamax Silica; Solvent: 90% hexane, 10% of the following mixture-97.5% isopropanol, 2.5% dioxane, 0.1% trifluoroacetic acid) yielding a faster eluting isomer (isomer A) as a yellow solid (235 mg) and a slower eluting isomer (198 mg) as a yellow glass (isomer B).

Isomer A was recrystallized by dissolving in ethyl ether, adding hexane and ethyl acetate to yield 105 mg of a white powder: mp 215.0°-216.0° C. dec. NMR (DMSO-$d_6$): δ 12.62 (bm, 2H); 9.68 (s, 1H); 7.46-6.98 (m, 6H); 6.82 (d, 1H, J=9Hz); 5.53 (s, 2H); 4.58 (s, 2H); 3.04 (s, 2H); 2.58 (t, 2H, J=7Hz); 1.47 (t of t, 2H, J=7, 7Hz); 1.18 (t of q, 2H, J=7,7Hz); 0.71 (t, 3H, J=7Hz). Anal. calcd. for $C_{27}H_{25}ClN_2O_5$: C, 63.47; H, 5.33; N, 5.48. Found: C, 63.39; H, 5.05; N, 5.33.

Isomer B was crystallized by the above procedure to yield 79 mg of a white powder: mp 195° C. dec. NMR (DMSO-$d_6$): δ (12.62, bm, 2H); 9.67 (s, 1H); 7.44-7.02 (m, 6H); 6.82 (d, 1H, J=9Hz); 5.53 (s, 2H); 4.70 (s, 2H); 3.07 (s, 2H); 2.60 (t, 2H, J=7Hz); 1.44 (t of t, 2H, J=7,7Hz); 1.17 (t of q, 2H, J=7,7Hz); 0.70 (t, 3H, J=7Hz).

EXAMPLE 3

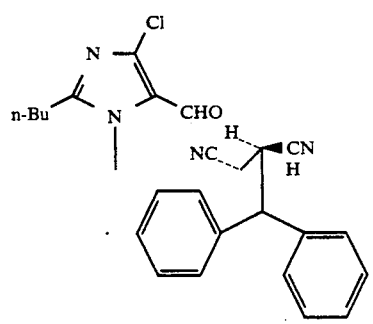

and

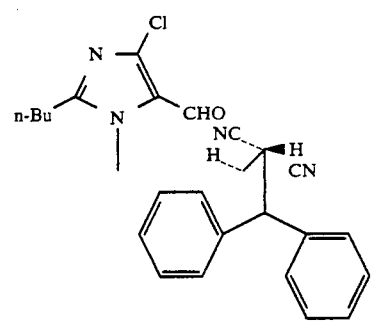

Part A. Preparation of
(i)-trans-2-[(2-n-butyl-4-chloro-5-formylimidazol-1-yl)methyl]-9,10-dihydro-9,10-ethanoanthracene-11,12-dicarbonitrile, both diastereomers 2-n-Butyl-4-chloro-1-[(anthracen-2-yl)methyl]imidazole-5-carboxaldehyde (2.00 g, 5.31 mmol, 1 eq), fumaronitrile (0.41 g, 5.31 mmol, 1 eq), and xylenes (20 mL) were mixed and refluxed under nitrogen for 24 hours. The following day, more fumaronitrile (2 eq), was added and the mixture was refluxed for another 24 hours. The solvents were removed in vacuo and the residue flash chromatographed in 75:25 hexane:ethyl acetate to yield 1.75 g of a yellow glass. $^1$H NMR shows a 9:1 ratio of diastereomers. NMR (major isomer only) (DMSO-$d_6$): δ 9.66 (s, 1H); 7.65-6.80 (m, 7H); 5.59 (s, 2H); 4.90-4.75 (m, 2H); 3.70-3.50 (m, 2H); 2.60 (t, 2H, J=7Hz); 1.60-1.30 (m, 2H); 0.70 (t, 3H, J=7Hz). Anal. calcd. for $C_{27}H_{23}ClN_4O.H_2O)_{0.9}$: C, 68.83; H, 5.31; N, 11.89. Found: C, 68.92; H, 5.01; N, 11.51.

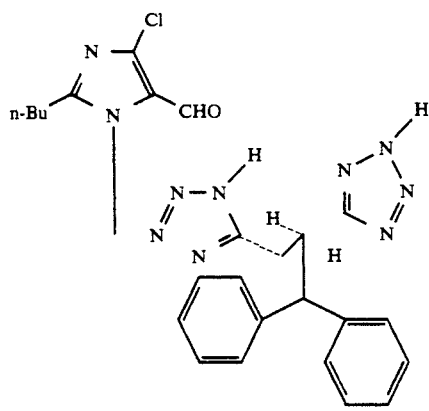

and

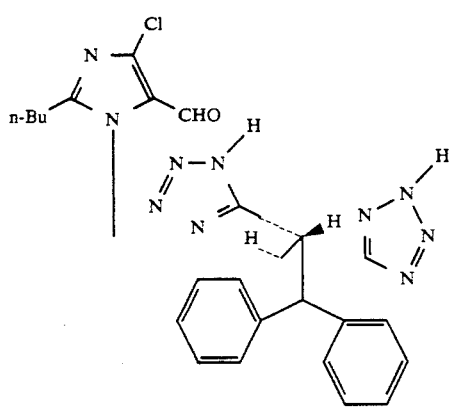

Part B. Preparation of
(±)-trans-2-[(2-n-butyl-4-chloro-5-formylimidazol-1-yl)methyl]-9,10-dihydro-9,10-ethano-11,12-bis (1H-tetrazol-5-yl)anthracene, both diastereomers (±)-trans-2-[(2-n-butyl-4-chloro-5-formylimidazol-1-yl)methyl]-9,10-dihydro-9,10-ethanoanthracene-11,12-dicarbonitrile, both diastereomers (0.5 g, 1.10 mmol), 1 eq), sodium azide (0.14 g, 2.20 mmol, 2 eq, tributyltin chloride (0.60 mL, 2.20 mmol, 2 eq), and xylenes (3 mL) were mixed and refluxed for 16 hours. Pyridine (0.098 mL, 1.21 mmol, 1.1 eq) was added and the mixture was stirred for 0.5 hour at room temperature. Afterwards, trityl chloride (337 mg, 1.21 mmol, 1.1 eq) was added and the mixture was stirred at room temperature for 2 hours. More pyridine was added (1.1 eq) and after 0.5 hour more trityl chloride (1.1 eq) was added. After 0.5 hour, the mixture became a clear brown solution. Water (100 mL) and ethyl acetate (100 mL) were added and the phases separated. The organic layer was washed with water (2×100 mL), tested for azide and found to be negative (See J. V. Duncia, et al., *J. Org. Chem.*, 56, 2395 (1991)) dried (MgSO$_4$) and the solvent removed in vacuo to yield the bis tritylated product. This residue was dissolved in THF (50 mL) and 3.6 N HCl (6.22 mL) was added. The reaction was stirred at room temperature overnight. The pH was adjusted to 12 with 10 N NaOH and the organic solvent removed in vacuo. The remaining aqueous layer was extracted with ethyl ether (3×50 mL) and then acidified to pH=2 with concentrated HCl. The resultant solids were filtered and dried under high vacuum to yield 350 mg of a light brown solid: mp 214° C. dec. HPLC shows a 9:1 mixture of diastereomers. NMR (DMSO-d$_6$): δ 7.30 (d, 1H, J=7Hz); 7.30–6.92 (m, 4H); 6.88 (d, 1H, J=7Hz); 6.85–6.70 (m, 1H); 5.70–5.50 (m, 1H); 5.45 (s, 1H); 5.00–4.80 (m, 2H); 4.25–4.00 (m, 2H); 2.70–2.30 (m, 2H); 1.60–1.00 (m, 4H); 0.80–0.50 (m, 3H). Titration with 1.000 N NaOH shows the presence of exactly 2 acidic functional groups. Anal. calcd. for C$_{27}$H$_{25}$ClN$_{10}$O.(H$_2$O): C, 58.00; H, 4.87; Cl, 6.34. Found: C, 57.71; H, 4.53; Cl, 6.25.

EXAMPLE 4

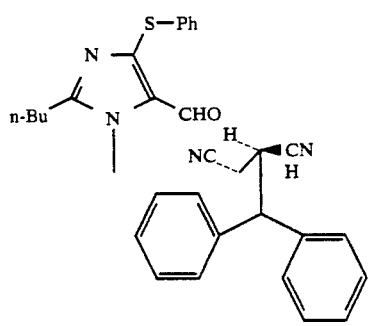

and

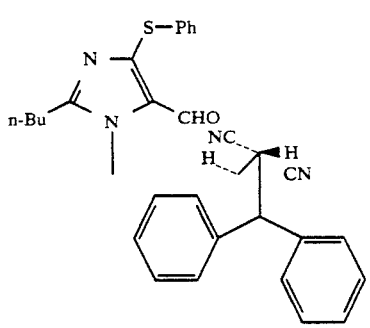

Part A. Preparation of
(±)-trans-[(2-n-butyl-4-phenylthio-5-formylimidazol-1-yl)
methyl]-9,10-dihydro-9,10-enthanoanthracene-11,12-dicarbonitrile, both diastereomers (±)-trans-2-[(2-n-Butyl-4-chloro-5-formylimidazol-1-yl)methyl]-9,10-dihydro-9,10-ethanoanthracene-11,12-dicarbonitrile, both diastereomers (1.04 g, 2.29 mmol, 1 eq), thiophenol (2.35 mL, 22.9 mmol, 10 eq) and sodium methoxide in methanol (0.53 g Na, 22.9 mmol, 10 eq in 50 mL MeOH) were mixed and refluxed overnight under nitrogen. The solvent was removed in vacuo and the residue flash chromatographed over silica gel in 9:1 pentane: ethyl acetate to 75:25 ethyl acetate: pentane. Two fractions were obtained, both yielding yellow glasses.

The faster eluting isomer yielded 520 mg: NMR (DMSO-d$_6$): δ 9.80 (d, 1H, J=7Hz); 7.70–7.10 (m, 11H); 6.96 (t, 1H, J=7Hz); 5.61 (s, 1H); 4.86 (s, 2H); 3.61 (s, 2H); 2.61 (t, 2H, J=7Hz); 1.46 (t of t, 2H, J=7,7Hz); 1.30–1.00 (m, 2H); 0.80–0.60 (m, 3H). Anal. calcd. for C$_{33}$H$_{28}$N$_4$OS.(H$_2$O)$_{0.75}$.(PhSH)$_{0.2}$: C, 72.80; H, 5.48; N, 9.93; S, 6.82. Found: C, 72.98; H, 5.17; N, 9.60; S, 6.86.

The slower eluting isomer yielded 270 rag: NMR (DMSO-d$_6$): δ 9.81 ( d, 1H, J=7Hz); 7.70–7.16 (m, 9H); 7.13 (s, 1H); 7.02 (d, 1H, J=7Hz); 6.90 (d, 1H, J=7Hz ); 5.66 (s, 1H); 5.57 (s, 1H); 4.87 (s, 2H); 3.72 (s, 2H);

2.70–2.55 (m, 2H); 1.46 (t of t, 2H, J=7,7Hz); 1.30–1.00 (m, 2H); 0.80–0.60 (m, 3H). Anal. calcd. for $C_{33}H_{28}N_4OS \cdot (H_2O)_{0.75} \cdot (PhSH)_{0.2}$: C, 72.80; H, 5.48; N, 9.93; S, 6.82. Found: C, 73.15; H, 5.12; N, 9.73; 6.94.

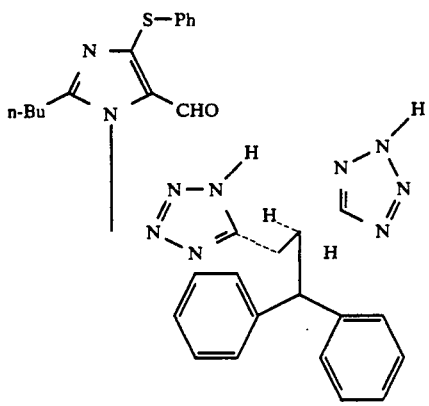

or

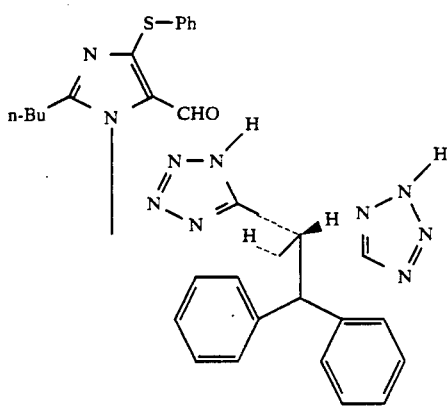

Part B. Preparation of (±)-trans-2-[(2-n-butyl-4-phenylthio-5-formylimidazol-1-yl) methyl]-9,10-dihydro-9,10-ethano-11,12-bis (1H-tetrazol-5-yl) anthracene: one diastereomer (±)-trans-2-[(2-n-Butyl-4-chloro-5-formylimidazol-1-yl)methyl]-9,10-dihydro-9,10-ethanoanthracene-11,12-dicarbonitrile, the faster eluting diastereomer (450 mg) was converted to the bistetrazole product by the method described in Example 3, Part B to yield 370 mg of an orange glass: HPLC shows essentially one peak. NMR shows a 1:1 mixture of aldehyde rotamers: NMR (DMSO-$d_6$) (key peaks only): δ 9.82 (s, 1×0.5H); 9.77 (s, 1×0.5H); 5.52 (m, 2H); 4.92 (m, 2H); 4.13 (m, 2H); 2.58 (t, 2×0.5H, J=7Hz); 2.46 (t, 2×0.5H, J=7Hz); 0.70 (t, 2×0.5H, J=7Hz); 0.63 (t, 3×0.5H, J=7Hz). Anal. calcd. for $C_{33}H_{30}N_{10}OS \cdot$(ethyl acetate)$_{0.9} \cdot (H_2O)_{0.2}$: C, 63.01; H, 5.43; S, 4.60. Found: C, 63.06; H, 5.36; S, 4.34.

The following compounds listed in Table 1 can or could be prepared by the procedures described in Examples 1 through 4 from the appropriate anthracenylalkyl alkylated heterocycle described heretofore and the appropriate anthracene dienophiles which function as latent acidic functional groups:

TABLE 1

| Ex. No. | Structure | mp (°C.) |
|---|---|---|
| 5 | 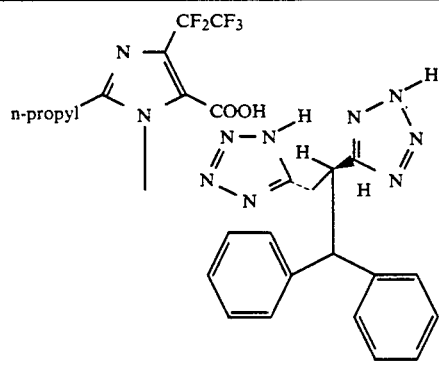 | |

TABLE 1-continued

| Ex. No. | Structure | mp (°C.) |
|---|---|---|
| 6 | 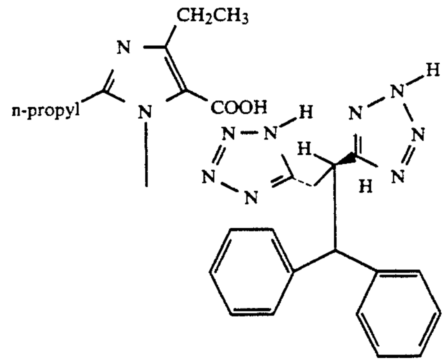 | |
| 7 | 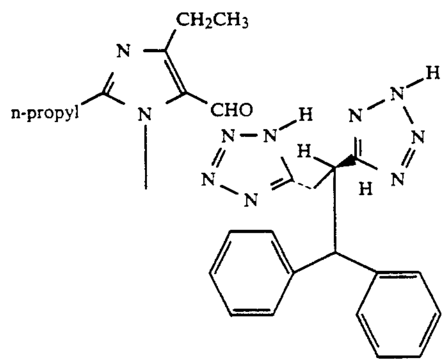 | |
| 8 | 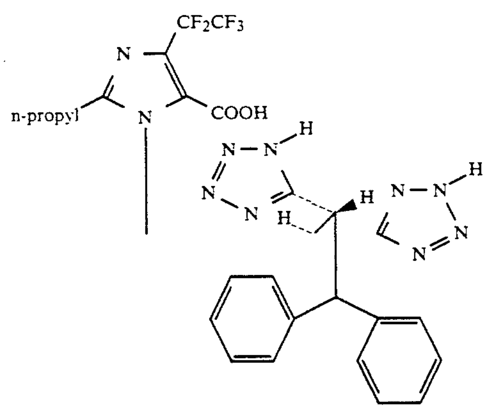 | |
| 9 | 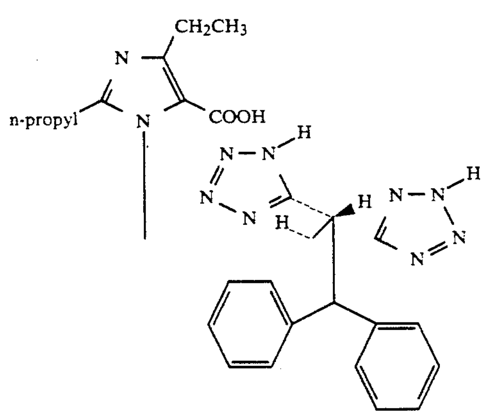 | |

TABLE 1-continued

| Ex. No. | Structure | mp (°C.) |
|---|---|---|
| 10 | 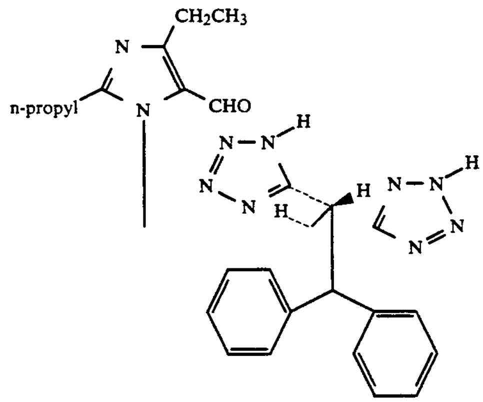 | |
| 11 | 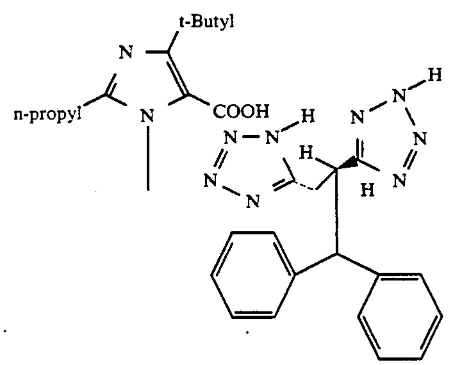 | |
| 12 | 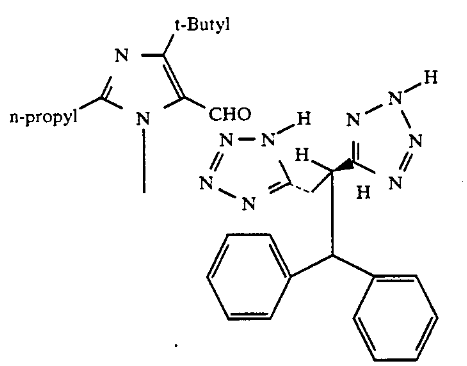 | |
| 13 | 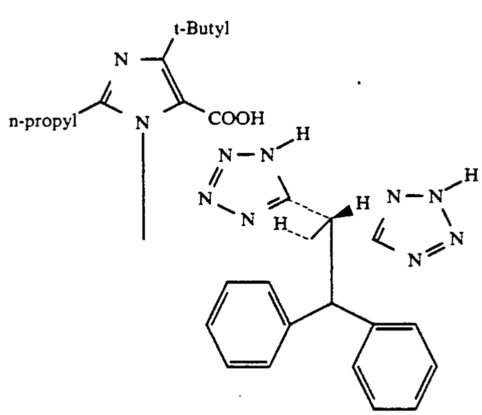 | |

TABLE 1-continued

| Ex. No. | Structure | mp (°C.) |
|---|---|---|
| 14 | 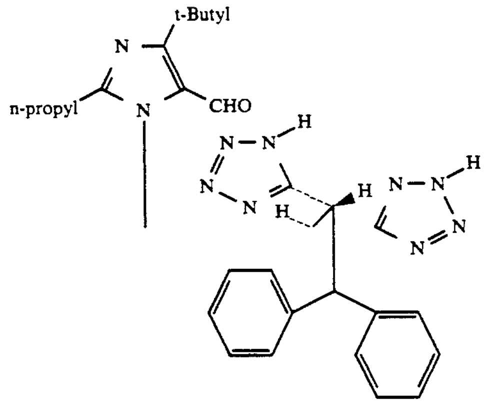 | |
| 15 | 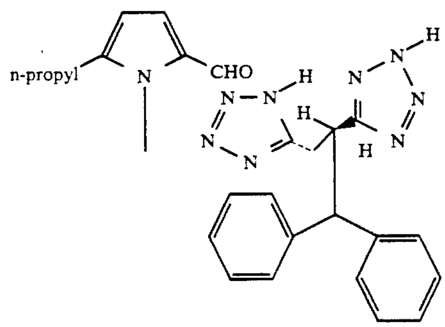 | |
| 16 | 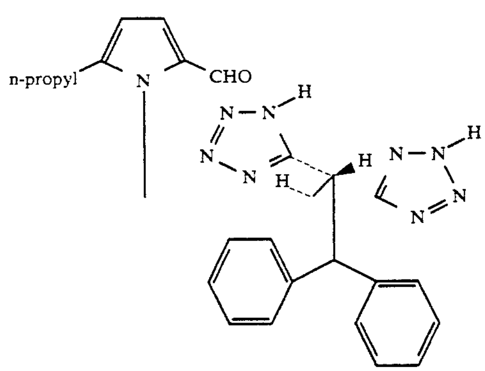 | |
| 17 | 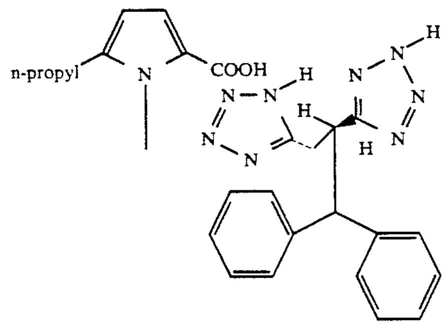 | |

| Ex. No. | Structure | mp (°C.) |
|---|---|---|
| 18 | (structure: 5-n-propyl-1-methyl-pyrrole-2-COOH with tetrazole-CH(tetrazole)-CH(diphenylmethyl) substituent) | |
| 19 | (structure: 5-n-propyl-1-methyl-3-CH₂CH₃-pyrrole-2-CHO with tetrazole-CH₂-C(tetrazole)=CH(diphenylmethyl) substituent) | |
| 20 | (structure: 5-n-propyl-1-methyl-3-CH₂CH₃-pyrrole-2-CHO with bis-tetrazole diphenylmethyl substituent) | |
| 21 | (structure: 5-n-propyl-1-methyl-3-CH₂CH₃-pyrrole-2-COOH with tetrazole-CH₂-C(tetrazole)=CH(diphenylmethyl) substituent) | |

TABLE 1-continued

| Ex. No. | Structure | mp (°C.) |
|---|---|---|
| 22 | (structure) | |
| 23 | (structure) | |
| 24 | (structure) | |
| 25 | (structure) | |

TABLE 1-continued

| Ex. No. | Structure | mp (°C.) |
|---|---|---|
| 26 | 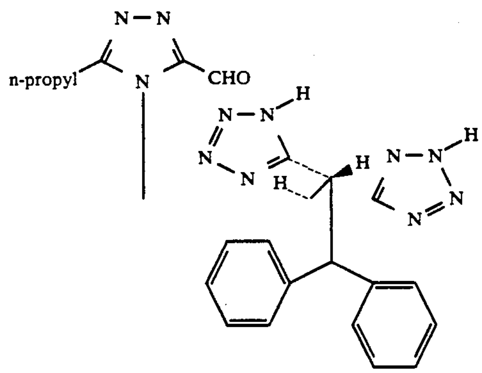 | |
| 27 | 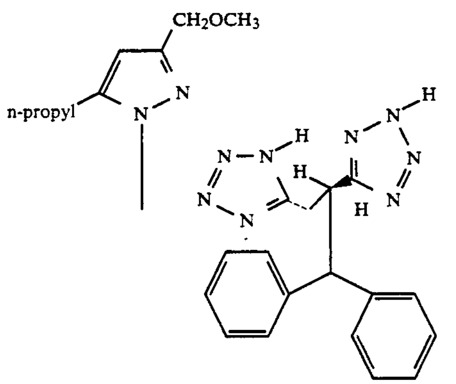 | |
| 28 | 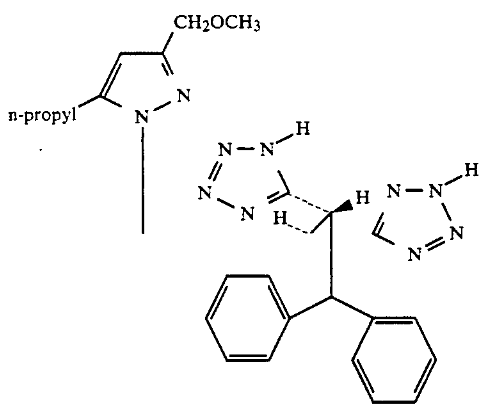 | |
| 29 | 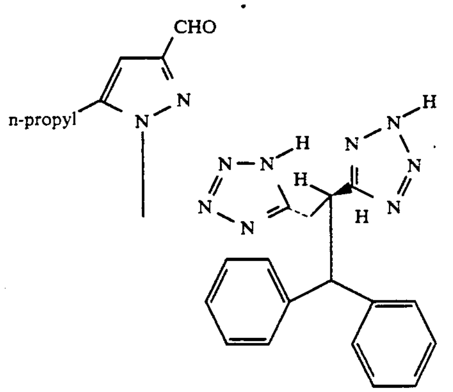 | |

TABLE 1-continued

| Ex. No. | Structure | mp (°C.) |
|---|---|---|
| 30 | 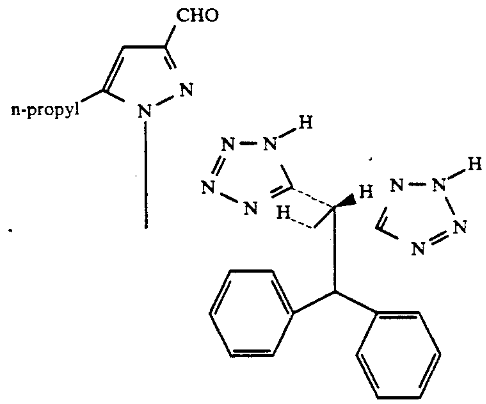 | |
| 31 | 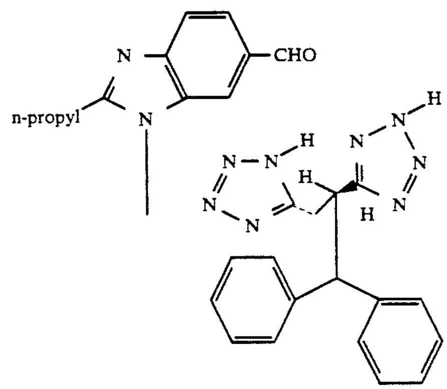 | |
| 32 | 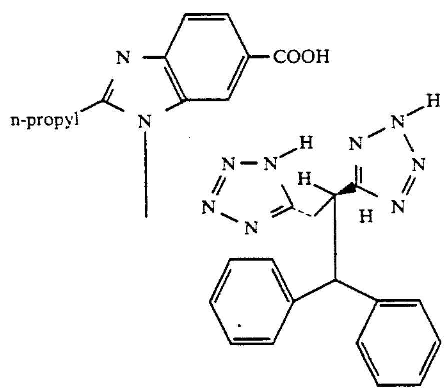 | |
| 33 | 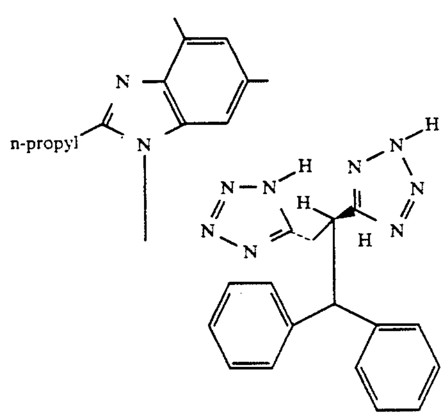 | |

TABLE 1-continued

| Ex. No. | Structure | mp (°C.) |
|---|---|---|
| 34 | (2-n-propyl-6-CHO-benzimidazole N-substituted with CH2-C(H)(tetrazole)-C(H)(tetrazole)-CH(phenyl)2 structure) | |
| 35 | (2-n-propyl-6-COOH-benzimidazole N-substituted with CH2-C(H)(tetrazole)-C(H)(tetrazole)-CH(phenyl)2 structure) | |
| 36 | (2-n-propyl-5,7-dimethyl-benzimidazole N-substituted with CH2-C(H)(tetrazole)-C(H)(tetrazole)-CH(phenyl)2 structure) | |
| 37 | (2-n-propyl-4-Cl-5-CHO-imidazole N-substituted with CH2-C(CH3)(tetrazole)-C(CH3)(tetrazole)-CH(phenyl)2 structure) | |

TABLE 1-continued
| Ex. No. | Structure | mp (°C.) |
|---|---|---|
| 38 | 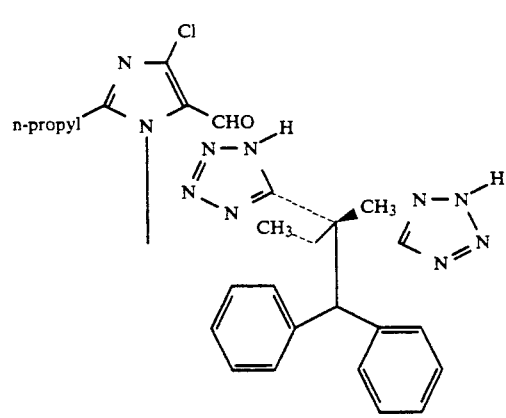 | |
| 39 | 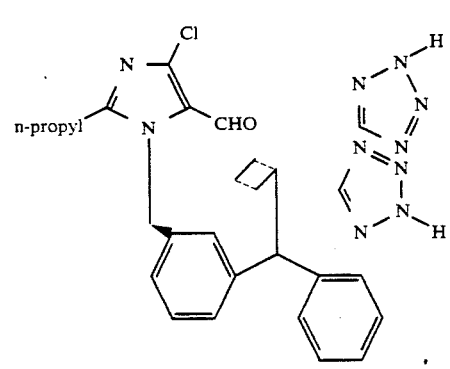 | |
| 40 | 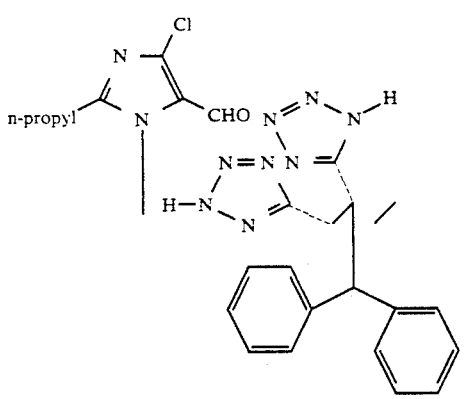 | |
| 41 | 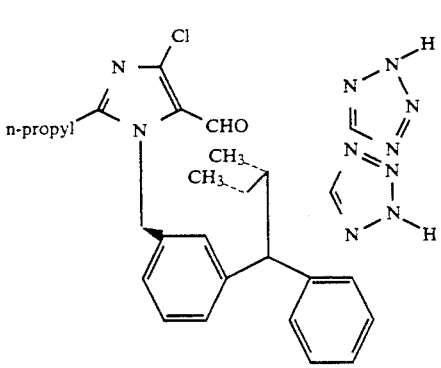 | |

TABLE 1-continued

| Ex. No. | Structure | mp (°C.) |
| --- | --- | --- |
| 42 | 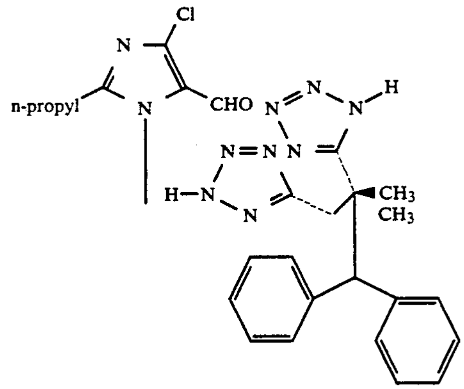 | |
| 43 | 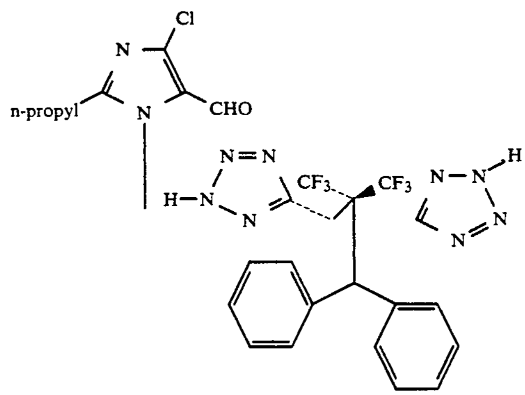 | |
| 44 | 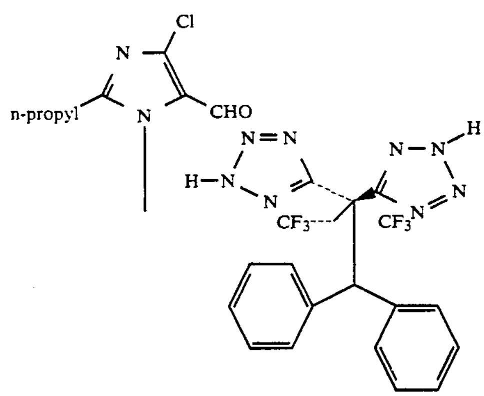 | |
| 45 | 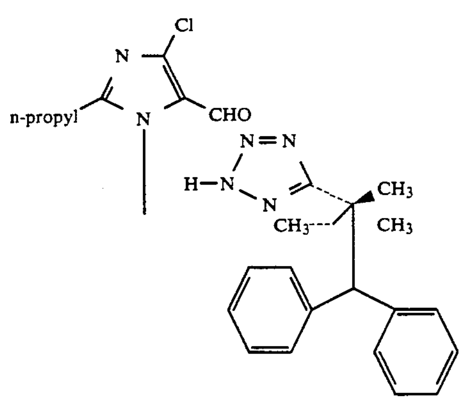 | |

TABLE 1-continued

| Ex. No. | Structure | mp (°C.) |
|---|---|---|
| 46 | 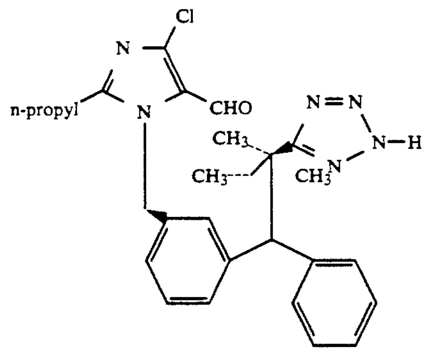 | |
| 47 | | |
| 48 | | |
| 49 | | |

TABLE 1-continued
| Ex. No. | Structure | mp (°C.) |
|---|---|---|
| 50 | 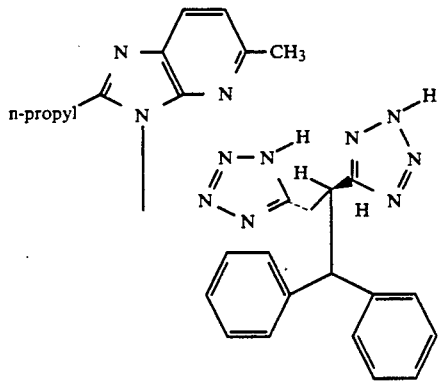 | |
| 51 | 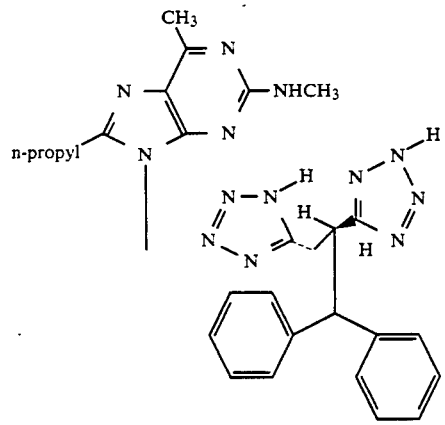 | |
| 52 | 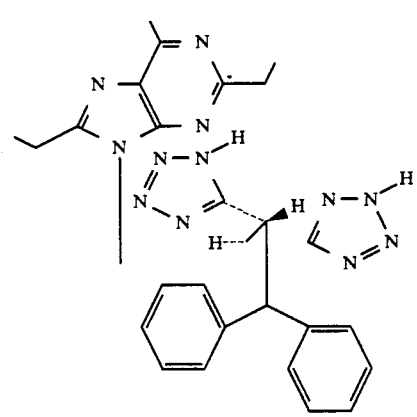 | |

TABLE 1-continued
| Ex. No. | Structure | mp (°C.) |
|---|---|---|
| 53 | 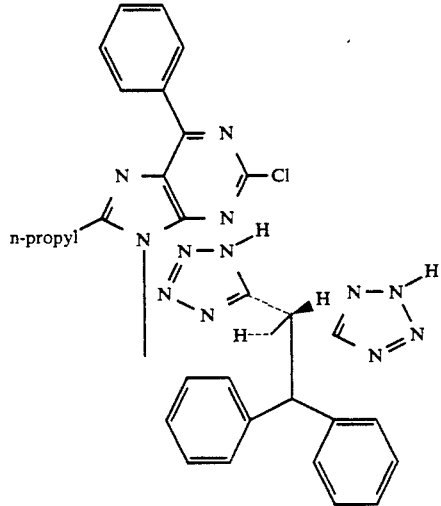 | |
| 54 | 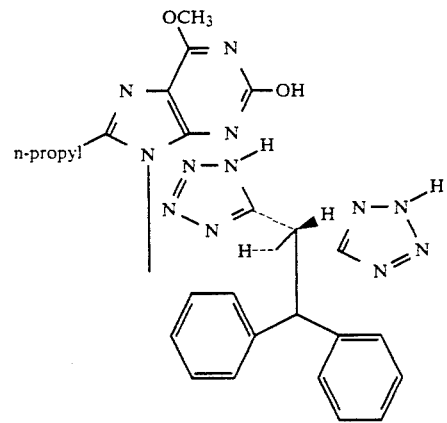 | |
| 55 | 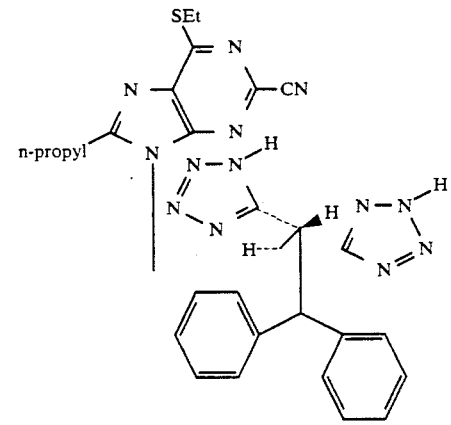 | |

TABLE 1-continued
| Ex. No. | Structure | mp (°C.) |
|---------|-----------|----------|
| 56 | 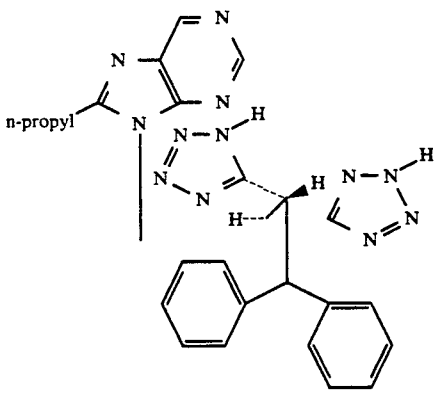 | |
| 57 | 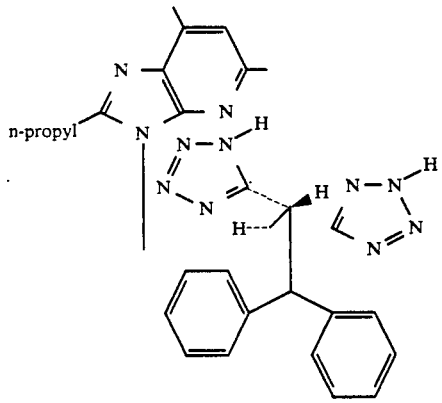 | |
| 58 | 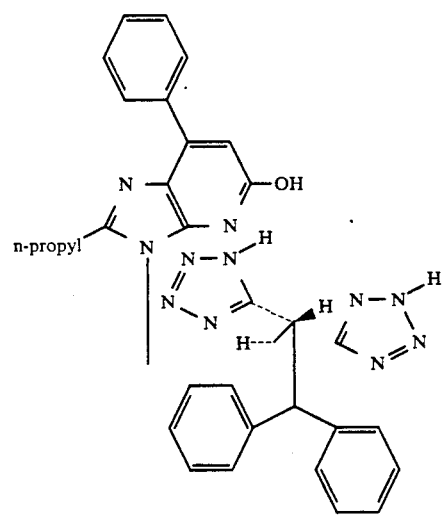 | |

TABLE 1-continued

| Ex. No. | Structure | mp (°C.) |
|---|---|---|
| 59 | (imidazopyridine with ethyl, phenylthio, n-propyl, N-methyl; bistetrazole diphenylmethyl side chain) | |
| 60 | (methyl-imidazopyridine, n-propyl, N-methyl; bistetrazole diphenylmethyl side chain) | |
| 61 | (5-chloro-4-CHO-imidazole, n-propyl, N-methyl; CH$_3$ONHCO / CONHOCH$_3$ diphenylmethyl side chain) | |
| 62 | (5-chloro-4-CHO-imidazole, n-propyl, N-methyl; CF$_3$SO$_2$NHNHCO / CONHNHSO$_2$CF$_3$ diphenylmethyl side chain) | |

TABLE 1-continued

| Ex. No. | Structure | mp (°C.) |
|---|---|---|
| 63 | (imidazole with Cl, n-propyl, N-methyl, CHO; substituent: CF3SO2NH—CH(H)—CH(NHSO2CF3)—CH(phenyl)(phenyl)) | |
| 64 | (imidazole with Cl, n-propyl, CHO; N-benzyl with m-substituted CH(H)—C(CF3)(CF3)—CH2NHSO2CF3 and phenyl) | |
| 65 | (imidazole with Cl, n-propyl, CHO; N-benzyl with m-substituted CH2—CH(phenyl)—CO—NH-tetrazole) | |
| 66 | (imidazole with Cl, n-propyl, CHO; N-benzyl with m-substituted CH2—CH(phenyl)—triazole-CF3) | |

TABLE 1-continued

| Ex. No. | Structure | mp (°C.) |
|---|---|---|
| 67 | (imidazole with Cl, CHO, n-propyl, N-CH2-phenyl-CH(CH2-triazole-CN)-phenyl) | |
| 68 | (imidazole with Cl, CHO, n-propyl, N-CH2-phenyl-CH(CH2-triazole-CO2CH3)-phenyl) | |
| 69 | (imidazole with Cl, CHO, n-propyl, N-(CH2)2-CH(tetrazole)(CH2-tetrazole)-CH(phenyl)2) | |
| 70 | (imidazole with Cl, CHO, n-propyl, N-(CH2)2-C(CH3)(tetrazole)-C(CH3)(tetrazole)-CH(phenyl)2) | |

[a] NMR(DMSO-d6) δ 9.70–9.60(m, 1H); 7.85–6.80(m, 7H); 5.54(s, 2H); 4.97(s, 1H); 4.81(s, 1H); 2.70–2.40(m, 2H); 1.70–1.00(m, 8H); 0.75–0.50(m, 3H).
[b] NMR(DMSO-d6) δ 9.70–9.60(m, 1H); 7.73(d, 1H, J=8Hz); 7.60–7.40(m, 6H); 5.65–5.48(m, 3H); 5.30–5.10(m, 1H); 1.60–0.50(m, 9H).
[c] NMR(DMSO-d6) δ 9.7(m, 1H); 8.2–6.8(m, 7H); 5.8–5.4(m, 2H); 4.4(m, 1H); 4.2(m, 1H); 2.9–2.4(m, 4H); 2.32(s, 2H × 0.46); 2.26(s, 2H × 0.37); 2.20(s, 2H × 0.17); 1.63(m, 2H); 1.30(m, 2H); 0.83(m, 3H).

UTILITY

The hormone angiotensin II (AII) produces numerous biological responses, e.g., vasoconstriction, through stimulation of its receptors on cell membranes. For the purpose of identifying compounds such as AII antagonists which are capable of interacting with the AII receptor, a ligand-receptor binding assay was utilized for the initial screen. The assay was carried out according to the method described by Glossmann, et al., *J. Biol. Chem.*, 249, 825 (1974), but with some modifications. The reaction mixture contained rat adrenal cortical microsomes (source of AII receptor) in Tris buffer and 2 nM of $^3$H-AII or 0.05 nM $^{125}$I-AII with or without potential AII antagonist. This mixture was incubated for 1 hour at room temperature and the reaction was subsequently terminated by rapid filtration and rinsing through glass micro-fibre filter. Receptor-bound $^3$H-AII or $^{125}$I-AII trapped in filter was quantitated by scintillation counting. The inhibitory concentration (IC$_{50}$) of potential AII antagonist which gives 50% displacement of the total specifically bound $^3$H-AII or $^{125}$I-AII is a measure of the affinity of such compound for the AII receptor. Compounds of this invention which were tested in this binding assay exhibited IC$_{50}$ of $10^{-5}$ M or less (Table 2).

The potential antihypertensive effects of the compounds of this invention may be demonstrated by administering the compounds to awake rats made hypertensive by ligation of the left renal artery (Cangiano, et al., *J. Pharmacol. Exp Ther.*, 208, 310 (1979)). This procedure increases blood pressure by increasing renin production with consequent elevation of AII levels. Compounds are administered intravenously via a cannula in the jugular vein at 3 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds which were tested. Some compounds of this invention exhibited intravenous activity at 3 mg/kg (Table 2).

TABLE 2

| Ex. No. | Angiotensin II Receptor Binding IC$_{50}$ (μmolar) | Antihypertensive Effects in Renal Hypertensive Rats Intravenous Activity |
|---|---|---|
| 1 | 1.1 | + |
| 2A | 0.22 | + |
| 2B | 0.32 | + |
| 3 | 0.092 | + |
| 4 | 0.46 | + |
| 47 | 0.50 | * |
| 48 | 3.0 | * |
| 49 | 0.50 | * |

\+ Significant decrease in blood pressure at 10 mg/kg or less
\* No decrease in blood pressure at 10 mg/kg dosage tested.

The compounds of this invention can be administered for the treatment of hypertension according to the invention by any means that effects contact of the active ingredient compound with the site of action in the body of a warm-blooded animal. For example, administration can be parenteral, i.e., subcutaneous intravenous, intramuscular, or intraperitoneal. Alternatively, or concurrently, in some cases, administration can be by the oral route.

The compounds can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenoloi, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methylchlorothiazide, methyldopa, methyldopate hydrochloride, minoxidil, parglyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teptrotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 rag) chlorothiazide (125-2000 rag), ethacrynic acid (15-200 rag), amiloride (5-20 rag), furosemide (5-80 rag), propranolol (20-480 rag), timolol maleate (5-60 rag), nifedipine (5-60 rag), and nitrendipine (5-60 rag). In addition, triple drug combinations of hydrochlorothiazide (15-200 rag)plus amiloride (5-20 rag) plus angiotensin II antagonist of this invention (3-200 mg) or hydrochlorothiazide (15-200 mg) plus timolol maleate (5-60) plus an angiotensin II antagonist of this invention (0.5-250 rag)or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

The compounds of this invention also exhibit central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

Further, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's *Pharmaceutical Sciences*, A. Osol, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

injectable

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs. Suitable dosages, dosage forms and administration routes are illustrated in the following tables.

| Examples of NSAID's that can be combined with AII blockers of this invention: | | | |
|---|---|---|---|
| Drug | Dose (mg) | Formulation | Route |
| Indomethacin | 25 (¾ times daily) | Tablet | Oral |
| Meclofenamate | 50–100 (¾ times daily) | Tablet | Oral |
| Ibuprofen | 300–400 (¾ times daily) | Tablet | Oral |
| Piroxicam | 10–20 (¼ times daily) | Tablet | Oral |
| Sulindac | 150–200 (2 times daily) | Tablet | Oral |
| Azapropazone | 200–500 | Tablet | Oral |

| Examples of NSAID's that can be combined with AII blockers of this invention: | | | |
|---|---|---|---|
| Drug | Dose (mg) | Formulation | Route |
| | (¾ times daily) | | |

| Examples of diuretics that can be combined with AII blockers of this invention: | | | |
|---|---|---|---|
| Drug | Dose (mg) | Formulation | Route |
| Benzothiadizides (e.g. hydrochlorothiazide) | 25-100 (daily) | Tablet | Oral |
| Loop diuretics (e.g. furosemide) | 50-80 (daily) | Tablet | Oral |

When used with an NSAID, the dosage of AII blockers will generally be the same as when the AII blocker is used alone, i.e., 1-500 milligrams per day, ordinarily from 10 to 100 milligrams per day in one or more applications. When used with diuretics, the initial dose of AII blocker can be less, e.g., 1-100 milligrams per day and for the more active compounds 1-10 milligrams per day.

It is expected that the compounds of this invention will also be useful in the treatment of chronic renal failure.

We claim:

1. A compound of formula I:

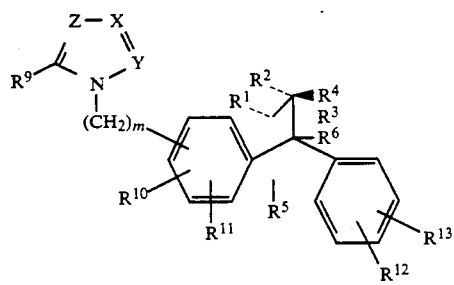

wherein $R^1$, $R^2$, $R^3$, and $R^4$ are independently —H, —COOH, —CONHOR$^{14}$; —CONHNHSO$_2$CF$_3$; —NHSO$_2$CF$_3$; —CH$_2$NHSO$_2$CF$_3$;

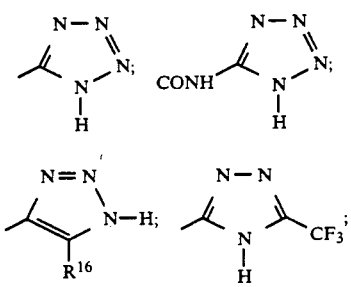

alkyl of 1 to 5 carbon atoms; perfluoroalkyl of 1 to 5 carbon atoms; CN, —CO$_2$R$^{15}$, phenyl; or where $R^1$ and $R^2$ or $R^3$ and $R^4$ are taken together to form an aliphatic ring of 3 to 6 carbon atoms; provided that at least one of $R^1$, $R^2$, $R^3$, and $R^4$ is always an acidic group defined by —COOH, —CONHOR$^{14}$;

—CONHNHSO$_2$CF$_3$; —NHSO$_2$CF$_3$; —CH$_2$NHSO$_2$CF$_3$;

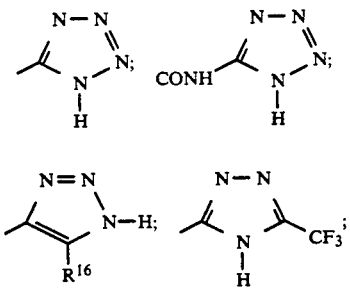

and further provided that if Z, X and Y are not all N then at least one of $R^1$-$R^4$ or $R^{10}$-$R^{13}$ is always a tetrazolyl group as defined by

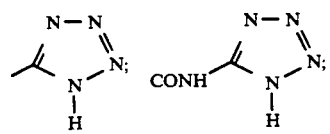

$R^5$ and $R^6$ are independently H, CH$_3$, Cl, Br, I, F, —OCH$_3$, —OCOCH$_3$;

$R^7$ is H, F, Cl, Br, I, NO$_2$, perfluoroalkyl of 1 to 5 carbon atoms; CN; COR$^{17}$; straight or branched alkyl of 1 to 6 carbon atoms; phenyl; phenylthio; alkenyl of 2 to 10 carbon atoms; alkynyl of 2 to 10 carbon atoms; phenylalkenyl where the alkenyl portion is 2 to 6 carbon atoms; phenylalkynyl where the alkynyl portion is 2 to 6 carbon atoms; heteroaryl selected from 2- and 3-thienyl, 2- and 3-furyl, and substituted phenyl, phenylalkenyl, phenylalkynyl, and heteroaryl selected from 2- and 3-thienyl, 2- and 3-furyl substituted with one or two substituents selected from halogen, alkoxy of 1 to 5 carbon atoms, alkyl of 1 to 5 carbon atoms, —NO$_2$, —CN, —CF$_3$, —COR$^{15}$, —CH$_2$OR$^{18}$, and —NHCOR$^{18}$ where R$^{18}$ is other than H; 1- or 2-naphthyl; 2-, 3-, 4-, 5-, 6-, or 7-benzofuryl, unsubstituted or substituted with one or two substituents selected from halogen, alkoxy of 1 to 5 carbon atoms, alkyl or 1 to 5 carbon atoms, —NO$_2$, —CN, —CF$_3$, —COR$^{15}$, —CH$_2$OR$^{18}$, and —NHCOR$^{18}$ where R$^{18}$ is other than H;

$R^8$ is H; CN; COR$^{17}$; —(CH$_2$)$_{n-1}$CH(OR$^{18}$)R$^{19}$; —(CH$_2$)$_n$O(CO)R$^{18}$ where R$^{18}$ is other than H; —(CH$_2$)$_n$COR$^{17}$;

$R^9$ is alkyl of 2 to 6 carbon atoms; alkenyl or alkynyl of 2 to 6 carbon atoms; cycloalkyl of 3 to 8 carbon atoms; cycloalkylalkyl of 4 to 8 carbon atoms; alkylthio where the alkyl portion is of 2 to 5 carbon atoms;

$R^{10}$, $R^{11}$, $R^{12}$, $R^{13}$ are independently H, Cl, Br, I, F, NO$_2$, CN, OH, alkyl of 1 to 4 carbon atoms; alkylcarbonyloxy of 1 to 4 carbon atoms; alkoxy of 1 to 4 carbon atoms; —CO$_2$H; —CO$_2$R$^{15}$; —NHSO$_2$CF$_3$; —CONHOR$^{14}$; phenyl;

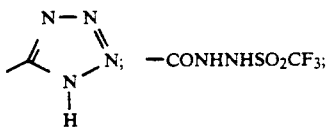 —CONHNHSO$_2$CF$_3$;

R$^{14}$ is H, methyl or benzyl;
R$^{15}$ is H; alkyl of 1 to 5 carbon atoms; branched alkyl of 1 to 5 carbon atoms; phenyl;
R$^{16}$ is CN, NO$_2$ or CO$_2$R$^{15}$;
R$^{17}$ is H, alkyl of 1 to 6 carbon atoms; —OR$^{15}$, —NR$^{18}$R$^{19}$;
R$^{18}$ and R$^{19}$ are independently H, alkyl of 1 to 5 carbon atoms; phenyl;
R$^{20}$ and R$^{21}$ are independently —H; Cl; Br; I; —SR$^{15}$; —R$^{17}$; —CN; —OR$^{15}$; phenyl; substituted phenyl where the substituents are alkoxy of 1 to 5 carbon atoms, alkyl of 1 to 5 carbon atoms, fluorine;
Z is N; CH;
X is C-R$^7$; C-R$^8$; N;
Y is C-R$^8$; C-R$^7$; N;
X and Y are carbon atoms and Z is N when they are part of the following ring system;

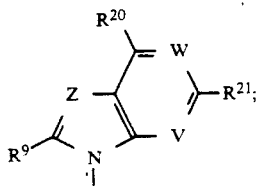

V is CH or N when W is CH;
W is CH or N when V is CH;
m is 1,2;
n is 1–5.

2. A compound of claim 1 wherein
R$^1$, R$^2$, R$^3$, and R$^4$ are independently —H, —COOH, —CONHOR$^{14}$;

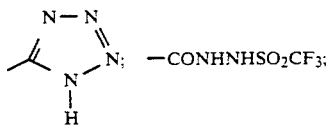 —CONHNHSO$_2$CF$_3$;

alkyl of 1 to 5 carbon atoms; perfluoroalkyl of 1 to 5 carbon atoms; CN, —CO$_2$R$^{15}$, or where R$^1$ and R$^2$ or R$^3$ and R$^4$ are taken together to form a carbocyclic ring of 3 to 6 carbon atoms; provided that at least one of R$^1$, R$^2$, R$^3$ and R$^4$ is always an acidic group defined by

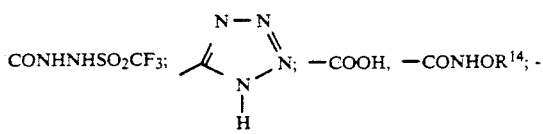

R$^5$ and R$^6$ are independently H; —CH$_3$; —OCH$_3$;
R$^7$ is H, F, Cl, Br, I, NO$_2$, perfluoroalkyl of 1 to 5 carbon atoms; —COR$^{17}$; straight or branched alkyl of 1 to 6 carbon atoms; phenyl; phenylthio; alkenyl of 2 to 10 carbon atoms; alkynyl of 2 to 10 carbon atoms; phenylalkenyl where the alkenyl portion is 2 to 6 carbon atoms; phenylalkynyl where the alkynyl portion is 2 to 6 carbon atoms; heteroaryl selected from 2- and 3-thienyl, 2- and 3-furyl, and substituted phenyl, phenylalkenyl, phenylalkynyl, and heteroaryl selected from 2- and 3-thienyl, 2- and 3-furyl substituted with one or two substituents selected from halogen, alkoxy of 1 to 5 carbon atoms, alkyl of 1 to 5 carbon atoms, —NO$_2$, —CN, —CF$_3$, —COR$^{15}$, —CH$_2$OR$^{18}$, and —NHCOR$^{18}$ where R$^{18}$ is other than H; 1-or 2-naphthyl; 2-, 3-, 4-, 5-, 6-, or 7-benzofuryl, unsubstituted or substituted with one or two substituents selected from halogen, alkoxy of 1 to 5 carbon atoms, and alkyl of 1 to 5 carbon atoms;
R$^8$ is H, —COR$^{17}$, —(CH$_2$)$_{n-1}$CH(OR$^{18}$)R$^{19}$; —(CH$_2$)$_n$O(CO)R$^{18}$ where R$^{18}$ is other than H; —(CH$_2$)$_n$COR$^{17}$;
R$^9$ is alkyl of 2 to 6 carbon atoms; alkenyl or alkynyl of 2 to 6 carbon atoms; alkylthio where the alkyl portion is of 2 to 5 carbon atoms;
R$^{10}$, R$^{11}$, R$^{12}$, R$^{13}$ are independently H, Cl, Br, F, alkyl of 1 to 4 carbon atoms; alkoxy of 1 to 4 carbon atoms;
R$^{14}$ is H, methyl or benzyl;
R$^{15}$ is H; alkyl of 1 to 5 carbon atoms; branched alkyl of 1 to 5 carbon atoms; phenyl;
R$^{16}$ is CN, NO$_2$, or CO$_2$R$^{15}$;
R$^{17}$ is H, alkyl of 1 to 6 carbon atoms; —OR$^{15}$; —NR$^{18}$R$^{19}$;
R$^{18}$ and R$^{19}$ are independently H, alkyl of 1 to 5 carbon atoms; phenyl;
R$^{20}$ and R$^{21}$ are independently —H; Cl; Br; I; —SR$^{15}$; —R$^{17}$; —CN; —OR$^{15}$; phenyl; substituted phenyl where the substituents are alkoxy of 1 to 5 carbon atoms, alkyl of 1 to 5 carbon atoms, fluorine;
Z is N; CH;
X is C-R$^7$; C-R$^8$; N;
Y is C-R$^8$; C-R$^7$; N;
X and Y are carbon atoms and Z is N when they are part of the following ring system;

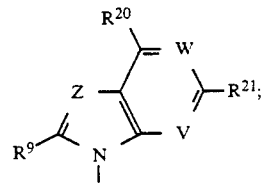

V is CH or N when W is CH;
W is CH or N when V is CH;
m = 1
n — 1–5.

3. A compound of claim 2 wherein:
R$^1$, R$^2$, R$^3$, and R$^4$ are independently —H, —COOH, —CONHOR$^{14}$;

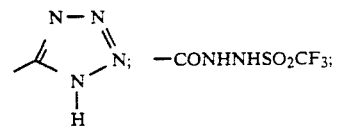 —CONHNHSO$_2$CF$_3$;

alky of 1 to 5 carbon atoms; perfluoroalkyl of 1 to 5 carbon atoms; CN; —CO$_2$R$^{15}$, or where R$^1$ and R$^2$ or R$^3$ and R$^4$ are taken together to form an aliphatic ring of 3 to 6 carbon atoms; and where at least one of $R^1$, $R^2$, $R^3$, and $R^4$ is always an acidic group defined by —COOH, —CONHOR$^{14}$;

—CONHNHSO$_2$CF$_3$; 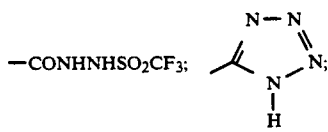

$R^5$ and $R^6$ are H;

$R^7$ is H, Cl, Br, I, NO$_2$, perfluoroalkyl of 1 to 5 carbon atoms; —COR$^{17}$; alkyl of 1 to 5 carbon atoms; phenyl; phenylthio; alkenyl of 2 to 5 carbon atoms; alkynyl of 2 to 5 carbon atoms; phenylalkenyl where the alkenyl portion is 2 to 5 carbon atoms; phenylalkynyl where the alkenyl portion is 2 to 5 carbon atoms;

$R^8$ is H, COR$^{17}$; —(CH$_2$)$_{n-1}$CH$_2$(OR$^{18}$);

$R^9$ is alkyl of 2 to 6 carbon atoms; alkenyl or alkynyl of 2 to 6 carbon atoms; alkylthio where the alkyl portion is of 2 to 5 carbon atoms;

$R^{10}$, $R^{11}$, $R^{12}$, $R^{13}$ are H;

$R^{14}$ is H, methyl or benzyl;

$R^{15}$ is H; alkyl of 1 to 5 carbon atoms; phenyl;

$R^{17}$ is H, alkyl of 1 to 6 carbon atoms; —OR$^{15}$; —NR$^{18}$R$^{19}$;

$R^{18}$ and $R^{19}$ are independently H, alkyl of 1 to 5 carbon atoms; phenyl;

$R^{20}$ and $R^{21}$ are independently —H, Cl; Br; I; —SR$^{15}$; —R$^{17}$; —CN; —OR$^{15}$; phenyl; substituted phenyl where the substituents are alkoxy of 1 to 5 carbon atoms, alkyl of 1 to 5 carbon atoms, fluorine;

Z is N; CH;

X is C-R$^7$; C-R$^8$; N;

Y is C-R$^8$; C-R$^7$; N;

X and Y are carbon atoms and Z is N when they are part of the following ring system:

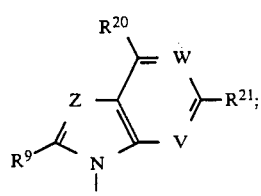

V is CH or N when W is CH;
W is CH or N when V is CH;
n is 1-5.

4. A compound of claim 3 selected from the group consisting of
(±)-11R,12R-trans-2-[(2-n-butyl-4-chloro-5-formylimidazol-1-yl)methyl]-9,10-dihydro-9,10-ethano-11,12-bis(1H-tetrazol-5-yl)anthracene
(±)-11S,12S-trans-2-[(2-n-butyl-4-chloro-5-formylimidazol-1-yl)methyl]-9,10-dihydro-9,10-ethano-11,12-bis(1H-tetrazol-5-yl)anthracene
(±)-trans-2-[(2-n-butyl-4-phenylthio-5-formylimidazol-1-yl)methyl]-9,10-dihydro-9,10-ethano-11,12-bis(1H-tetrazol-5-yl)anthracene
endo-(±)-cis-2-[(2-n-butyl-4-chloro-5-formylimidazol-1-yl)methyl]-9,10-dihydro-9,10-ethano-11,12-(cyclobut-1,2-yl)-11-(1H-tetrazol-5-yl)-12-(cyano)anthracene
exo-(±)-cis-2-[(2-n-butyl-4-chloro-5-formylimidazol-1-yl)methyl]-9,10-dihydro-9,10-ethano-11,12-(cyclobut-1,2-yl)-11-(1H-tetrazol-5-yl)-12-(cyano)anthracene
endo-(±)-cis-2-[(2-n-butyl-4-chloro-5-formylimidazol-1-yl)methyl]-9,10-dihydro-9,10-ethano-11,12-(cyclobut-1,2-yl)-11-(cyano)-12-(1H-tetrazol-5-yl)anthracene
exo-(±)-cis-2-[(2-n-butyl-4-chloro-5-formylimidazol-1-yl)methyl]-9,10-dihydro-9,10-ethano-11,12-(cyclobut-1,2-yl)-11-(cyano)-12-(1H-tetrazol-5-yl)anthracene
(±)-12R-2-[(2-n-butyl-4-chloro-5-formylimidazol-1-yl)methyl]-9,10-dihydro-9,10-ethano-11,11-bistrifluoromethyl10-12-cyano-12-(1H-tetrazol-5-yl)anthracene
(±)-12S-2-[(2-n-butyl-4-chloro-5-formylimidazol-1-yl)methyl]-9,10-dihydro-9,10-ethano-11,11-bistrifluoromethyl10-12-cyano-12-(1H-tetrazol-5-yl)anthracene
(±)-11R-2-[(2-n-butyl-4-chloro-5-formylimidazol-1-yl)methyl]-9,10-dihydro-9,10-ethano-12,12-bistrifluoromethyl-11-cyano-11-(1H-tetrazol-5-yl)anthracene
(±)-11S-2-[(2-n-butyl-4-chloro-5-formylimidazol-1-yl)methyl]-9,10-dihydro-9,10-ethanol-12,12-bistrifluoromethyl-11-cyano-11-(1H-tetrazol-5-yl)anthracene 5. A pharmaceutical composition comprising a pharmaceutically suitable carrier and a compound of any one of claims 1, 2, 3 or 4.

6. Pharmaceutical composition of claim 5 which additionally contains a diuretic or a non-steroidal anti-inflammatory drug.

7. A method of preventing renal failure in a warm blooded animal resulting from administration of a non-steroidal anti-inflammatory drug which comprises administering, stepwise or in physical combination with the NSAID, a compound of any of claims 1 through 3 in an amount effective to prevent renal failure.

8. A method of treating hypertension in a warm blooded animal comprising administering to the animal in an amount effective to lower the animal's blood pressure a compound of any of claim 1, 2, 3, or 4.

9. Method of claim 8 wherein a diuretic is administered to the animal prior to or simultaneously with the imidazole compound.

10. A method of treating congestive heart failure in a warm-blooded animal comprising administering to the animal a compound of any one of claims 1, 2, 3 or 4 in an amount effective to correct the hemodynamic burden on the heart to relieve the congestion.

* * * * *